(12) United States Patent
Yahata et al.

(10) Patent No.: US 11,734,288 B2
(45) Date of Patent: Aug. 22, 2023

(54) INFORMATION PROVIDING METHOD

(71) Applicant: Panasonic Intellectual Property Management Co., Ltd., Osaka (JP)

(72) Inventors: Hiroshi Yahata, Osaka (JP); Takahiro Nishi, Nara (JP); Tadamasa Toma, Osaka (JP); Toshiyasu Sugio, Osaka (JP); Christopher John Wright, London (GB); Bernadette Elliott Bowman, London (GB); David Michael Duffy, Zurich (CH)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 17/693,474

(22) Filed: Mar. 14, 2022

(65) Prior Publication Data

US 2022/0197919 A1 Jun. 23, 2022

Related U.S. Application Data

(63) Continuation of application No. PCT/JP2020/029916, filed on Aug. 5, 2020.

(30) Foreign Application Priority Data

Jun. 19, 2020 (JP) .................... 2020-106432

(51) Int. Cl.
  *G06F 16/2457* (2019.01)
  *G01N 33/00* (2006.01)
  *G06Q 50/12* (2012.01)
(52) U.S. Cl.
  CPC ... *G06F 16/24578* (2019.01); *G01N 33/0001* (2013.01); *G06Q 50/12* (2013.01)

(58) Field of Classification Search
  CPC ............ G06Q 50/12; G06Q 30/0282; G06Q 30/0631; G06Q 30/0201; G06Q 10/06315;
  (Continued)

(56) References Cited

U.S. PATENT DOCUMENTS

| | | | | |
|---|---|---|---|---|
| 2008/0301551 | A1* | 12/2008 | Gluck ................... | G06Q 10/10 715/700 |
| 2013/0224696 | A1* | 8/2013 | Wolfe ................. | G06F 3/04817 434/127 |

FOREIGN PATENT DOCUMENTS

| | | |
|---|---|---|
| JP | 1-173672 U | 12/1989 |
| JP | 2002-259806 | 9/2002 |

(Continued)

OTHER PUBLICATIONS

International Search Report of PCT application No. PCT/JP2020/029916 dated Oct. 27, 2020.

(Continued)

*Primary Examiner* — Hau H Hoang
(74) *Attorney, Agent, or Firm* — Greenblum & Bernstein, P.L.C.

(57) ABSTRACT

A management server obtains rating information indicating a second user's rating of a dish or restaurant, generates a first evaluation value of the first user's sense of taste based on a measurement test regarding the sense of taste, and generates a second evaluation value of the second user's sense of taste based on a measurement test regarding the sense of taste. One search filter for filtering dishes or restaurants based on rating results of the dishes or the restaurants rated by a second user who has a sense-of-taste characteristic similar to that of the first user is provided on a dish search screen. When the first user uses the search filter to filter dishes or restaurants, and when a first difference between the first and (Continued)

second evaluation values is in a first predetermined range, the second user's rating results are used to filter the dishes or the restaurant.

21 Claims, 40 Drawing Sheets

(58) Field of Classification Search
CPC .. G06Q 30/0218; G06Q 30/02; G06Q 10/101; G06Q 50/01; G06Q 30/0251; G06F 16/9035; G06F 16/285; G06F 16/9537; G06F 16/24578; G06F 16/9535; G06F 16/9538; G06F 16/337; G06F 16/29; G06F 16/907; G06F 16/904; G16H 40/67; G16H 20/60; G16H 50/30; A23V 2002/00; H04W 4/021; H04W 4/35
See application file for complete search history.

(56) References Cited

FOREIGN PATENT DOCUMENTS

| | | |
|---|---|---|
| JP | 2010-033608 | 2/2010 |
| JP | 2010-181975 | 8/2010 |

OTHER PUBLICATIONS

Japan Office Action issued in Japan Patent Application No. 2021-558777, dated Jan. 11, 2022, together with English translation thereof.

\* cited by examiner

FIG. 3

| TEST MEAL KIT ID | PILL A1 | PILL A2 | PILL A3 | ... | PILL F9 |
|---|---|---|---|---|---|
| 001000 | SWEETNESS LEVEL 7 | SALTINESS LEVEL 3 | SOURNESS LEVEL 5 | ... | SALTINESS LEVEL 1 |
| 001001 | UMAMI LEVEL 2 | BITTERNESS LEVEL 9 | TASTELESS | ... | UMAMI LEVEL 3 |
| .. | .. | .. | .. | .. | .. |

FIG. 7

Taste Test (Taste Resolution Test)

Taste the following pills one by one,
and answer whether
they have the same taste or different tastes.

A5 and D6

Same Taste | Different Tastes

Progress Level of Test

FIG. 17

|  | PILL A3 | PILL A6 | PILL C3 | PILL D4 | AMOUNT OF DIFFERENCE FROM CORRECT ANSWER |
|---|---|---|---|---|---|
| ORDER IN CORRECT ANSWER | 1 | 4 | 3 | 2 | — |
| ORDER IN ANSWER | 1 | 2 | 3 | 4 | 8 |

FIG. 18

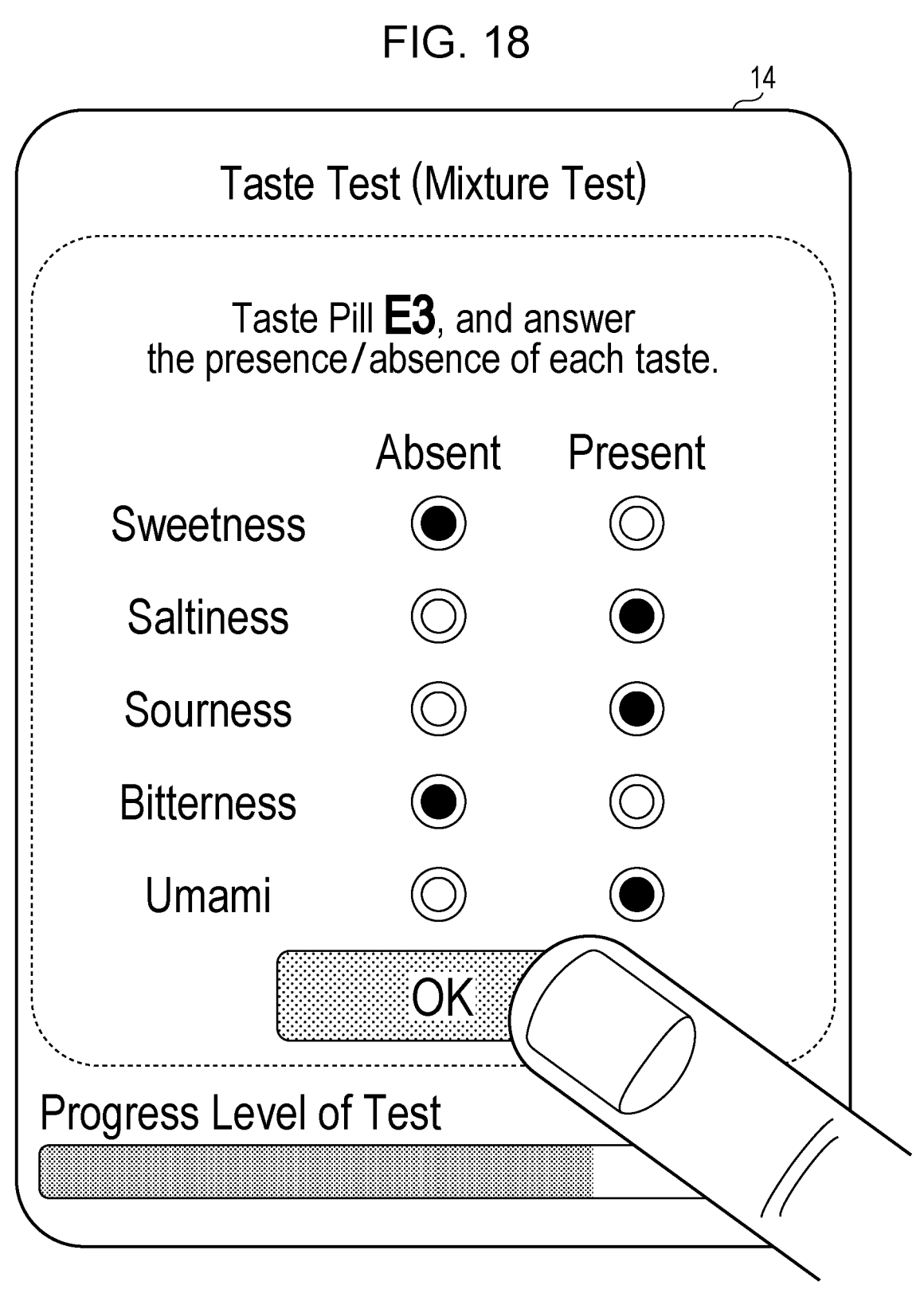

Taste Test (Mixture Test)

Taste Pill E3, and answer the presence/absence of each taste.

|  | Absent | Present |
|---|:---:|:---:|
| Sweetness | ● | ○ |
| Saltiness | ○ | ● |
| Sourness | ○ | ● |
| Bitterness | ● | ○ |
| Umami | ○ | ● |

OK

Progress Level of Test

FIG. 19

| PILL E3 | SWEETNESS LEVEL | SALTINESS LEVEL | SOURNESS LEVEL | BITTERNESS LEVEL | UMAMI LEVEL |
|---|---|---|---|---|---|
| | 2 | 3 | 1 | 0 (NOT CONTAINED) | 0 (NOT CONTAINED) |
| USER'S ANSWER | ABSENT | PRESENT | PRESENT | ABSENT | PRESENT |
| SCORE | -2 | 2 | 4 | 0 | -2 |

FIG. 20

| TASTE LEVEL | 0 (NOT CONTAINED) | 1 | 2 | 3 | 4 |
|---|---|---|---|---|---|
| POINTS ADDED FOR CORRECT ANSWER | 0 | 4 | 3 | 2 | 1 |
| POINTS ADDED FOR INCORRECT ANSWER | -2 | -1 | -2 | -3 | -4 |

FIG. 23

| RATING DATABASE | | |
|---|---|---|
| RESTAURANT NAME | USER ID | RATING |
| RESTAURANT S | 1010 | 4 |
| DISH T OF RESTAURANT S | 1010 | 5 |
| RESTAURANT S | 7367 | 4 |
| : | : | : |

FIG. 24

| USER INFORMATION | |
|---|---|
| USER ID | 1010 |
| SENSE-OF-TASTE SCORE | 684 |
| SENSE-OF-TASTE CHARACTERISTIC | 76, 43, 41, 62, 60 |
| COUNTRY/REGION OF RESIDENCE | JAPAN |
| PREFECTURE OF RESIDENCE | OSAKA PREFECTURE |
| : | : |

INFORMATION PROVIDING METHOD

BACKGROUND

1. Technical Field

The present disclosure relates to a technique for evaluating a user's sense of taste.

2. Description of the Related Art

For example, Japanese Unexamined Utility Model Registration Application Publication No. 1-173672 discloses a taste test film for easily and accurately testing human's ability to distinguish tastes. In the taste test film disclosed in Japanese Unexamined Utility Model Registration Application Publication No. 1-173672, a certain amount of pasty reagent is printed on or applied to a plastic film.

SUMMARY

However, a further improvement is needed in the related art described above.

In one general aspect, the techniques disclosed here feature a method for providing information in an information management system that is used to provide a dish search screen. The method includes: providing, on the dish search screen as one of a plurality of search filters, one search filter for filtering dishes or restaurants based on rating results of the dishes or restaurants rated by a second user who has a sense-of-taste characteristic similar to a sense-of-taste characteristic of a first user; obtaining first data indicating an input value in a measurement test regarding sense of taste of the first user from a first communication terminal through a network, wherein the measurement test regarding the sense of taste is used for measuring taste sensitivity of the first user; obtaining second data indicating an input value in a measurement test regarding sense of taste of the second user from a second communication terminal through the network; obtaining rating information indicating the second user's rating of a dish or a restaurant from the second communication terminal, wherein the rating information indicating the second user's rating of the dish or the restaurant is managed as the second user's rating result of the dish or the restaurant; generating a first evaluation value of the first user's sense of taste in association with the first user, based on the first data; generating a second evaluation value of the second user's sense of taste in association with the second user, based on the second data; and filtering the dishes or the restaurants based on the second user's rating result when a first difference between the first evaluation value and the second evaluation value is in a first predetermined range in a case in which the first user uses the search filter to filter the dishes or the restaurants.

According to the present disclosure, it is possible to achieve a further improvement.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 3 illustrates one example of a table in which pill identifiers (IDs), taste components, and taste component levels are associated for each test meal kit ID;

FIG. 7 is a view illustrating one example of a taste-resolution test screen displayed on a display of a communication terminal in the first embodiment;

FIG. 17 is a table illustrating one example of an in a correct answer, an order in a user's answer, and an amount of difference therebetween in the third modification of the first embodiment;

FIG. 18 is a view illustrating one example of a taste-mixture test screen displayed on the display of the communication terminal in a fourth modification of the first embodiment;

FIG. 19 is a table illustrating one example of a table in which the amount of each taste component contained in a test meal, a result of the user's answer with respect to the taste component, and a score for the taste component are associated with each other in the fourth modification of the first embodiment;

FIG. 20 is a table illustrating one example of a table in which the amount of each taste component contained, points added when an answer is a correct answer, and points added when the answer is an incorrect answer are associated with each other in the fourth modification of the first embodiment;

FIG. 23 is a table illustrating one example of a rating database;

FIG. 24 is a table illustrating one example of user information;

Figure 1:
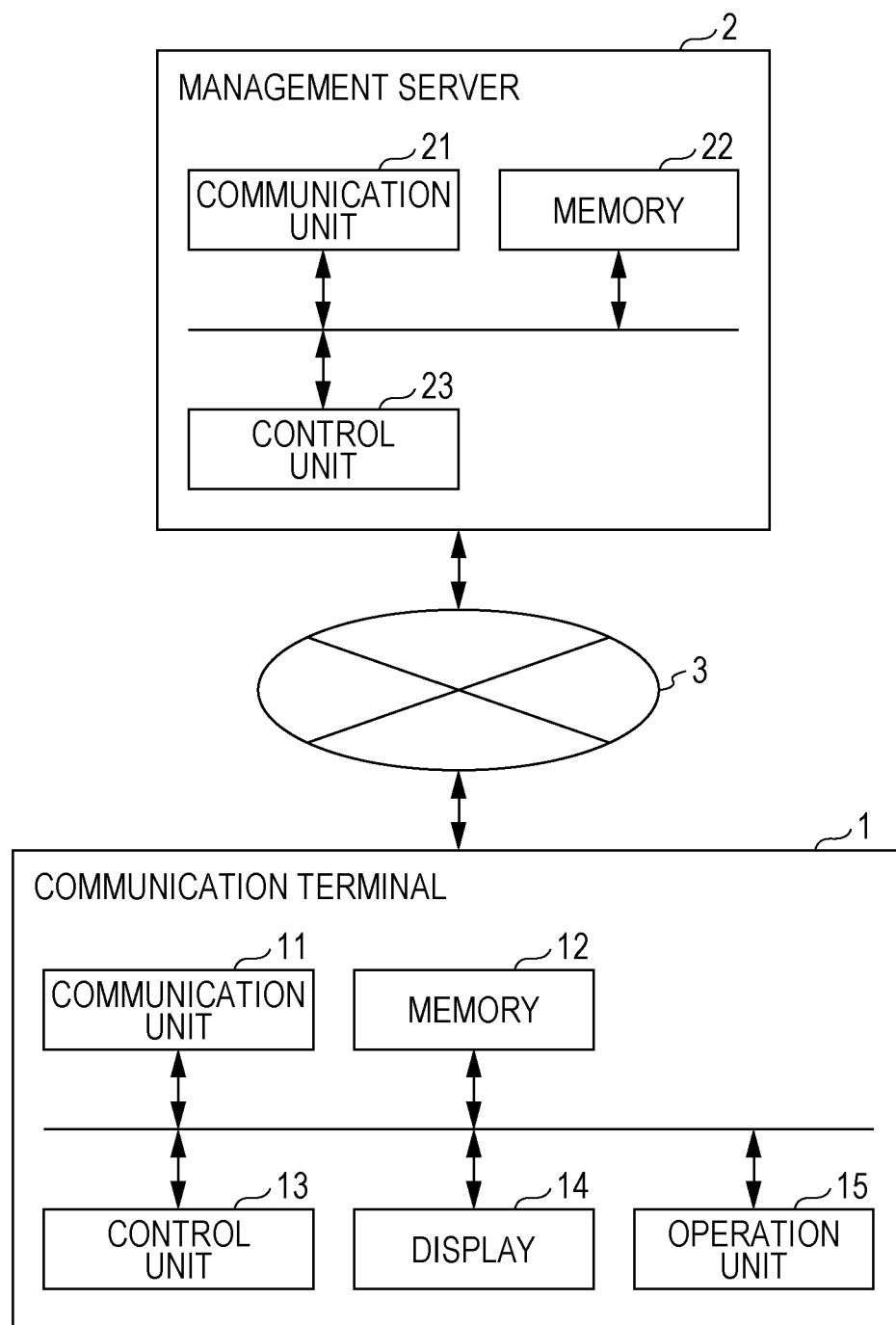
FIG. 1 is a diagram illustrating a configuration of an information management system in a first embodiment of the present disclosure.

DETAILED DESCRIPTIONS (Background from which the Present Disclosure was Derived)

Heretofore, it has been difficult to objectively evaluate human's sense of taste. That is, it has been difficult to objectivize individual people's subjective sensation called "sense of taste". Thus, it has also been difficult to provide services based on sense of taste.

Patent Document 1 discloses measuring human's sense of taste by using a taste test film.

However, in the related technique, a further improvement is needed in order to accurately and easily measure sense of taste and in order to collect information regarding a user's sense of taste.

The present disclosure has been made in order to overcome the above-described problems, and one non-limiting and exemplary embodiment provides a technique that can accurately and easily measure a user's sense of taste and can also collect information regarding the user's sense of taste.

On the basis of the above-described findings, the present inventors have conceived the aspects described below.

A method according to one aspect of the present disclosure is a method for providing information in an information management system that is used to provide a dish search screen. The method includes: providing, on the dish search screen as one of a plurality of search filters, one search filter for filtering dishes or restaurants based on rating results of the dishes or restaurants rated by a second user who has a sense-of-taste characteristic similar to a sense-of-taste characteristic of a first user; obtaining first data indicating an input value in a measurement test regarding sense of taste of the first user from a first communication terminal through a network, wherein the measurement test regarding the sense of taste is used for measuring taste sensitivity of the first user; obtaining second data indicating an input value in a measurement test regarding sense of taste of the second user from a second communication terminal through the network; obtaining rating information indicating the second user's rating of a dish or a restaurant from the second communication terminal, wherein the rating information indicating the second user's rating of the dish or the restaurant is managed as the second user's rating result of the dish or the restaurant; generating a first evaluation value of the first user's sense of taste in association with the first user, based on the first data; generating a second evaluation value of the second user's sense of taste in association with the second user, based on the second data; and filtering the dishes or the restaurants based on the second user's rating result when a first difference between the first evaluation value and the second evaluation value is in a first predetermined range in a case in which the first user uses the search filter to filter the dishes or the restaurants.

According to this configuration, the measurement tests regarding the sense of taste measure the taste sensitivities of the first user and the second user, and based on the first data and second data indicating the input values in the measurement tests of the taste resolutions, evaluation values of the first user's sense of taste and the first second user's sense of taste are generated in association with the respective first user and second user. Thus, it is possible to accurately and easily measure the first user's sense of taste and the second user's sense of taste, and it is also possible to collect information regarding the first user's sense of taste and the second user's sense of taste.

Also, when the first user uses the search filter to filter dishes or restaurants, and the first difference between the first evaluation value of the first user's sense of taste and the second evaluation value of the second user's sense of taste is in the first predetermined range, the second user's rating result is used to filter the dishes or the restaurants. Accordingly, dishes or restaurants highly rated by the second user who has a sense-of-taste characteristic similar to that of the first user can be presented to the first user as a search result.

Also, in the method described above, each measurement test regarding the sense of taste may include a measurement test with respect to at least one type of taste, and the at least one type of taste may include at least one of sweetness, sourness, saltiness, bitterness, or umami; the first evaluation value may include an evaluation value for entire sense of taste including the at least one type of taste; and the second evaluation value may include an evaluation value for entire sense of taste including the at least one type of taste.

According to this configuration, an evaluation value for entire sense of taste including at least one of sweetness, sourness, saltiness, bitterness, or umami can be used to decide whether or not the first user's sense of taste and the second user's sense of taste are similar to each other.

Also, in the method described above, each measurement test regarding the sense of taste may include a measurement test with respect to at least one type of taste, and the at least one type of taste may include at least one of sweetness, sourness, saltiness, bitterness, or umami; the first evaluation value may be represented by a first value indicating sensitivity to a first type of taste and a second value indicating sensitivity to a second type of taste, the first type of taste and the second type of taste being included in two types of taste including the at least one type of taste; the second evaluation value may be represented by a third value indicating sensitivity to the first type of taste and a fourth value indicating sensitivity to the second type of taste; and when a second difference between the first value and the third value and a third difference between the second value and the fourth value are both in a second predetermined range, it may be decided that the first difference is in the first predetermined range.

According to this configuration, when a difference between two types of taste of sweetness, sourness, saltiness, bitterness, and umami is in the second predetermined range, it is decided that the first user's sense of taste and the second user's sense of taste are similar to each other. Thus, it is possible to more accurately determine a degree of similarity between the first user's sense of taste and the second user's sense of taste.

Also, in the method described above, the measurement tests regarding the first user's sense of taste and the second user's sense of taste may include measurement tests of taste resolutions of the first user and the second user; the measurement tests of the taste resolutions may be used to measure what is a smallest difference each of the first user and the second user is capable of recognizing between a plurality of levels with respect to at least one type of taste; the first data may indicate an input value in the measurement test of the taste resolution of the first user; the first evaluation value of the first user's sense of taste may be generated based on at least the first data; the second data may indicate an input value in the measurement test of the taste resolution of the second user; and the second evaluation value of the second user's sense of taste may be generated based on at least the second data.

According to this configuration, the measurement tests of the taste resolutions measure what is a smallest difference each of the first user and the second user is capable of recognizing between a plurality of levels with respect to at least one type of taste, and the first evaluation value of the first user's sense of taste and the second evaluation value of the second user's sense of taste are generated based on the first data and second data indicating the input values in the measurement tests of the taste resolutions. Thus, it is possible to accurately and easily measure the first user's sense of taste and the second user's sense of taste, and it is also possible to collect information regarding the first user's sense of taste and the second user's sense of taste.

Also, in the method described above, the measurement tests regarding the first user's sense of taste and the second user's sense of taste may include measurement tests of taste sensing of the first user and the second user; the measurement tests of the taste sensing may be used to measure, among no taste and a plurality of levels ranging from a light taste to a strong taste of some kind of taste, at which level from no taste each of the first user and the second user is capable of sensing a distinction as to whether there is no taste or any taste; the first data may indicate an input value in the measurement test of the taste sensing of the first user; the first evaluation value of the first user's sense of taste may be generated based on at least the first data; the second data indicates an input value in the measurement test of the taste sensing of the second user; and the second evaluation value of the second user's sense of taste is generated based on at least the second data.

According to this configuration, the measurement test of the taste sensing measures, among no taste and a plurality of levels ranging from a light taste to a strong taste of some kind of taste, at which level from no taste each of the first user and the second user is capable of sensing a distinction as to whether there is no taste or any taste. Then, the first evaluation value of the first user's sense of taste is generated based on the first data indicating the input value in the measurement test of the taste sensing of the first user. Also, the second evaluation value of the second user's sense of taste is generated based on the second data indicating the input value in the measurement test of the taste sensing of the second user. Accordingly, it is possible to measure the first user's sense of taste and the second user's sense of taste with higher accuracy, and it is possible to collect a larger amount of information regarding the first user' sense of taste and the second user's sense of taste.

Also, in the method described above, the measurement tests regarding the first user's sense of taste and the second user's sense of taste may include measurement tests of taste recognition of the first user and the second user; the measurement test of the taste recognition may be used to measure, among no taste and a plurality of levels ranging from a light taste to a strong taste of at least one type of taste, at which level from no taste each of the first user and the second user is capable of recognizing whether there is no taste or the least the one type of taste; the first data may indicate an input value in the measurement test of the taste recognition of the first user; the first evaluation value of the first user's sense of taste is generated based on at least the first data; the second data may indicate an input value in the measurement test of taste recognition of the second user; and the second evaluation value of the second user's sense of taste may be generated based on at least the second data.

According to this configuration, the measurement tests of the taste recognition measure, among no taste and a plurality of levels ranging from a light taste to a strong taste of at least one type of taste, at which level from no taste each of the first user and the second user can recognize a distinction as to whether there is no taste or the at least one type of taste. Then, the first evaluation value of the first user's sense of taste is generated based on the first data indicating the input value in the measurement test of the taste recognition of the first user. Also, the second evaluation value of the second user's sense of taste is generated based on the second data indicating the input value in the measurement test of taste recognition of the second user. Accordingly, it is possible to measure the first user's sense of taste and the second user's sense of taste with higher accuracy, and it is possible to collect a larger amount of information regarding the first user' sense of taste and the second user's sense of taste.

Also, in the method described above, the measurement tests regarding the first user's sense of taste and the second user's sense of taste may include measurement tests of taste densities of the first user and the second user; the measurement tests of the taste densities may be used to measure whether or not each of the first user and the second user is capable of relatively correctly recognizing at least three levels ranging from a light taste to a strong taste with respect to at least one type of taste; the first data may indicate an input value in the measurement test of the taste density of the first user, the first evaluation value of the first user's sense of taste may be generated based on at least the first data; the second data may indicate an input value in the measurement test of the taste density of the second user; and the second evaluation value of the second user's sense of taste may be generated based on at least the second data.

According to this configuration, in the measurement tests of the taste density measures how accurately each user can recognize at least three levels ranging from a light taste to a strong taste with respect to at least one type of taste. Further, the first evaluation value of the first user's sense of taste is generated based on the first data indicating the input value in the measurement test of the taste density of the first user. Also, the second evaluation value of the second user's sense of taste is generated based on the second data indicating the input value in the measurement test of the taste density of the second user. Accordingly, it is possible to measure the first user's sense of taste and the second user's sense of taste with higher accuracy, and it is possible to collect a larger amount of information regarding the first user' sense of taste and the second user's sense of taste.

Also, in the method described above, the input value in the measurement test of the taste resolution of the first user and the input value in the measurement test of the taste resolution of the second user may be input at the first communication terminal and the second communication terminal, respectively, by using at least i) a first test meal group including a plurality of test meals corresponding to a plurality of levels ranging from a light sweet taste to a strong sweet taste or ii) a second test meal group including a plurality of test meals corresponding to a plurality of levels ranging from a light salty taste to a strong salty taste.

According to this configuration, at least the first test meal group including a plurality of test meals corresponding to a plurality of levels ranging from a light sweet taste to a strong sweet taste or the second test meal group including a plurality of test meals corresponding to a plurality of levels ranging from a light salty taste to a strong salty taste is used to perform the measurement tests of the taste resolution of the first user and the taste resolution of the second user.

Accordingly, it is possible to measure what is the smallest difference each of the first user and the second user can recognize between a plurality of levels with respect to sweetness or saltiness.

Also, in the method described above, a first instruction for making each of the first user and the second user input which of a first sweetness test meal and a second sweetness test meal of the plurality of test meals included in the first test meal group is sweeter may be output onto a display of each of the first communication terminal and the second communication terminal, the first sweetness test meal and the second sweetness test meal having therebetween a first level gap of two or more levels of the plurality of levels ranging from the light sweet taste to the strong sweet taste; and the first data and the second data may be obtained as responses to the first instruction.

According to this configuration, in the measurement tests of the taste resolutions, each of the first user and the second user inputs which of the first sweetness test meal and the second sweetness test meal of the plurality of test meals included in the first test meal group is sweeter, the first sweetness test meal and the second sweetness test meal having therebetween the first level gap of two or more levels of the plurality of levels ranging from the light sweet taste to the strong sweet taste. This makes it possible to measure whether or not each of the first user and the second user can recognize a level difference between the first sweetness test meal and the second sweetness test meal which have therebetween the first level gap of two or more levels.

Also, in the method described above, a second instruction for making each of the first user and the second user input which of a third sweetness test meal and a fourth sweetness test meal of the plurality of test meals included in the first test meal group is sweeter, separately from the first sweetness test meal and the second sweetness test meal, may be output onto the display of each of the first communication terminal and the second communication terminal, the third sweetness test meal and the fourth sweetness test meal having therebetween a second level gap that is narrower than the first level gap among the plurality of levels ranging from the light sweet taste to the strong sweet taste; and the first data and the second data may be obtained as responses to the second instruction.

According to this configuration, in the measurement tests of the taste resolutions, each of the first user and the second user inputs which of the third sweetness test meal and the fourth sweetness test meal of the plurality of test meals included in the first test meal group is sweeter, separately from the first sweetness test meal and the second sweetness test meal, the third sweetness test meal and the fourth sweetness test meal having therebetween the second level gap that is narrow than the first level gap among the plurality of levels ranging from the light sweet taste to the strong sweet taste. This makes it possible to measure whether or not each of the first user and the second user can recognize a level difference between the third sweetness test meal and the fourth sweetness test meal which have therebetween the second level gap narrow than the first level gap.

Also, in the method described above, a third instruction for making each of the first user and the second user input which of a fifth sweetness test meal and a sixth sweetness test meal of the plurality of test meals included in the first test meal group is sweeter, separately from the first sweetness test meal and the second sweetness test meal, may be output onto the display of each of the first communication terminal and the second communication terminal, the fifth sweetness test meal and the sixth sweetness test meal having therebetween a third level gap that is wider than the first level gap among the plurality of levels ranging from the light sweet taste to the strong sweet taste; and the first data and the second data may be obtained as responses to the third instruction.

According to this configuration, in the measurement tests of the taste resolutions, each of the first user and the second user inputs which of the fifth sweetness test meal and the sixth sweetness test meal of the plurality of test meals included in the first test meal group is sweeter, separately from the first sweetness test meal and the second sweetness test meal, the fifth sweetness test meal and the sixth sweetness test meal having the third level gap wider than the first level gap among the plurality of levels ranging from the light sweet taste to the strong sweet taste. This makes it possible to measure whether or not each of the first user and the second user can recognize a level difference between the fifth sweetness test meal and the sixth sweetness test meal which have therebetween the third level gap wider than the first level gap.

Also, in the method described above, the second instruction may be output when it is decided that the response to the first instruction indicates a correct answer.

According to this configuration, when the response to the first instruction indicates a correct answer, the test is further performed using two sweetness test meals having a narrower level gap therebetween, thus making it possible to measure how finely each of the first user and the second user can recognize a level difference between the two sweetness test meals.

Also, in the method described above, the third instruction may be output when it is decided that the response to the first instruction indicates an incorrect answer.

According to this configuration, when the response to the first instruction indicates an incorrect answer, the test is performed using two sweetness test meals having a wider level gap, thus making it possible to measure a level difference each of the first user and the second user can recognize between the two sweetness test meals.

Also, in the method described above, the input value in the measurement test of the taste sensing of the first user and the input value in the measurement test of the taste sensing of the second user may be input at the first communication terminal and the second communication terminal, respectively, by using at least i) a first test meal group including a plurality of test meals corresponding to a plurality of levels ranging from a light sweet taste to a strong sweet taste, ii) a second test meal group including a plurality of test meals corresponding to a plurality of levels ranging from a light salty taste to a strong salty taste, and iii) a third test meal group including a plurality of tasteless test meals.

According to this configuration, each measurement test of the taste sensing is performed by using at least a first test meal group including a plurality of test meals corresponding to a plurality of levels ranging from a light sweet taste to a strong sweet taste, a second test meal group including a plurality of test meals corresponding to a plurality of levels ranging from a light salty taste to a strong salty taste, and a third test meal group including a plurality of tasteless test meals. Accordingly, it is possible to accurately measure at which level from no taste each of the first user and the second user can sense a distinction as to whether there is no taste or any taste with respect to sweetness or saltiness.

Also, in the method described above, a fourth instruction for making each of the first user and the second user use the first test meal group, the second test meal group, and the third test meal group to input whether the test meals included in the first test meal group or the second test meal group are tasteless or not tasteless in order with a level of a lightest taste first may be output onto a display of each of the first communication terminal and the second communication terminal; and the first data and the second data may be obtained as responses to the fourth instruction.

According to this configuration, in the measurement tests of the taste sensing, each of the first user and the second user uses the first test meal group, the second test meal group, and the third test meal group to input whether the test meals included in the first test meal group or the second test meal group are tasteless or not tasteless in order with a level of a lightest taste first. This makes it possible to accurately measure at approximately which level each of the first user and the second user can sense whether the test meals are tasteless or not tasteless.

Also, in the method described above, the input value in the measurement test of the taste recognition of the first user and the input value in the measurement test of the taste recognition of the second user may be input at the first communication terminal and the second communication terminal, respectively, by using at least a first test meal group including a plurality of test meals corresponding to a plurality of levels ranging from a light sweet taste to a strong sweet taste and a second test meal group including a plurality of tasteless test meals.

According to this configuration, each measurement test of the taste recognition is performed by using at least a first test meal group including a plurality of test meals corresponding to a plurality of levels ranging from a light sweet taste to a strong sweet taste and a second test meal group including a plurality of tasteless test meals. Accordingly, it is possible to accurately measure at which level from no taste each of the first user and the second user can recognize a distinction between no taste and sweet taste.

Also, in the information providing method described above, a fifth instruction for making each of the first user and the second user use the first test meal group and the second test meal group to input whether the test meals included in the first test meal group have no taste or have sweet taste in order with the level of a lightest sweet taste first may be output onto a display of each of the first communication terminal and the second communication terminal; and the first data and the second data may be obtained as responses to the fifth instruction.

According to this configuration, in the measurement tests of the taste recognitions, each of the first user and the second user uses the first test meal group and the second test meal group to input the test meals included in the first test meal group have no taste or have sweet taste in order with the level of a lightest sweet taste first. This makes it possible to accurately measure at which level from no taste each of the first user and the second user can recognize a distinction between no taste and sweet taste.

Also, in the method described above, the input value in the measurement test of the taste density of the first user and the input value in the measurement test of the taste density of the second user may be input at the first communication terminal and the second communication terminal, respectively, by using at least a first test meal group including a plurality of test meals corresponding to a plurality of levels ranging from a light sweet taste to a strong sweet taste.

According to this configuration, each measurement test of the taste density is performed by using at least a first test meal group including a plurality of test meals corresponding to a plurality of levels ranging from a light sweet taste to a strong sweet taste. Accordingly, it is possible to accurately measure how accurately each of the first user and the second user can recognize at least three levels ranging from a light taste to a strong taste with respect to sweetness.

Also, in the method described above, a sixth instruction for making each of the first user and the second user use the first test meal group to input at least three test meals in order of density of taste, the at least three test meals being included in the plurality of test meals included in the first test meal group, may be output onto a display of each of the first communication terminal and the second communication terminal, and the first data and the second data may be obtained as responses to the sixth instruction.

According to this configuration, in the measurement tests of the taste densities, each of the first user and the second user uses the first test meal group to input at least three test meals in order of density of taste, the at least three test meals being included in the plurality of test meals included in the first test meal group. This makes it possible to measure how accurately each of the first user and the second user can recognize a difference in sweetness density between at least three test meals.

A method according to another aspect of the present disclosure is a method for providing information in an information management system that is used to provide a dish search screen. The method includes: providing, on the dish search screen as one of a plurality of search filters, one search filter for filtering dishes or restaurants based on rating results of the dishes or restaurants rated by a second user who has a sense-of-taste characteristic similar to a sense-of-taste characteristic of a first user; obtaining, from a first communication terminal of the first user through a network, a command indicating that the search filter is selected; selecting at least one dish filtered by the search filter or at least one restaurant filtered by the search filter, based on the command; and outputting information indicating the selected at least one dish or restaurant to the first communication terminal through the network to display the information on a display of the first communication terminal.

According to this configuration, dishes or restaurants are filtered by the search filter by using the rating results of the dishes or restaurants rated by the second user who has a sense-of-taste characteristic similar to a sense-of-taste characteristic of the first user, and at least one dish filtered by the search filter or at least one restaurant filtered by the search filter is displayed on the display of the first communication terminal. Accordingly, dishes or restaurants highly rated by the second user who has a sense-of-taste characteristic similar to that of the first user can be presented to the first user as a search result.

Also, in the method described above, first data indicating an input value in a measurement test regarding sense of taste of the first user may be obtained from the first communication terminal through the network, the measurement test regarding the sense of taste being used for measuring taste sensitivity of the first user; second data indicating an input value in a measurement test regarding sense of taste of the second user may be obtained from the second communication terminal of the second user through the network; rating information indicating the second user's rating of a dish or a restaurant may be obtained from the second communication terminal, the rating information indicating the second user's rating of the dish or the restaurant may be included in the second user's rating results of the dishes or the restaurants; a first evaluation value of the first user's sense of taste may be generated in association with the first user based on the first data; a second evaluation value of the second user's sense of taste may be generated in association with the second user based on the second data; and the dishes or the restaurants may be filtered based on the second user's rating results when a first difference between the first evaluation value and the second evaluation value is in a first predetermined range in a case in which the first user uses the search filter to filter the dishes or the restaurants.

According to this configuration, when the first difference between the first evaluation value and the second evaluation value is in the first predetermined range, the second user's rating results are used to filter the dishes or the restaurants. Accordingly, it is possible to filter dishes or restaurants by using the rating results of the second user who has a sense-of-taste characteristic similar to that of the first user.

Embodiments of the present disclosure will be described below with reference to the accompanying drawings. The embodiments described below are embodied examples of the present disclosure and are not intended to limit the technical scope of the present disclosure.

First Embodiment

FIG. 1 is a diagram illustrating a configuration of an information management system in a first embodiment of the present disclosure.

The information management system illustrated in FIG. 1 includes a communication terminal 1 and a management server 2.

The communication terminal 1 is, for example, a smartphone, a tablet computer, or a personal computer and is used by a user. The communication terminal 1 includes a communication unit 11, a memory 12, a control unit 13, a display 14, and an operation unit 15. The communication terminal 1 is connected to the management server 2 through a network 3 so as to be able to communicate with each other. The network 3 is, for example, the Internet.

The communication unit 11 receives various types of information from the management server 2 and also transmits various types of information to the management server 2. The communication unit 11 receives information on a measurement test regarding sense of taste, the information being transmitted by the management server 2. The measurement test regarding the sense of taste is used in order to measure the user's taste sensitivity. In the first embodiment, the measurement test regarding the sense of taste includes a measurement test of a taste resolution. The measurement test of the taste resolution is used in order to measure what is a smallest difference the user can recognize between a plurality of levels with respect to at least one type of taste. The at least one type of taste is at least one of sweetness, sourness, saltiness, bitterness, and umami.

The memory 12 is, for example, a semiconductor memory or a hard-disk drive and stores various types of information therein.

The control unit 13 is, for example, a central processing unit (CPU) and controls the entire communication terminal 1.

The display 14 is, for example, a liquid-crystal display device and displays various types of information. The display 14 displays the measurement test regarding the sense of taste, the measurement test being received by the communication unit 11.

The operation unit 15 is, for example, a touch panel, a keyboard, or a mouse and receives the user's inputs of various types of information. The operation unit 15 receives the user's input of an answer to the measurement test regarding the sense of taste. The operation unit 15 is one example of an input device and is provided at the communication terminal 1 of the user.

Also, the communication unit 11 transmits first data indicating input values in the measurement test regarding the user's sense of taste to the management server 2. The communication unit 11 receives evaluation values of the user's sense of taste, the evaluation values being generated by the management server 2. The display 14 displays information indicating the evaluation values of the user's sense of taste, the evaluation values being received by the communication unit 11.

The management server 2 is, for example, a web server. The management server 2 includes a communication unit 21, a memory 22, and a control unit 23.

The control unit 23 is, for example, a CPU and controls the entire management server 2. The control unit 23 generates information on the measurement test regarding the sense of taste.

The communication unit 21 receives various types of information from the communication terminal 1 and also transmits various types of information to the communication terminal 1. The communication unit 21 transmits the information on the measurement test regarding the sense of taste to the communication terminal 1, the information being generated by the control unit 23. The communication unit 21 obtains the first data indicating the input values in the measurement test regarding the user's sense of taste, the input values being input using the operation unit 15 of the communication terminal 1. The communication unit 21 receives the first data transmitted by the communication terminal 1.

One type of the measurement test regarding the sense of taste is the measurement test of the taste resolution. The taste resolution indicates a smallest amount of difference with which the user can perceive a difference in the amount of a specific taste component per test meal. It has been known that the taste resolution differs from one subject to another. It is also known that, even for the same subject, the taste resolution differs for each taste component. The taste resolution may be represented by a difference in density, not the amount of difference.

Based on the first data received by the communication unit 21, the control unit 23 generates evaluation values of the user's sense of taste in association with the user. The control unit 23 registers information indicating the evaluation values in the memory 22. In order to display the information indicating the evaluation values on the display 14 of the communication terminal 1, the communication unit 21 outputs the information indicating the evaluation values to the communication terminal 1.

The memory 22 is, for example, a semiconductor memory or a hard-disk drive and stores various types of information therein. The memory 22 stores user information in which a user ID for identifying the user and the evaluation values of the user's sense of taste are associated with each other. The control unit 23 stores, in the memory 22, the user information in which the user ID and the generated evaluation values are associated with each other.

Input values in the measurement test of the taste resolution of the user are input at the operation unit 15 by using at least a first test meal group including a plurality of test meals corresponding to a plurality of levels ranging from a light sweet taste to a strong sweet taste or a second test meal group including a plurality of test meals corresponding to a plurality of levels ranging from a light salty taste to a strong salty taste. The communication unit 21 outputs a first instruction for making the user input which of a first sweetness test meal and a second sweetness test meal of the plurality of test meals included in the first test meal group is sweeter to the communication terminal 1, the first sweetness test meal and the second sweetness test meal having therebetween a first level gap of two or more levels of the plurality of levels ranging from the light sweet taste to the strong sweet taste. The communication unit 21 obtains the first data as a response to the first instruction.

Also, the control unit 23 outputs a second instruction for making the user input which of a third sweetness test meal and a fourth sweetness test meal of the plurality of test meals included in the first test meal group is sweeter, separately from the first sweetness test meal and the second sweetness test meal, to the communication terminal 1 via the communication unit 21, the third sweetness test meal and the fourth sweetness test meal having therebetween a second level gap that is narrower than the first level gap among the plurality of levels ranging from the light sweet taste to the strong sweet taste. Upon deciding that the response to the first instruction indicates a correct answer, the control unit 23 outputs the second instruction via the communication unit 21. The control unit 23 obtains first data as a response to the second instruction from the communication terminal 1 via the communication unit 21.

In addition, the control unit 23 outputs a third instruction for making the user input which of a fifth sweetness test meal and a sixth sweetness test meal of the plurality of the test meals included in the first test meal group is sweeter, separately from the first sweetness test meal and the second sweetness test meal, to the communication terminal 1 via the communication unit 21, the fifth sweetness test meal and the sixth sweetness test meal having therebetween a third level gap that is wider than the first level gap among the plurality of levels ranging from the light sweet taste to the strong sweet taste. Upon deciding that the response to the first instruction indicates an incorrect answer, the control unit 23 outputs the third instruction via the communication unit 21. The control unit 23 obtains first data as a response to the third instruction via the communication unit 21.

The first test meal group and the second test meal group are managed using a common test meal kit identifier (ID).

Now, the test meals will be described. The test meals are contained in a test meal kit, which is provided to the user.

Figure 2:
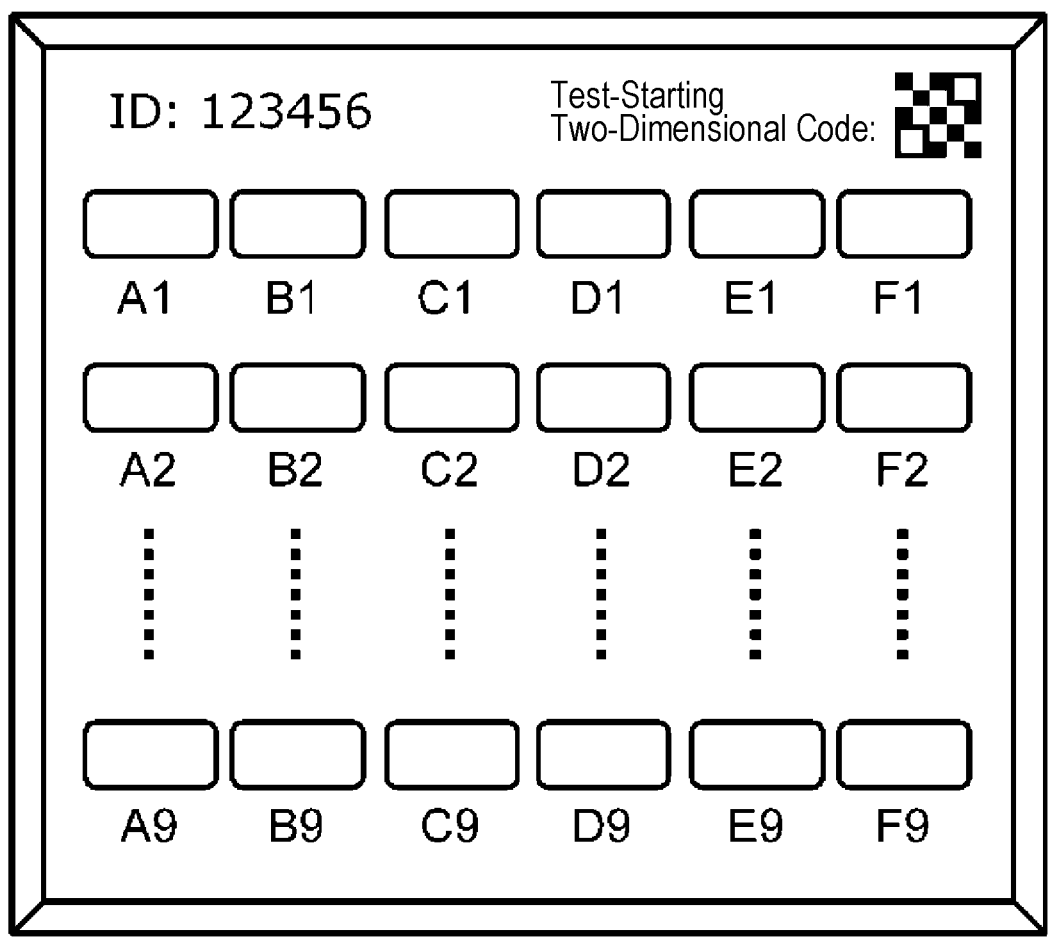
FIG. 2 is a view illustrating one example of a test meal kit in the first embodiment.

FIG. 2 is a view illustrating one example of the test meal kit in the first embodiment.

The test meal kit ID (a common identifier) for identifying the test meal kit and a two-dimensional code (a common identifier) for starting the test are printed on the test meal kit. The test meal kit includes a plurality of test meals. The test meals are in the form of pills. Pill IDs (individual identifiers) for identifying the respective test meals are printed on a box of the test meal kit and/or the respective pills.

It has been known that human's sense of taste is perceived by a collection of taste cells called taste buds. Five components, that is, sweetness, saltiness, sourness, bitterness, and umami, are taste components perceived by taste cells that constitute the taste buds. In the example illustrated in FIG. 2, the test meal kit includes a total of 54 pills to which pill IDs A1 to A9, B1 to B9, C1 to C9, D1 to D9, E1 to E9, and F1 to F9 are assigned. Forty-five pills of the 54 pills include nine pills containing different amounts of meals for each of the five types of taste component. That is, with respect to sweetness, a total of nine pills, ranging from a pill with sweetness level 1 which contains a predetermined amount of a sweetness component to a pill with sweetness level 9 which contains an amount of a sweetness component increased stepwisely, relative to a tasteless pill, are used.

Similarly, nine pills containing stepwisely different amounts of meals are prepared with respect to each of the four other taste components. The remaining nine pills of the 54 pills are tasteless. This set of 54 pills may be used for one type of test, and one test meal kit may contain a plurality of pill sets that are respectively used for a plurality of types of taste test.

The test meal kit ID and/or the two-dimensional code are/is individually issued for each test meal kit. The user can smoothly start the taste test (such as the measurement test of the taste resolution) by inputting the test meal kit ID on a website or by reading the two-dimensional code, including a uniform resource locator (URL) of a website, with a camera (not illustrated) included in the communication terminal 1.

A computer system that executes the measurement test regarding the user's sense of taste uses the common identifier(s) (the test meal kit ID and/or the two-dimensional code) and the individual identifiers (the pill IDs) to determine the types of taste component and the amounts thereof in the test meals. Also, for executing the measurement test regarding the user's sense of taste, the computer system uses the individual identifiers (the pill IDs) in order to specify test meals for the user. The common identifier may be given in the form of a two-dimensional code including URL information for starting the measurement test regarding the user's sense of taste.

Every test meal kit includes a same combination of test meals. However, associations between the pill IDs and the taste components differ for each different test meal kit ID and each different two-dimensional code. In this example, a total of 54 pill IDs A1 to F9 are used for identification. The combination of 54 pills is also equally used for every test meal kit. However, the 54 pill IDs are given to pills containing taste components that differ from one test meal kit to another. That is, when the test meal kit IDs are different, the pills do not necessarily contain the same taste component, even with the same pill ID. In one test meal kit, pills containing the same taste component may be represented by the same pill ID or may be represented by different pill IDs.

This is, firstly, to obtain an advantage that the same test meal can be used in a plurality of taste tests, and thus the manufacturing cost can be reduced due to the mass production effect. Thus, the pill IDs are not printed on the pills and are presented to the user by using a medium other than the pills. One example of the medium is the box of the test meal kit. For example, the pill IDs may be printed on corresponding portions immediately below a package containing the pills. Also, the pills may be manufactured so that all the pills have the same appearance features and are seemingly distinguishable.

Secondly, rather than distributing the same test meal kits to all taste-test practitioners, different test meal kits are distributed to the taste test practitioners to perform taste tests to thereby prevent fraudulent activities. Even in test meal kits on which the same pill ID is printed, pills containing different taste components are associated therewith when the test meal kit ID is different.

In addition, in each taste test in the first embodiment, an amount of difference between the user's answer and a correct answer in the taste test is determined, and a next question is generated dynamically. Thus, a taste test is generated individually for each subject. Accordingly, whether or not the same taste test is to be performed for each subject becomes indefinite, thus making fraudulent activities more difficult.

Although each test meal has been described as being in the form of a pill, the present disclosure is not limited thereto. For example, each test meal may be in the form of a tablet, powder, or paste, not in the form of a pill, and the test may be conducted in a manner that the user tastes it directly. Alternatively, the test may be conducted in a manner that the user dissolves the pill, the powder, or the paste with a predetermined amount of water and tastes it. Alternatively, the test may be conducted in a manner that the user tastes the pill, the powder, or the paste together with predetermined foodstuff. The predetermined foodstuff is, for example, tasteless foodstuff, such as tasteless bread or a tasteless cookie, for aiding swallowing.

FIG. 3 illustrates one example of a table in which pill IDs, taste components, and the levels of the taste components are associated for each test meal kit ID.

The memory 22 in the management server 2 stores therein the table in which the pill IDs, the taste components, and the levels of the taste components are associated for each test meal kit ID. By referring to the table at the time of starting a taste test, the control unit 23 can identify what is the level of the taste component in a pill with each pill ID, in accordance with the test meal kit ID input by the user. At level 1 of each taste component, the amount of the taste component contained is the smallest, and the taste is the lightest; and at level 9 of each taste component, the amount of the taste component contained is the largest, and the taste is the strongest.

During generation of a taste test, the control unit 23 can change and correctly specify pills used in the taste test for each test meal kit ID.

Although, in the first embodiment, one pill contains one type of taste component, the present disclosure is not particularly limited thereto. One pill may contain a plurality of types of taste component. For example, pill A2 illustrated in FIG. 3 may contain a bitterness component with bitterness level 9 and a saltiness component with saltiness level 4.

Subsequently, a description will be given of sense-of-taste evaluation processing for evaluating the user's sense of taste in the first embodiment of the present disclosure.

Figure 4:
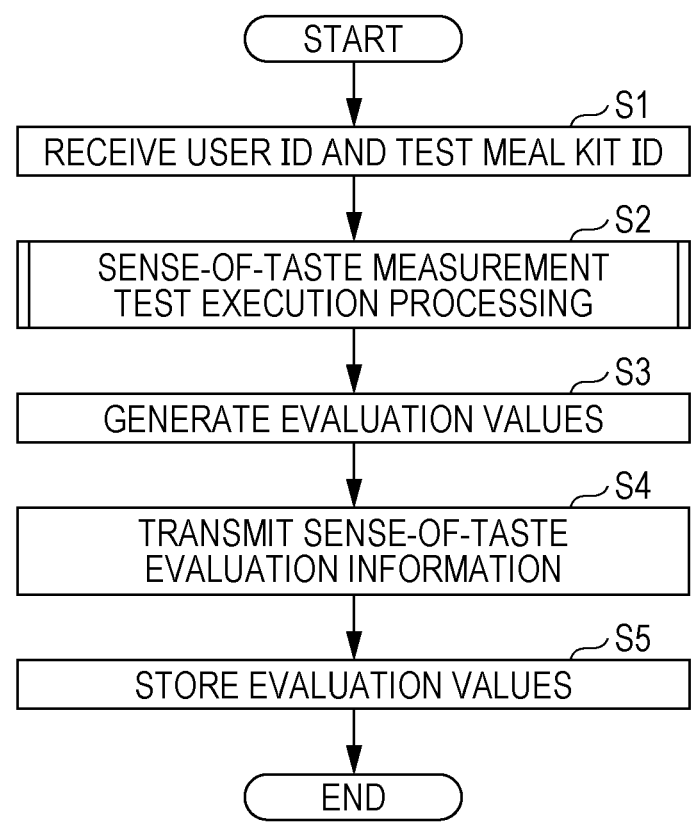
FIG. 4 is a flowchart illustrating sense-of-taste evaluation processing in a management server in the first embodiment of the present disclosure.

FIG. 4 is a flowchart illustrating sense-of-taste evaluation processing in the management server in the first embodiment of the present disclosure.

First, in step S1, the communication unit 21 receives the user ID and a test meal kit ID transmitted by the communication terminal 1. In this case, the communication terminal 1 receives a user's inputs of a test meal kit ID printed on a test meal kit and a user ID. The communication terminal 1 displays an input screen, provided by the management server 2, on a web browser and receives inputs of the user ID and the test meal kit ID via the input screen. The input screen is specified by a predetermined uniform resource locator (URL). The communication terminal 1 transmits the input user ID and test meal kit ID to the management server 2.

The communication terminal 1 may have a two-dimensional code reader. The two-dimensional code reader may read the two-dimensional code printed on the test meal kit. The two-dimensional code includes a URL of the management server 2. By reading the two-dimensional code, the communication terminal 1 may display the input screen, provided by the management server 2, on the web browser, may receive an input of the user ID via the input screen, and may further receive an input of the test meal kit ID, as appropriate.

In step S2, the control unit 23 executes sense-of-taste measurement test execution processing. In the sense-of-taste measurement test execution processing, a sense-of-taste measurement test for measuring the user's sense of taste is generated, and also first data indicating input values in the sense-of-taste measurement test is obtained. Taste-resolution measurement test execution processing for measuring the taste resolution is described later with reference to FIGS. 5 and 6.

In step S3 in FIG. 4, based on the first data, the control unit 23 generates evaluation values of the user's sense of taste in association with the user.

Next, in step S4, the control unit 23 transmits, to the communication terminal 1, sense-of-taste evaluation information indicating the generated evaluation values. The communication unit 11 in the communication terminal 1 receives the sense-of-taste evaluation information transmitted by the management server 2. The display 14 of the communication terminal 1 then displays the sense-of-taste evaluation information received by the communication unit 11.

Next, in step S5, the control unit 23 stores the generated evaluation values in the memory 22 in association with the user ID.

Subsequently, a description will be given of taste-resolution measurement test execution processing, which is one type of sense-of-taste measurement test execution processing in step S2 in FIG. 4.

Figure 5:
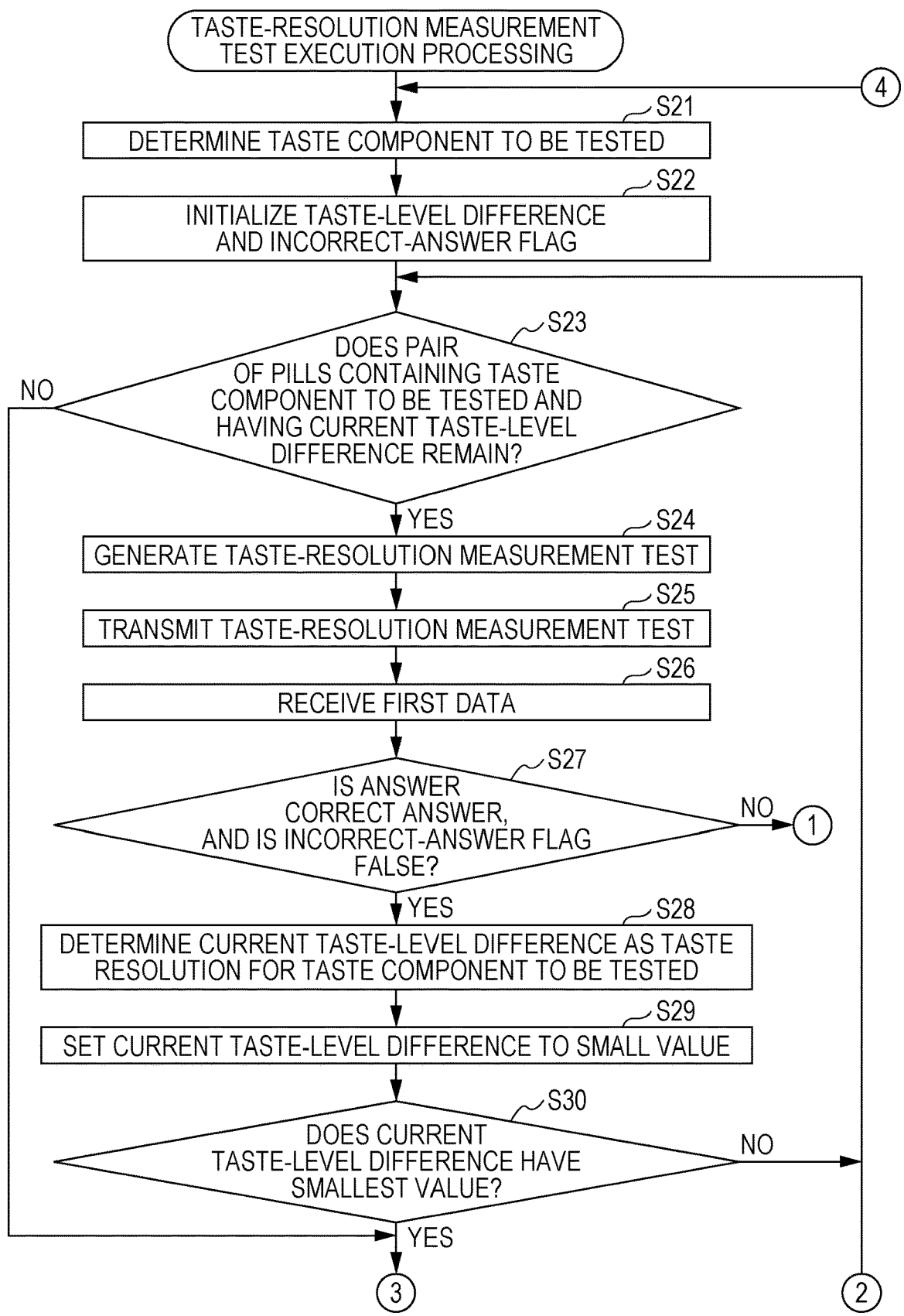
FIG. 5 is a first flowchart illustrating taste-resolution measurement test execution processing, which is one type of sense-of-taste measurement test execution processing in step S2 in FIG. 4.
Figure 6:
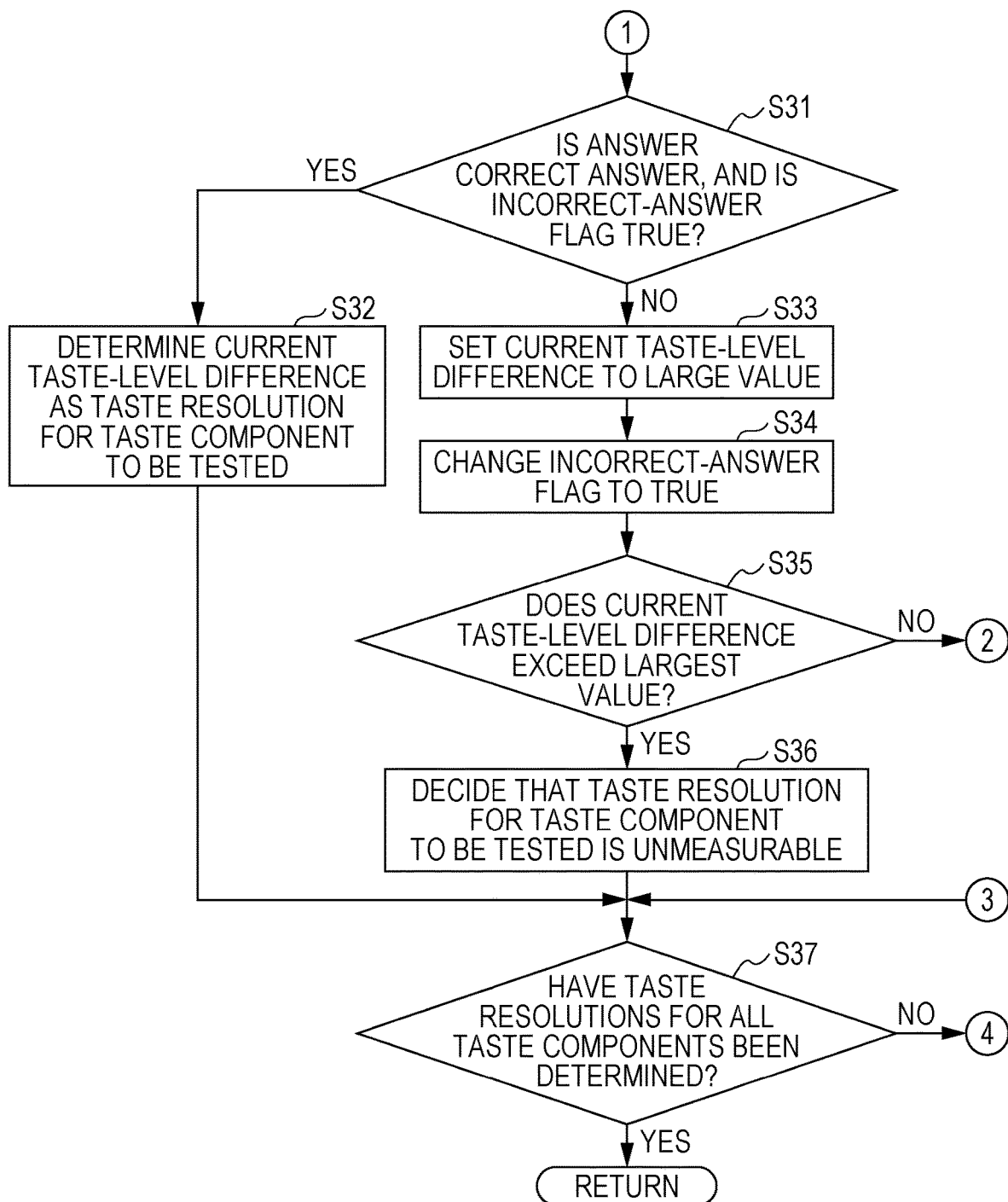
FIG. 6 is a second flowchart illustrating the taste-resolution measurement test execution processing, which is one type of sense-of-taste measurement test execution processing in step S2 in FIG. 4.

FIG. 5 is a first flowchart illustrating the taste-resolution measurement test execution processing, which is one type of sense-of-taste measurement test execution processing in step S2 in FIG. 4, and FIG. 6 is a second flowchart thereof.

First, in step S21, the control unit 23 determines a taste component to be tested. The control unit 23 determines an untested taste component of five taste components, that is, sweetness, saltiness, sourness, bitterness, and umami, as a taste component to be tested. In the first embodiment, the control unit 23 measures a taste resolution for each of the five taste components.

In step S22, the control unit 23 initializes a taste-level difference and an incorrect-answer flag (i.e., sets the flag to FALSE). The initialized taste-level difference is, for example, 4.

Next, in step S23, the control unit 23 decides whether or not a pair of pills containing the taste component to be tested and having the current taste-level difference therebetween remains. When it is decided that a pair of pills containing the taste component to be tested and having the current taste-level difference therebetween does not remain (NO in step S23), the process proceeds to a process in step S37.

On the other hand, when it is decided that a pair of pills containing the taste component to be tested and having the current taste-level difference therebetween remains (YES in step S23), in step S24, the control unit 23 specifies two pills containing the taste component to be tested and having the current taste-level difference therebetween and generates a taste-resolution measurement test for obtaining an answer as to whether or not the specified two pills have the same taste.

For example, when a taste resolution for sweetness is to be first tested, the control unit 23 uses a pill with sweetness level 3 and a pill with sweetness level 7 to test whether or not the user can perceive the sweetness difference (the sweetness level difference=4).

Next, in step S25, the communication unit 21 transmits the taste-resolution measurement test generated by the control unit 23 to the communication terminal 1. Then, the communication unit 11 in the communication terminal 1 receives the taste-resolution measurement test. The display 14 of the communication terminal 1 displays the taste-resolution measurement test received by the communication unit 11. In this taste-resolution measurement test, the user is prompted to eat two pills containing the taste component to be tested and having the current taste-level difference therebetween, and an answer as to whether or not the tastes of the two pills are the same is received. The two pills are specified by the pill IDs. The user eats the specified two pills and inputs whether or not the tastes of the two pills are the same. The communication unit 11 transmits, to the management server 2, first data indicating the user's input value (answer) with respect to the taste-resolution measurement test.

In step S26, the communication unit 21 receives the first data transmitted by the communication terminal 1.

Next, in step S27, the control unit 23 decides whether or not the user's input value (answer) with respect to the taste-resolution measurement test is a correct answer and whether or not the incorrect-answer flag is FALSE. When it is decided that the input value (answer) is a correct answer, and the incorrect-answer flag is FALSE (YES in step S27), in step S28, the control unit 23 determines the current taste-level difference as a taste resolution for the taste component to be tested (that is, as an evaluation value for the taste resolution for the type of taste with respect to the user).

Next, in step S29, the control unit 23 sets the current taste-level difference to a small value. For example, when the current taste-level difference is 4, the control unit 23 sets the current taste-level difference to 2. When the previous test was performed using a pill with taste level 3 and a pill with taste level 7, the control unit 23 performs, for example, a test having a taste-level difference of 2 and using a pill with taste level 4 and a pill with taste level 6.

Next, in step S30, the control unit 23 decides whether or not the current taste-level difference has a smallest value. When it is decided that the current taste-level difference has the smallest value (YES in step S30), the process proceeds to step S37.

On the other hand, when it is decided that the current taste-level difference does not have the smallest value (NO in step S30), the process returns to step S23. For example, when the current taste-level difference is 2, the control unit 23 uses a pill with sweetness level 4 and a pill with sweetness level 6 to test whether or not the user can perceive the sweetness difference (the sweetness level difference=2).

Also, when it is decided in step S27 that the conditions that the input value (answer) is a correct answer and the incorrect-answer flag is FALSE are not satisfied (NO in step S27), in step S31, the control unit 23 decides whether or not the input value (answer) is a correct answer and whether or not the incorrect-answer flag is TRUE. When it is decided that the input value (answer) is a correct answer, and the incorrect-answer flag is TRUE (YES in step S31), in step S32, the control unit 23 determines the current taste-level difference as the taste resolution for the taste component to be tested (i.e., as an evaluation value for the taste resolution for the type of taste with respect to the user).

On the other hand, when it is decided that the conditions that the input value (answer) is a correct answer and the incorrect-answer flag is TRUE are not satisfied, in other words, when the user gives an incorrect answer in the taste-resolution measurement test for the first time (the answer is an incorrect answer, and the incorrect-answer flag is FALSE) or when the answer is continuously an incorrect answer (the answer is an incorrect answer, and the incorrect-answer flag is TRUE) (NO in step S31), in step S33, the control unit 23 sets the current taste-level difference to a large value. For example, when the current taste-level difference is 4, the control unit 23 sets the current taste-level difference to 6. When the previous test was performed using a pill with taste level 3 and a pill with taste level 7, the control unit 23 performs, for example, a test having a taste-level difference of 6 and using a pill with taste level 2 and a pill with taste level 8.

Next, in step S34, the control unit 23 changes the incorrect-answer flag to TRUE.

Next, in step S35, the control unit 23 decides whether or not the current taste-level difference exceeds a largest value. When it is decided that the current taste-level difference does not exceed the largest value (NO in step S35), the process returns to step S23.

On the other hand, when it is decided that the current taste-level difference exceeds the largest value (YES in step S35), in step S36, the control unit 23 decides that the taste resolution for the taste component to be tested is unmeasurable. The taste resolution for the taste component to be tested, the taste resolution being determined by the control unit 23, may be the current taste-level difference, a value larger than the current taste-level difference, a largest taste-level difference that is measurable with the test meal kit, or a value larger than the largest taste-level difference that is measurable with the test meal kit.

Next, in step S37, the control unit 23 decides whether or not taste resolutions for all the taste components have been determined. When it is decided that taste resolutions for all the taste components have not been determined (NO in step S37), the process returns to step S21.

On the other hand, when it is decided that the taste resolutions for all the taste components have been determined (YES in step S37), the taste-resolution measurement test execution processing ends.

In the taste resolution test, the control unit 23 stepwise increases the taste-level difference when the answer is an incorrect answer and stepwise reduces the taste-level difference when the answer is a correct answer, as described above. In addition, the smallest taste-level difference for which the correct answer is given is determined to be the taste resolution of the user. Taste resolutions are similarly measured for the other taste components. When the pills used for the measurement run out, the taste resolution test ends. Also, when the taste resolution test reaches a measurement limit, the taste resolution test ends. No test is performed with respect to a taste-level difference that is smaller than the taste-level difference with which the user failed. This is to prevent the answer of the user from being a correct answer by chance and to maintain the measurement accuracy.

FIG. 7 is a view illustrating one example of a taste-resolution test screen displayed on the display of the communication terminal in the first embodiment.

The taste-resolution test screen illustrated in FIG. 7 is displayed on the display 14 of the communication terminal 1. The taste-resolution test screen includes the pill IDs of two pills that the user is to eat, a first answer button indicating that the two pills have the same taste, and a second answer button indicating that the two pills have different tastes. The user eats the specified two pills and gives an answer as to whether or not the two pills have the same taste. When the user feels that the two pills have the same taste, he or she touches the first answer button. When the user feels that the two pills have different tastes, he or she touches the second answer button.

Figure 8:
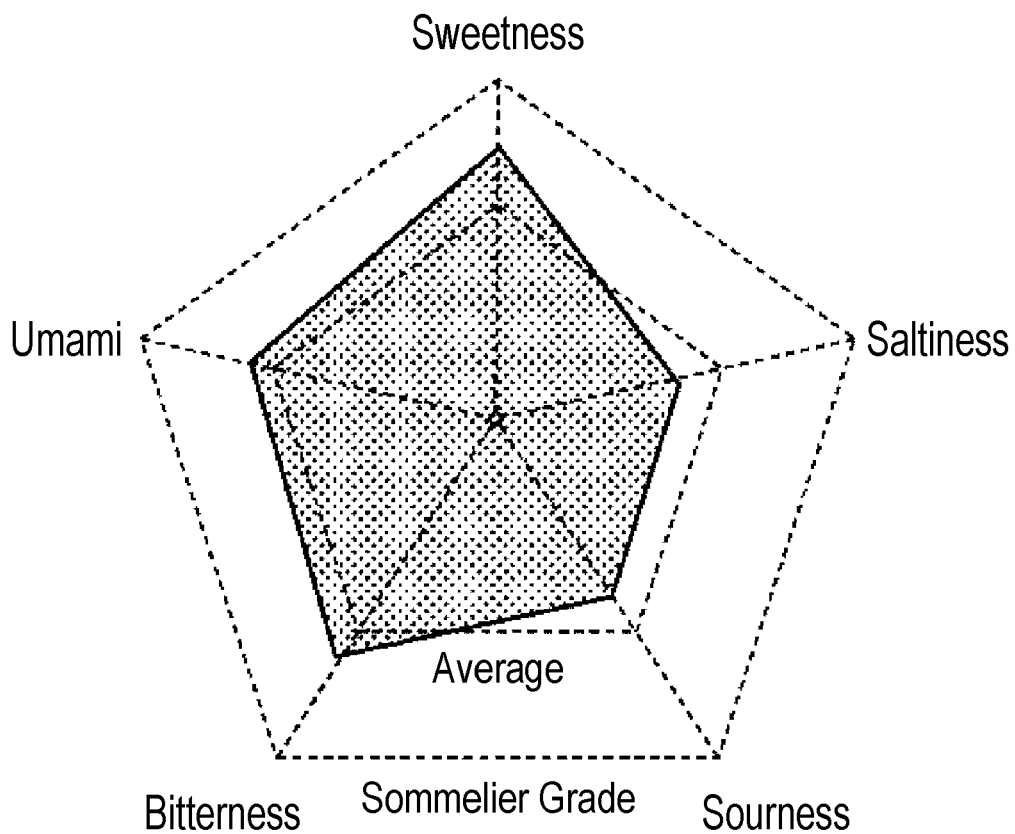
FIG. 8 is a view illustrating one example of sense-of-taste evaluation information displayed on the display of the communication terminal in the first embodiment.

FIG. 8 is a view illustrating one example of the sense-of-taste evaluation information displayed on the display of the communication terminal in the first embodiment.

The sense-of-taste evaluation information illustrated in FIG. 8 is displayed on the display 14 of the communication terminal 1. The sense-of-taste evaluation information includes an evaluation value (a sense-of-taste score) for the entire sense of taste including at least one type of taste component and a radar chart indicating evaluation values for the sense of taste of each of the at least one type of taste component. The sense-of-taste evaluation information is one example of the information indicating the evaluation values of the user's sense of taste.

For instance, in the case of an example of the taste resolution, the smaller the taste-level difference in the taste resolution is, the larger the points the evaluation value of the sense of taste is assigned. For example, when the taste-level difference is 2, 200 points is assigned, and when the taste-level difference is 4, 150 points is assigned.

The inside dashed line in the radar chart may represent average scores of all examinees of the taste resolution tests. Also, the inside dashed line in the radar chart may represent average scores of examinees of the taste resolution tests in the same age group as the user. An outside dashed line in the radar chart may represent sense-of-taste scores of a group of high-ranking people among examinees of the taste resolution tests. Also, the outside dashed line in the radar chart may represent average scores of a particular group of evaluators (such as qualified sommeliers, eating and drinking establishment proprietors, or chefs of hotel restaurants). Also, when the average scores of a particular group of evaluators are displayed, a sommelier grade, a proprietor grade of eating and drinking establishments, a chef grade of hotel restaurants, or the like may be displayed as an explanation of the outside dashed line in the radar chart so that the particular group of evaluators can be identified. The sense-of-taste score may be represented by level 1, level 2, level 3, or the like, not by points.

Similarly, the sense-of-taste score may be represented by a plurality of separate stages according to a unique criterion, not by points. In one example, the sense-of-taste score may be represented by a master sommelier grade, a senior sommelier grade, a sommelier grade, an assistant sommelier grade, a sommelier trainee grade, and so on. Additionally, the sense-of-taste score may be represented by a cook grade of a three-star restaurant, a cook grade of a two-star restaurant, a cook grade of a one-star restaurant, a cook grade of a restaurant in town, a domestic helper grade, and so on. Additionally, the sense-of-taste score may be represented by a first-class chef, a second-class chef, a third-class chef, a chef trainee, and so on. In addition, a scheme in which the sense-of-taste score is stepwise represented by characters in a novel, a comic, or the like may be used.

According to the first embodiment, in the measurement test of the taste resolution, what is the smallest distance the user can perceive between a plurality of levels with respect to at least one type of taste is measured, and based on the first data indicating the input values in the measurement test of the taste resolution, evaluation values of the user's sense of taste are generated in association with the user. Thus, it is possible to accurately and easily measure the user's sense of taste, and it is also possible to collect information regarding the user's sense of taste. In addition, the collected information regarding the sense of taste can also be used to provide new services, such as introduction of restaurants or dishes based on the sense of taste or health administration including dietary improvement instructions based on the sense of taste.

Subsequently, a description will be given of sense-of-taste evaluation processing in the management server in a first modification of the first embodiment.

In the first embodiment described above, the communication unit 21 in the management server 2 obtains the first data indicating input values in the measurement test of the taste resolution. In contrast, in the first modification of the first embodiment, the communication unit 21 in the management server 2 obtains, from the communication terminal 1, second data indicating input values in a measurement test of the user's taste sensing threshold (a measurement test of taste sensing). The measurement test of the taste sensing threshold is used to measure, among no taste and a plurality of levels ranging from a light taste to a strong taste of some kind of taste, at which level from no taste the user can sense a distinction as to whether there is no taste or any taste. The control unit 23 in the management server 2 then generates evaluation values of the user's sense of taste, based on at least the first data and the second data.

In the first modification of the first embodiment, the communication unit 21 transmits information on the measurement test of the taste sensing threshold to the communication terminal 1, the information being generated by the control unit 23. The communication unit 21 obtains the second data indicating input values in the measurement test of the user's taste sensing threshold, the input values being input using the operation unit 15 of the communication terminal 1. The communication unit 21 receives the second data transmitted by the communication terminal 1.

The "taste sensing threshold" indicates, when the amount of a specific taste component contained per test meal is increased gradually, a minimum amount of the taste component with which the user can perceive that the test meal is not tasteless. It has been known that the taste sensing threshold differs from one subject to another. It is also known that, even for the same subject, the taste sensing threshold differs for each taste component.

Based on the first data and second data received by the communication unit 21, the control unit 23 generates evaluation values of the user's sense of taste in association with the user. The control unit 23 registers information indicating the evaluation values in the memory 22. The communication unit 21 outputs the information indicating the evaluation values to the communication terminal 1 in order to display the information indicating the evaluation values on the display 14 of the communication terminal 1.

The input values in the measurement test of the taste sensing threshold are input at the operation unit 15 by using at least a first test meal group including a plurality of test meals corresponding to a plurality of levels ranging from a light sweet taste to a strong sweet taste, a second test meal group including a plurality of test meals corresponding to a plurality of levels ranging from a light salty taste to a strong salty taste, and a third test meal group including a plurality of tasteless test meals. The communication unit 21 outputs, to the communication terminal 1, a fourth instruction for making the user use the first test meal group and the third test meal group or the second test meal group and the third test meal group to input whether the test meals included in the first test meal group or the second test meal group are tasteless or not tasteless in order with a level of a lightest taste first. The communication unit 21 obtains second data as a response to the fourth instruction.

The first test meal group, the second test meal group, and the third test meal group are managed using a common test meal kit ID (identifier).

Also, in the first modification of the first embodiment, a test meal kit that is similar to that in the first embodiment is also used to perform the measurement test of the taste sensing threshold.

Figure 9:
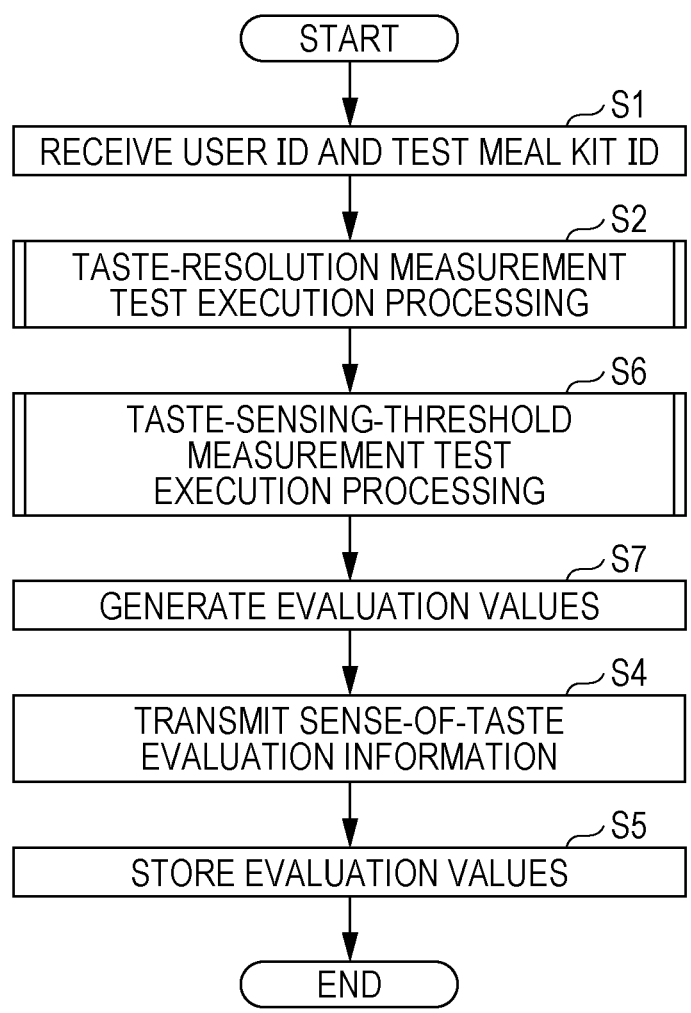
FIG. 9 is a flowchart illustrating sense-of-taste evaluation processing in the management server in a first modification of the first embodiment of the present disclosure.

FIG. 9 is a flowchart illustrating sense-of-taste evaluation processing in the management server in the first modification of the first embodiment of the present disclosure.

In FIG. 9, processes that are substantially the same as those in the sense-of-taste evaluation processing illustrated in FIG. 4 are denoted by the same reference numerals, and descriptions thereof will not be given hereinafter.

In step S6, the control unit 23 executes the taste-sensing-threshold measurement test execution processing. In the taste-sensing-threshold measurement test execution processing, the taste-sensing-threshold measurement test for measuring the taste sensing thresholds of the user are generated, and also second data indicating input values in the taste-sensing-threshold measurement test is obtained. The taste-sensing-threshold measurement test execution processing is described later with reference to FIG. 10.

In step S7 in FIG. 9, based on the first data and the second data, the control unit 23 generates evaluation values of the user's sense of taste in association with the user.

Subsequently, a description will be given of the taste-sensing-threshold measurement test execution processing in step S6 in FIG. 9.

Figure 10:
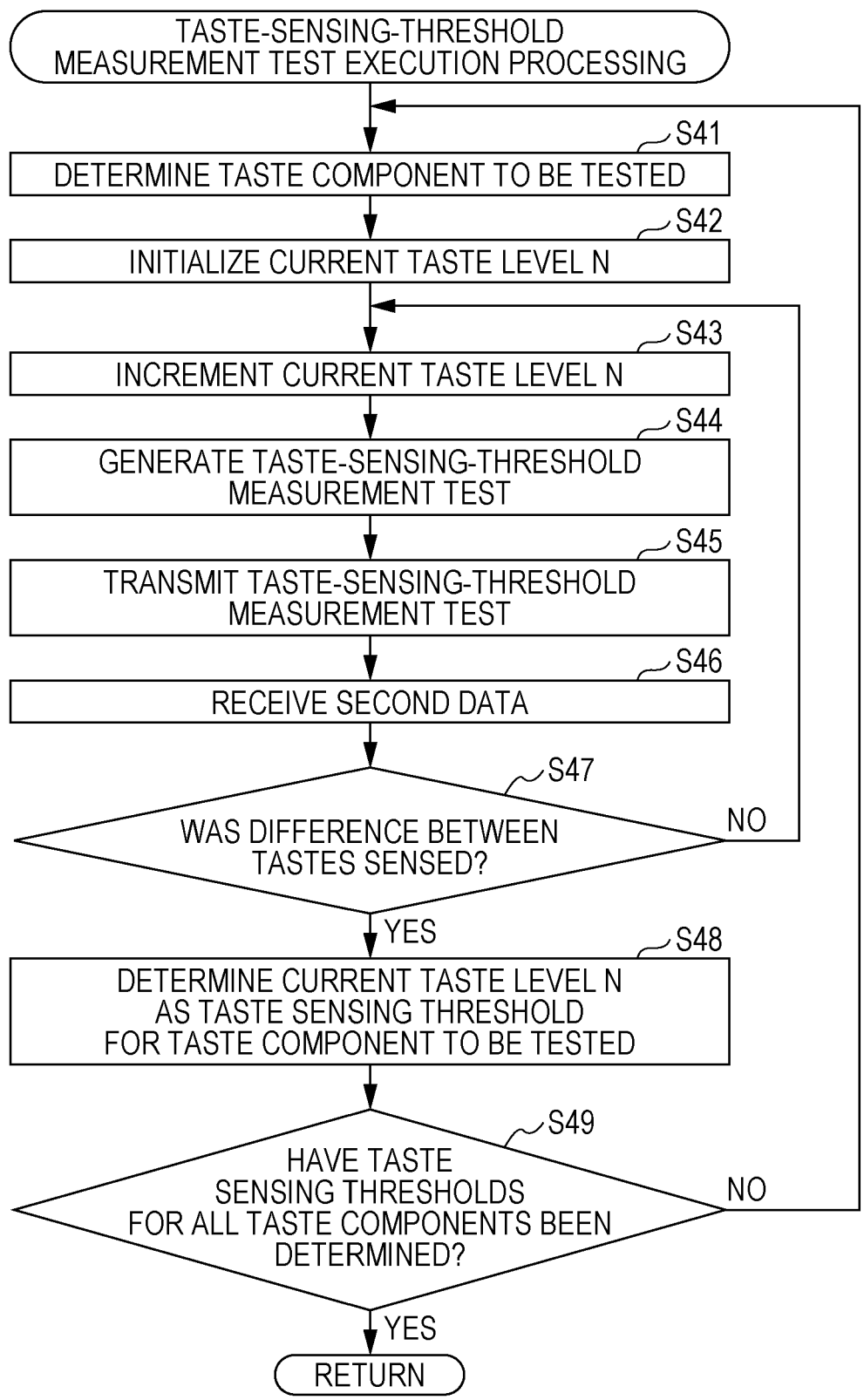
FIG. 10 is a flowchart illustrating taste-sensing-threshold measurement test execution processing in step S6 in FIG. 9.

FIG. 10 is a flowchart illustrating the taste-sensing-threshold measurement test execution processing in step S6 in FIG. 9.

First, in step S41, the control unit 23 determines a taste component to be tested. The control unit 23 determines an untested taste component of five taste components, that is, sweetness, saltiness, sourness, bitterness, and umami, as a taste component to be tested. In the first modification of the first embodiment, the control unit 23 measures a taste sensing threshold for each of the five taste components.

Next, in step S42, the control unit 23 initializes a current taste level N. The initialized taste level N is 0.

Next, in step S43, the control unit 23 increments the current taste level N.

Next, in step S44, the control unit 23 specifies a tasteless pill and a pill with the current taste level N of the taste component to be tested and generates a taste-sensing-threshold measurement test for obtaining an answer as to whether or not there is a difference between the tastes of the specified two pills.

For example, when a taste sensing threshold for sweetness is to be first tested, the control unit 23 tests whether or not the user can perceive a difference between the tastes of two pills, that is, a tasteless pill and a pill with sweetness level 1.

Next, in step S45, the communication unit 21 transmits the taste-sensing-threshold measurement test generated by the control unit 23 to the communication terminal 1. Then, the communication unit 11 in the communication terminal 1 receives the taste-sensing-threshold measurement test. The display 14 of the communication terminal 1 displays the taste-sensing-threshold measurement test received by the communication unit 11. In this taste-sensing-threshold measurement test, the user is prompted to eat the tasteless pill and the pill with the current taste level N to be tested, and an answer as to whether or not there is a difference between the tastes of the two pills is received. The two pills are specified by the pill IDs. The user eats the specified two pills and inputs whether or not there is a difference between the tastes of the two pills. The communication unit 11 transmits, to the management server 2, second data indicating the user's input value (an answer) with respect to the taste-sensing-threshold measurement test.

Next, in step S46, the communication unit 21 receives the second data transmitted by the communication terminal 1.

Next, in step S47, the control unit 23 decides whether or not the user sensed a difference between the tastes. When it is decided that the user did not sense a difference between the tastes (NO in step S47), the process returns to step S43.

On the other hand, when it is decided that the user sensed a difference between the tastes (YES in step S47), in step S48, the control unit 23 determines the current taste level N as a taste sensing threshold for the taste component to be tested.

For example, when the user fails to sense a difference between the taste of a tasteless pill and the taste of a pill with sweetness level 1, the control unit 23 tests whether or not the user can sense a difference between the taste of a tasteless pill and the taste of a pill with sweetness level 2. The control unit 23 then increments the sweetness level N of one of the two pills until the user can sense a difference between the tastes of the two pills and determines, as the taste sensing threshold for sweetness, the sweetness level N at which the user senses a taste difference for the first time.

Next, in step S49, the control unit 23 decides whether or not taste sensing thresholds for all the taste components have been determined. When it is decided that the taste sensing thresholds for all the taste components have not been determined (NO in step S49), the process returns to step S41.

On the other hand, when it is decided that the taste sensing thresholds for all the taste components have been determined (YES in step S49), the taste-sensing-threshold measurement test execution processing ends.

Figure 11:
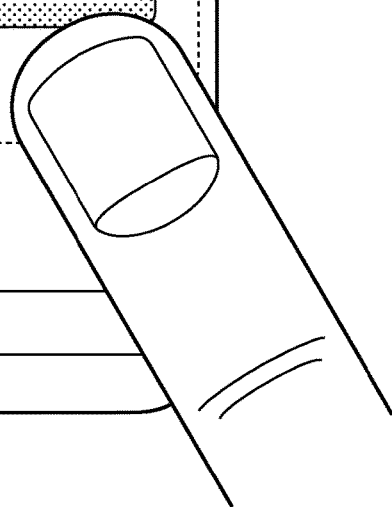
FIG. 11 is a view illustrating one example of a taste-sensing threshold test screen displayed on the display of the communication terminal in the first modification of the first embodiment.

FIG. 11 is a view illustrating one example of the taste-sensing threshold test screen displayed on the display of the communication terminal in the first modification of the first embodiment.

The display 14 of the communication terminal 1 displays the taste-sensing threshold test screen illustrated in FIG. 11. The taste-sensing threshold test screen includes the pill IDs of two pills that the user is to eat, a first answer button indicating that the two pills have the same taste, and a second answer button indicating that the two pills have different tastes. One of the two pills is a tasteless pill, and the other is a pill with the taste level N. The user eats the specified two pills and gives an answer as to whether or not the two pills have the same taste. When the user feels that the two pills have the same taste, he or she touches the first answer button. When the user feels that the two pills have different tastes, he or she touches the second answer button.

The control unit 23 converts the taste resolution for each taste component into points and also converts the taste sensing threshold for each taste component into points. The control unit 23 then totals the points of the taste resolution and the points of the taste sensing threshold for each taste component to calculate the total points for each taste component as an evaluation value for the taste component. In addition, the control unit 23 further totals the points for the taste components to thereby calculate an evaluation value for the entire sense of taste. The control unit 23 then generates sense-of-taste evaluation information that is similar to the sense-of-taste evaluation information illustrated in FIG. 8.

In the description given above in the first modification of the first embodiment in the present disclosure with reference to FIG. 9, the evaluation of the user's sense of taste is performed starting with two measurement tests of the taste resolution and the taste sensing threshold. However, the present disclosure is not limited to this, and the evaluation values of the user's sense of taste may be generated by performing only the taste-sensing-threshold measurement test (step S6) without performing the taste-resolution measurement test (step S2). In this case, in step S7, the control unit 23 converts the taste sensing threshold for each taste component into points. The control unit 23 then calculates the points of the taste sensing threshold for each taste component as the evaluation value for the taste component. In addition, the control unit 23 totals the points for the taste components to thereby calculate the evaluation value for the entire sense of taste. The control unit 23 then generates sense-of-taste evaluation information that is similar to the sense-of-taste evaluation information illustrated in FIG. 8. As described above, the evaluation of the user's sense-of-taste may be performed by using only the taste sensing threshold or by combining the taste resolution and the taste sensing threshold with respect to at least one taste component.

Subsequently, a description will be given of sense-of-taste evaluation processing in the management server in a second modification of the first embodiment.

In the first embodiment described above, the communication unit 21 in the management server 2 obtains the first data indicating input values in the measurement test of the taste resolution. In contrast, in the second modification of the first embodiment, the communication unit 21 in the management server 2 obtains, from the communication terminal 1, third data indicating input values in a measurement test of a taste recognition threshold (a measurement test of taste recognition) of the user. The measurement test of the taste recognition threshold is used to measure, among no taste and a plurality of levels ranging from a light taste to a strong taste of at least one type of taste, at which level from no taste the user can correctly recognize whether there is no taste or the least the one type of taste. The control unit 23 in the management server 2 then generates evaluation values of the user's sense of taste, based on at least the first data and the third data.

In this case, in the second modification of the first embodiment, the communication unit 21 transmits information on the measurement test of the taste recognition threshold, the information being generated by the control unit 23, to the communication terminal 1. The communication unit 21 obtains the third data indicating input values in the measurement test of the user's taste recognition threshold, the input value being input using the operation unit 15 of the communication terminal 1. The communication unit 21 receives the third data transmitted by the communication terminal 1.

The taste recognition threshold indicates, when the amount of a specific taste component contained per test meal is increased gradually, a minimum amount of taste component with which the user can perceive that the specific taste component is contained. It is known that the taste recognition threshold differs from one subject to another. It is also known that, even for the same subject, the taste recognition threshold differs for each taste component.

Based on the first data and third data received by the communication unit 21, the control unit 23 generates evaluation values of the user's sense of taste in association with the user. The control unit 23 registers information indicating the evaluation values in the memory 22. The communication unit 21 outputs the information indicating the evaluation values to the communication terminal 1 in order to display the information indicating the evaluation values on the display 14 of the communication terminal 1.

The input values in the measurement test of the user's taste recognition threshold are input at the operation unit 15 by using at least a first test meal group including a plurality of test meals corresponding to a plurality of levels ranging from a light sweet taste to a strong sweet taste and a second test meal group including a plurality of tasteless test meals. The communication unit 21 outputs, to the communication terminal 1, a fifth instruction for making the user uses the first test meal group and the second test meal group to input whether the test meals included in the first test meal group have no taste or have sweet taste in order with the level of a lightest sweet taste first. The communication unit 21 obtains the third data as a response to the fifth instruction.

The first test meal group and the second test meal group are managed using a common test meal kit ID (identifier).

In the second modification of the first embodiment, the measurement test of the taste recognition threshold is also performed using a test meal kit that is the same as or similar to that in the first embodiment.

Figure 12:
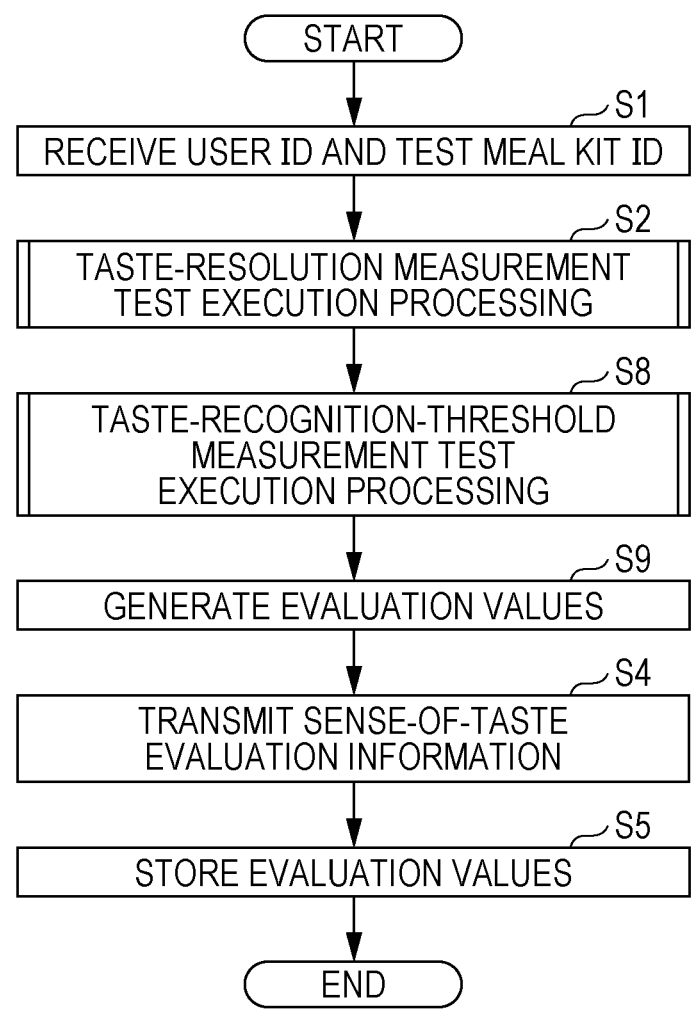
FIG. 12 is a flowchart illustrating sense-of-taste evaluation processing in the management server in a second modification of the first embodiment of the present disclosure.

FIG. 12 is a flowchart illustrating the sense-of-taste evaluation processing in the management server in the second modification of the first embodiment of the present disclosure.

In FIG. 12, processes that are substantially the same as those in the sense-of-taste evaluation processing illustrated in FIG. 4 are denoted by the same reference numerals, and descriptions thereof will not be given hereinafter.

In step S8, the control unit 23 executes taste-recognition-threshold measurement test execution processing. In the taste-recognition-threshold measurement test execution processing, a taste-recognition-threshold measurement test for measuring the user's taste recognition threshold is generated, and also the third data indicating input values in the taste-recognition-threshold measurement test is obtained. The taste-recognition-threshold measurement test execution processing is described later with reference to FIG. 13.

In step S9, based on the first data and the third data, the control unit 23 generates evaluation values of the user's sense of taste in association with the user.

Subsequently, a description will be given of the taste-recognition-threshold measurement test execution processing in step S8 in FIG. 12.

Figure 13:
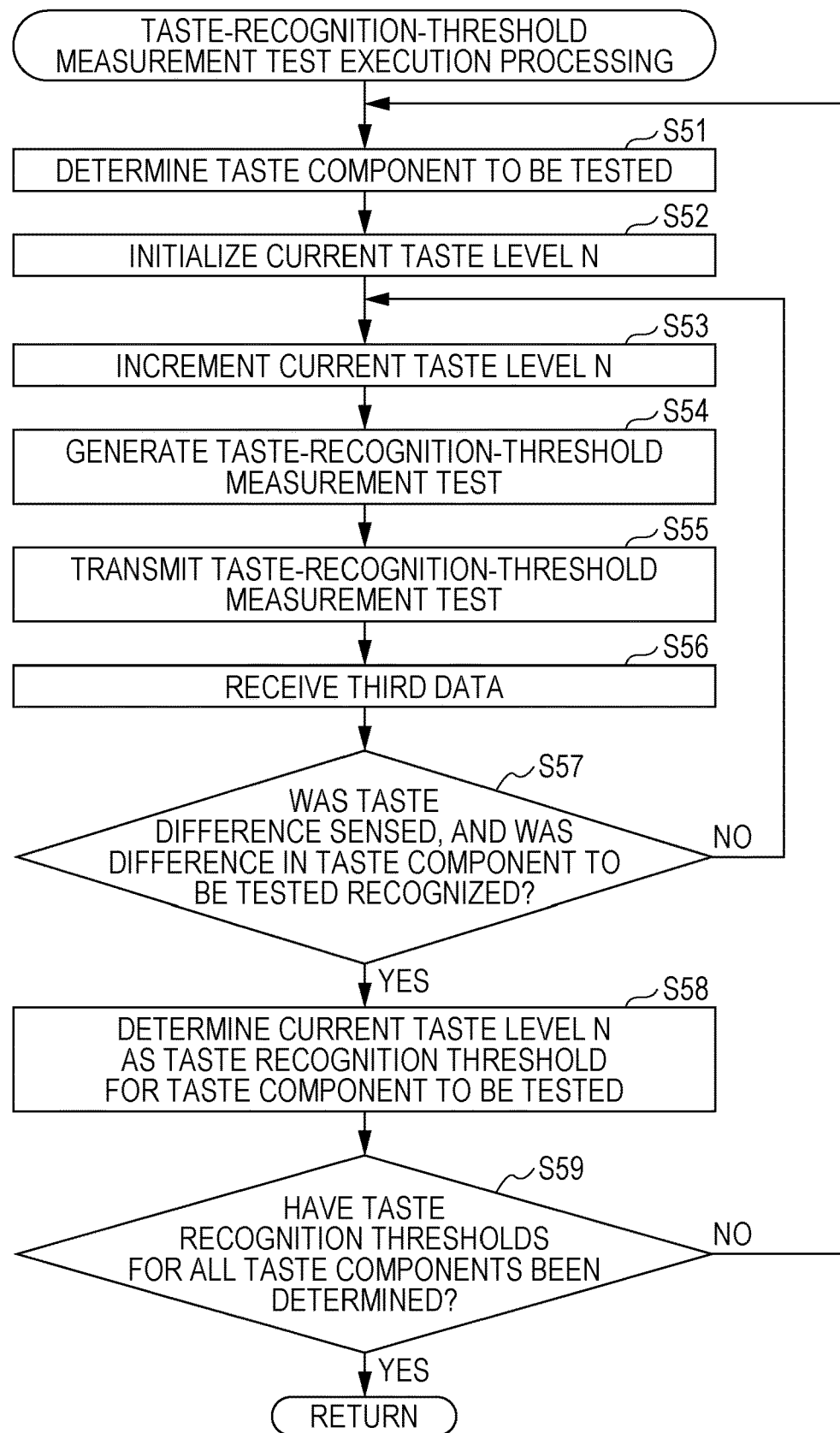
FIG. 13 is a flowchart illustrating taste-recognition-threshold measurement test execution processing in step S8 in FIG. 12.

FIG. 13 is a flowchart illustrating the taste-recognition-threshold measurement test execution processing in step S8 in FIG. 12.

First, in step S51, the control unit 23 determines a taste component to be tested. The control unit 23 determines an untested taste component of five taste components, that is, sweetness, saltiness, sourness, bitterness, and umami, as a taste component to be tested. In the second modification of the first embodiment, the control unit 23 measures a taste recognition threshold for each of the five taste components.

Next, in step S52, the control unit 23 initializes the current taste level N. The initialized taste level N is 0.

Next, in step S53, the control unit 23 increments the current taste level N.

Next, in step S54, the control unit 23 generates a taste-recognition-threshold measurement test in which a tasteless pill and a pill with the current taste level N of the taste component to be tested are specified and that is used for obtaining an answer as to whether or not there is a taste difference between the specified two pills and an answer as to what the taste component to be tested is.

For example, when a taste recognition threshold for sweetness is to be first tested, the control unit 23 tests whether or not the user can perceive a difference between the tastes of two pills, that is, a tasteless pill and a pill with sweetness level 1, and also tests whether or not the user can perceive the different taste component is sweetness.

Next, in step S55, the communication unit 21 transmits the taste-recognition-threshold measurement test generated by the control unit 23 to the communication terminal 1. The communication unit 11 in the communication terminal 1 then receives the taste-recognition-threshold measurement test. The display 14 of the communication terminal 1 displays the taste-recognition-threshold measurement test received by the communication unit 11. In the taste-recognition-threshold measurement test, the user is prompted to eat the tasteless pill and the pill with the current taste level N to be tested, an answer as to whether or not there is a difference between the tastes of the two pills is received, and an answer as to what the different taste component is when there is a difference is also received. The two pills are specified by the pill IDs. The user eats the specified two pills and inputs whether or not there is a difference between the tastes of the two pills and what the different taste component is when there is a difference. The communication unit 11 transmits, to the management server 2, third data indicating the user's input value (answer) with respect to the taste-recognition-threshold measurement test.

Next, in step S56, the communication unit 21 receives the third data transmitted by the communication terminal 1.

Next, in step S57, the control unit 23 decides whether or not the user sensed a taste difference and recognized that the taste component to be tested is different. When it is decided that the user did not sense a taste difference or did not recognize that the taste component to be tested is different (NO in step S57), the process returns to step S53.

On the other hand, when it is decided that the user sensed a taste difference and correctly recognized that the taste component to be tested is different (YES in step S57), in step S58, the control unit 23 determines the current taste level N as a taste recognition threshold for the taste component to be tested.

For example, when the user failed to sense a taste difference between a tasteless pill and a pill with sweetness level 1, the control unit 23 tests whether or not the user can sense a taste difference between a tasteless pill and a pill with sweetness level 2. Also, even when the user successfully sensed a taste difference between the tasteless pill and the pill with sweetness level 1, when the user failed to correctly recognize that the different taste component to be tested is sweetness, the control unit 23 tests whether or not the user can sense a taste difference between a tasteless pill and a pill with sweetness level 2. Then, the control unit 23 increments the sweetness level N of one of the two pills until the user can sense a taste difference between the pills and also can recognize that the different taste component to be tested is sweetness and determines, as the taste recognition threshold for sweetness, the sweetness level N at which the user recognizes for the first time that the taste component to be tested is sweetness.

Next, in step S59, the control unit 23 decides whether or not taste recognition thresholds for all the taste components have been determined. When it is decided that the taste recognition thresholds for all the taste components have not been determined (NO in step S59), the process returns to step S51.

On the other hand, when it is decided that the taste recognition thresholds for all the taste components have been determined (YES in step S59), the taste-recognition-threshold measurement test execution processing ends.

Figure 14:
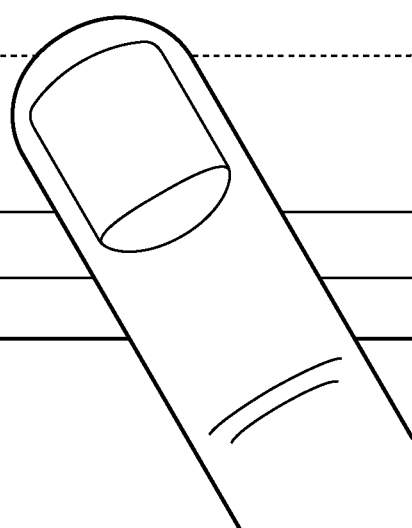
FIG. 14 is a view illustrating one example of taste-sensing threshold test screen displayed on the display of the communication terminal in the second modification of the first embodiment.

FIG. 14 is a view illustrating one example of a taste recognition threshold test screen displayed on the display of the communication terminal in the second modification of the first embodiment.

The display 14 of the communication terminal 1 displays the taste recognition threshold test screen illustrated in FIG.

14. When it is clearly specified that one of two pills is tasteless, the taste recognition threshold test screen includes the pill IDs of two pills that the user is to eat, a first answer button indicating that the two pills have the same taste, a second answer button indicating that one of the two pills contains a sweet taste component, a third answer button indicating that one of the two pills contains a sourness taste component, a fourth answer button indicating that one of two pills contains an umami taste component, a fifth answer button indicating that one of the two pills contains a saltiness taste component, and a sixth answer button indicating that one of the two pills contains a bitterness taste component. One of the two pills is a tasteless pill, and the other is a pill with taste level N.

When it is not clearly specified that one of two pills is tasteless, the taste recognition threshold test screen includes the pill IDs of two pills that the user is to eat, a first answer button indicating that the two pills have the same taste, a second answer button indicating that the two pills are different in amount of a sweet taste component, a third answer button indicating that the two pills are different in amount of a sourness taste component, a fourth answer button indicating that the two pills are different in amount of an umami taste component, a fifth answer button indicating that the two pills are different in amount of a saltiness taste component, and a sixth answer button indicating that the two pills are different in amount of a bitterness taste component. The two pills may be pills that are not tasteless or may be pills that are different from each other in amount of the contained taste component to be tested and that are equal to each other in amount of other taste components.

The user eats the specified two pills and answers whether or not the two pills have the same taste, and when the two pills do not have the same taste, the user answers what the contained or different taste component is. When the user feels that the two pills have the same taste, the user touches the first answer button. When the user feels that the two pills have different tastes, the user touches one of the second to sixth answer buttons. The taste-sensing-threshold measurement test can also be performed in parallel with the taste-recognition-threshold measurement test. In this case, the taste recognition threshold test screen may further display a seventh answer button that is selected when the user understands that the tastes of the two pills are different from each other but does not understand what the different taste component thereof is. This makes it possible to carry out two or more measurement tests regarding the sense of taste, including the taste-sensing-threshold measurement test and the taste-recognition-threshold measurement test, and thus the evaluation of the user's sense of taste can be efficiently performed with a small number of rounds of testing.

The control unit 23 converts the taste resolution for each taste component into points and also converts the taste recognition threshold for each taste component into points. The control unit 23 totals the points of the taste resolution and the points of the taste recognition threshold for each taste component to calculate the total points for each taste component as an evaluation value for the taste component. In addition, the control unit 23 further totals the points for the taste components to thereby calculate an evaluation value for the entire sense of taste. Then, the control unit 23 generates sense-of-taste evaluation information that is similar to the sense-of-taste evaluation information illustrated in FIG. 8.

In the description given above in the second modification of the first embodiment in the present disclosure with reference to FIG. 12, the evaluation of the user's sense of taste are performed starting with the two measurement tests for the taste resolution and the taste recognition threshold. However, the present disclosure is not limited to that described above, and the evaluation values of the user's sense of taste may be generated by performing only the taste-recognition-threshold measurement test (step S8) without performing the taste-resolution measurement test (step S2). In this case, in step S9, the control unit 23 converts the taste recognition threshold for each taste component into points. The control unit 23 then calculates the points of the taste recognition threshold for each taste component as an evaluation value for the taste component. In addition, the control unit 23 further totals the points for the taste components to thereby calculate an evaluation value for the entire sense of taste. Then, the control unit 23 generates sense-of-taste evaluation information that is similar to the sense-of-taste evaluation information illustrated in FIG. 8. As described above, the evaluation of the user's sense of taste may be made with only the taste recognition threshold with respect to at least one taste component. Alternatively, the evaluation of the user's sense of taste may be made by combining at least two of the taste resolution (the first data), the taste sensing threshold (the second data), and the taste recognition threshold (the third data) with respect to at least one taste component.

Subsequently, a description will be given of sense-of-taste evaluation processing in the management server in a third modification of the first embodiment.

In the first embodiment described above, the communication unit 21 in the management server 2 obtains the first data indicating the input values in the measurement test of the taste resolution. In contrast, in the third modification of the first embodiment, the communication unit 21 in the management server 2 obtains, from the communication terminal 1, fourth data indicating input values in a measurement test of the taste density of the user. The measurement test of the taste density is used in order to measure whether the user can relatively correctly recognize at least three levels ranging from a light taste to a strong taste with respect to at least one type of taste. The control unit 23 in the management server 2 generates evaluation values of the user's sense of taste, based on at least the first data and the fourth data.

In the third modification of the first embodiment, the communication unit 21 transmits information regarding a taste-density measurement test, generated by the control unit 23, to the communication terminal 1. The communication unit 21 obtains fourth data indicating input values in the measurement test of the taste density of the user, the input value being input using the operation unit 15 of the communication terminal 1. The communication unit 21 receives the fourth data transmitted by the communication terminal 1.

Based on the first data and fourth data received by the communication unit 21, the control unit 23 generates evaluation values of the user's sense of taste in association with the user. The control unit 23 registers information indicating the evaluation values in the memory 22. The communication unit 21 outputs the information indicating the evaluation values to the communication terminal 1 in order to display the information indicating the evaluation values on the display 14 of the communication terminal 1.

The input value in the measurement test of taste density of the user is input at the operation unit 15, for example, by using at least a first test meal group including a plurality of test meals corresponding to a plurality of levels ranging from a light sweet taste to a strong sweet taste. The communication unit 21 outputs, to the communication terminal 1, a sixth instruction for making the user use the first test meal group and input, in order of density of taste, at least three test meals of the test meals included in the first test meal group. The communication unit 21 obtains the fourth data as a response to the sixth instruction.

In the third modification of the first embodiment, the measurement test of the taste density is also performed using a test meal kit that is the same as or similar to that in the first embodiment.

Figure 15:
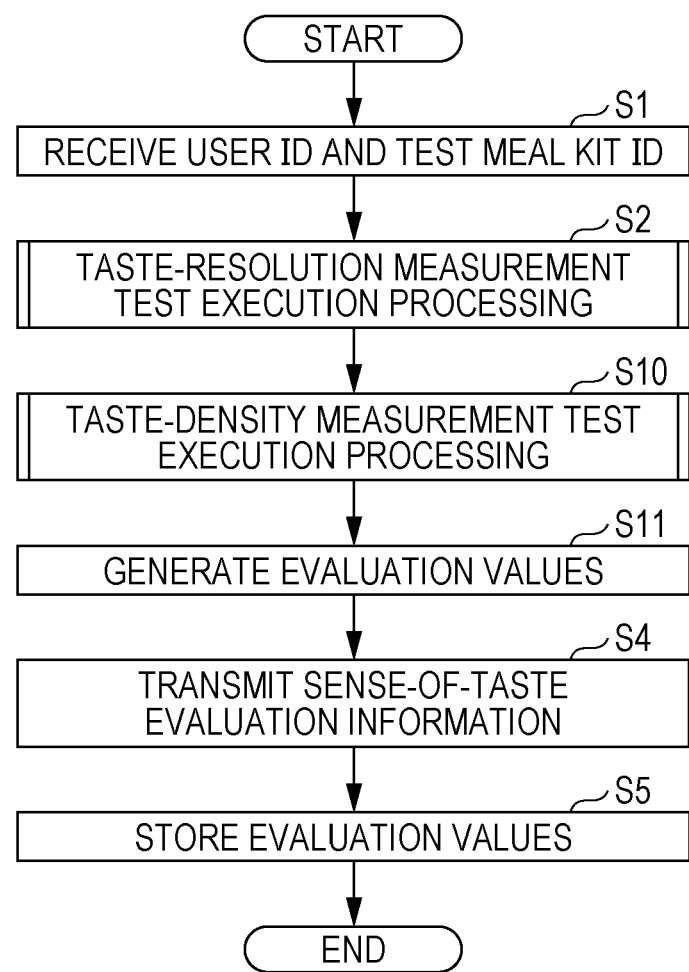
FIG. 15 is a flowchart illustrating sense-of-taste evaluation processing in the management server in a third modification of the first embodiment of the present disclosure.

FIG. 15 is a flowchart illustrating the sense-of-taste evaluation processing in the management server in the third modification of the first embodiment of the present disclosure.

In FIG. 15, processes that are substantially the same as those in the sense-of-taste evaluation processing illustrated in FIG. 4 are denoted by the same reference numerals, and descriptions thereof will not be given hereinafter.

In step S10, the control unit 23 executes taste-density measurement test execution processing. In the taste-density measurement test execution processing, a taste-density measurement test for measuring the taste density of the user is generated, and also the fourth data indicating input values in the taste-density measurement test is obtained. The taste-density measurement test execution processing is described later with reference to FIGS. 16 and 17.

In step S11 in FIG. 15, based on the first data and the fourth data, the control unit 23 generates evaluation values of the user's sense of taste in association with the user.

Subsequently, a description will be given of the taste-density measurement test execution processing in step S10 in FIG. 15.

First, the control unit 23 determines a taste component to be tested. The control unit 23 determines an untested taste component of five taste components, that is, sweetness, saltiness, sourness, bitterness, and umami, as a taste component to be tested. In the third modification of the first embodiment, the control unit 23 measures a taste density for each of the five taste components.

Next, the control unit 23 selects, for example, four taste levels from among the currently remaining taste levels.

Next, the control unit 23 specifies pills with the four taste levels of the taste component to be tested and generates a taste-density measurement test for obtaining an answer as to the specified four pills that the user arranged in descending order of taste density.

For example, when a taste density for bitterness is to be first tested, the control unit 23 makes the user arrange pills with bitterness levels 3, 5, 7, and 9 in descending order of taste density.

Next, the communication unit 21 transmits the taste-density measurement test, generated by the control unit 23, to the communication terminal 1. The communication unit 11 in the communication terminal 1 then receives the taste-density measurement test. The display 14 of the communication terminal 1 displays the taste-density measurement test received by the communication unit 11. In this taste-density measurement test, the user is prompted to eat the pills with the four taste levels to be tested, and an answer as to the four pills arranged in descending order of taste density is received. The four pills are specified by the pill IDs. The user eats the specified four pills and arranges the four pills in descending order of taste density. The communication unit 11 transmits the fourth data indicating the user's input values (answer) with respect to the taste-density measurement test to the management server 2.

Figure 16:
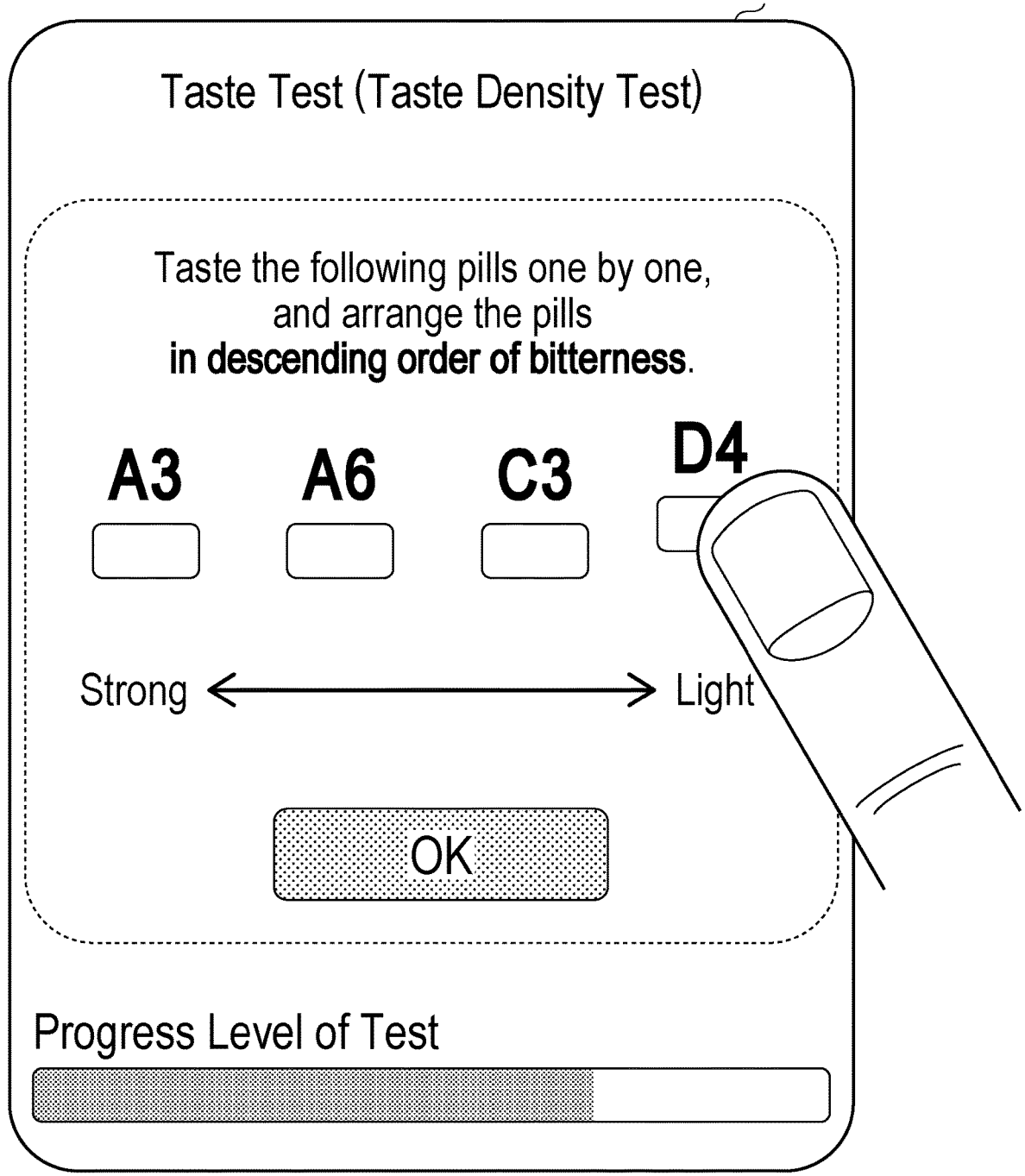
FIG. 16 is a view illustrating one example of a taste-density test screen displayed on the display of the communication terminal in the third modification of the first embodiment.

FIG. 16 is a view illustrating one example of a taste-density test screen displayed on the display of the communication terminal in the third modification of the first embodiment.

The display 14 of the communication terminal 1 displays the taste-density test screen illustrated in FIG. 16. The taste-density test screen includes icons representing the pill IDs of four pills that the user is to eat and an OK button for finalizing the order of the icons arranged in descending order of taste density. The positions of the four icons can be changed. The user arranges the four icons in descending order of density of a specified taste.

The user eats the specified four pills and arranges the icons representing the four pills in descending order of bitterness. Upon finishing arranging the four icons, the user touches the OK button.

Next, the communication unit 21 receives the fourth data transmitted by the communication terminal 1.

Next, the control unit 23 calculates an amount of difference between the order of the icons arranged by the user and an order in a correct answer.

Next, the control unit 23 decides whether or not a taste test can be generated using the remaining pills. The control unit 23 generates a taste test having higher difficulty, when the amount of difference is small, and generates a taste test having lower difficulty, when the amount of difference is large. For example, the smaller the taste-level difference of the pills is, the higher the difficulty becomes, and the larger the taste-level difference of the pills is, the lower the difficulty becomes.

In this case, when it is decided that a taste-density measurement test can be generated using the remaining pills, and a next taste-density measurement test is needed, the control unit 23 generates the taste-density measurement test.

On the other hand, when it is decided that a taste density test cannot be generated using the remaining pills, or when it is decided that a next taste-density measurement test is not needed, the control unit 23 determines the current amount of difference as a taste density of the taste component to be tested.

Next, the control unit 23 decides whether or not the taste densities of all the taste components have been determined. Upon deciding that the taste densities of all the taste components have not been determined, the control unit 23 determines an untested taste component as the taste component to be tested.

On the other hand, when it is decided that the taste densities of all the taste components have been determined, the taste-density measurement test execution processing ends.

FIG. 17 is a table illustrating one example of the order in the correct answer, the order in the user's answer, and an amount of difference therebetween in the third modification of the first embodiment.

The control unit 23 totals the values of squares of differences between ranks in the correct answer and ranks in the user's answer for respective pills to thereby calculate an amount of difference between the order in the user's answer and the order in the correct answer.

In the example illustrated in FIG. 17, the order in the correct answer is pill A3, pill D4, pill C3, and pill A6, and the order in the user's answer is pill A3, pill A6, pill C3, and pill D4. In this case, the control unit 23 calculates the amount of difference as in:

$$\text{Amount of Difference} = (1-1)^2 + (4-2)^2 + (3-3)^2 + (2-4)^2 = 8.$$

In accordance with the magnitude of the calculated amount of difference, the control unit 23 changes the difficulty of a subsequent sense-of-taste measurement test or determines the evaluation value of the taste density.

For example, as the amount of difference becomes larger, the difficulty of the next taste-density measurement test and/or another sense-of-taste measurement test decrease more significantly. Also, when the amount of difference becomes smaller, the difficulty of the next taste-density measurement test and/or another sense-of-taste measurement test decreases (increases) less significantly. That is, when it is assumed that the amount of difference is $Xn$, and the difficulty of the next taste-density measurement test and/or another sense-of-taste measurement test decreases by $Yn$, $Y1 > Y2$ holds for $X1 > X2$. Although $Xn > 0$ always holds, $Yn$ is positive or negative. When the difficulty of the next taste-density measurement test and/or another sense-of-taste measurement test increases, $Yn$ becomes a negative number.

The next taste-density measurement test is generated using pills that remain at the current point in time. For example, when only pills with four sweetness levels 1, 2, 4, and 8 remain, a taste-density measurement test for a taste-level difference of 1, 2, 3, 4, 6, or 7 can be executed, but a taste-density measurement test for any other taste-level difference cannot be executed. Based on a set difficulty of the next taste-density measurement test and a combination of the taste levels of the remaining pills, the control unit 23 determines content of the next taste-density measurement test and/or another sense-of-taste measurement test and two or more pills used in the measurement test.

Also, when the amount of difference becomes larger, the score (the evaluation value) of the taste-density measurement test increases (or decreases) less significantly. Also, when the amount of difference becomes smaller, the score increases more significantly. It can be said that the higher the score of the taste-density measurement test is, the more sensitive the sense of taste is. That is, when it is assumed that the amount of difference is $Xn$, and the score of the taste-density measurement test increases by $Zn$, $Z1 < Z2$ holds for $X1 > X2$. Although $Xn > 0$ always holds, $Zn$ is positive or negative. When the score decreases, $Zn$ becomes a negative number.

The control unit 23 generates a score (an evaluation value) of the taste-density measurement test in accordance with the magnitude of the amount of difference. The control unit 23 reduces the score as the amount of difference increases and increases the score as the amount of difference decreases.

The control unit 23 converts the taste resolution for each taste component into points and also converts the taste density for each taste component into points. The control unit 23 then totals the points of the taste resolution and the points of the taste density for each taste component to calculate the total points for each taste component as an evaluation value for the taste component. In addition, the control unit 23 further totals the points for the taste components to calculate an evaluation value for the entire sense of taste. Then, the control unit 23 generates sense-of-taste evaluation information that is similar to the sense-of-taste evaluation information illustrated in FIG. 8.

In the description given above in the third modification of the first embodiment in the present disclosure with reference to FIG. 15, the evaluation of the user's sense of taste is performed starting with two measurement tests of the taste resolution and the taste density. However, the present disclosure is not limited to this, and the control unit 23 may be adapted to generate the evaluation values of the user's sense of taste by performing only the taste-density measurement test (step S10) without performing the taste-resolution measurement test (step S2). In this case, in step S11, the control unit 23 converts the taste density for each taste component into points. The control unit 23 then calculates the points of the taste density for each taste component as the evaluation value for the taste component. In addition, the control unit 23 further totals the points for the taste components to thereby calculate an evaluation value for the entire sense of taste. Then, the control unit 23 generates sense-of-taste evaluation information that is similar to the sense-of-taste evaluation information illustrated in FIG. 8. As described above, the evaluation of the user's sense of taste may be performed with only the taste density with respect to at least one taste component. Alternatively, the evaluation of the user's sense of taste may be performed by combining at least two of the taste resolution (the first data), the taste sensing threshold (the second data), the taste recognition threshold (the third data), and the taste density (the fourth data) with respect to at least one taste component.

Subsequently, a description will be given of sense-of-taste evaluation processing in the management server in a fourth modification of the first embodiment.

In the fourth modification of the first embodiment, only a predetermined test meal is used to perform a measurement test regarding the user's sense of taste. The test meal used in the fourth modification of the first embodiment contains at least one type of taste component. The user tastes one test meal to be tested and individually answers whether or not he or she feels taste with respect to each of the five types of taste. Based on whether the answer is correct or incorrect or the amount of difference from a correct answer, the control unit 23 calculates an evaluation value of the user's taste sensitivity.

FIG. 18 is a view illustrating one example of a taste-mixture test screen displayed on the display of the communication terminal in the fourth modification of the first embodiment. FIG. 19 is a table illustrating one example of a table in which the amount of each taste component contained in the test meal, a result of the user's answer with respect to the taste component, and a score for the taste component are associated with each other in the fourth modification of the first embodiment. FIG. 20 is a table illustrating one example of a table in which the amount of each taste component contained, points added when the answer is a correct answer, and points added when the answer is an incorrect answer are associated with each other in the fourth modification of the first embodiment.

For example, pill E3 contains an amount of a taste component corresponding to sweetness level 2, an amount of a taste component corresponding to saltiness level 3, and an amount of a taste component corresponding to sourness level 1. Also, pill E3 does not contain taste components corresponding to bitterness and umami. In the table illustrated in FIG. 19, the bitterness level and the umami level are shown as 0. The taste test in the fourth modification of the first embodiment measures taste sensitivities to a plurality of taste components at the same time.

The taste-mixture test screen illustrated in FIG. 18 is displayed on the display 14 of the communication terminal 1. The taste-mixture test screen includes a pill ID of one pill that the user is to eat and checkboxes for receiving the user's answers as to whether or not the pill contains respective taste components of sweetness, saltiness, sourness, bitterness, and umami. The user eats a specified pill and answers whether or not the pill contains the respective taste components of sweetness, saltiness, sourness, bitterness, and umami. When the user feels that the pill does not contain a sweet taste component, he or she touches a checkbox corresponding to "Absent". Also, when the user feels that the pill contains a sweet taste component, he or she touches a checkbox corresponding to "Present". The user answers whether or not the pill contains each of all the taste components.

In the taste-mixture test screen illustrated in FIG. 18, the user is requested to give an answer as to the presence/absence of each taste in pill E3. In response to the request, the user who tastes pill E3 inputs answers as to the presence/absence of five types of taste, in other words, five types of taste component, via the operation unit 15 of the communication terminal 1.

In this case, with respect to each of the five types of taste, based on the taste level thereof, that is, the amount of the contained taste component thereof, the control unit 23 adds points corresponding to the correct answer or the incorrect answer of the user's answer, as illustrated in FIG. 20.

For example, when the pill eaten by the user does not contain a certain taste component (when the taste level thereof is 0), and the user gives a correct answer, that is, an answer indicating that the taste component is not contained, 0 point is added to the evaluation point for the sense of taste, and when the user gives an incorrect answer, that is, an answer indicating that the taste component is contained, minus 2 points is added to the evaluation point for the sense of taste as a penalty.

In addition, when the pill eaten by the user contains a taste component (when the taste level is 1 or higher), and the user gives a correct answer, that is, an answer indicating that the taste component is contained, larger points (e.g., 4 points) is added for a lower taste level, and smaller points (e.g., 1 point) is added for a higher taste level. In addition, when the pill eaten by the user contains a taste component (when the taste level is 1 or higher), and the user gives an incorrect answer, that is, an answer indicating that the taste component is not contained, smaller negative points (e.g., minus 1 point) is added for a lower taste level, and larger negative points (e.g., minus 4 points) is added for a higher taste level. Changing evaluation points to be added depending on whether the amount of the taste component contained is large (the level of taste is high) or the amount of the taste component contained is small (the level of taste is low) for each type of taste, as described above, makes it possible to perform more accurate evaluation.

In the example illustrated in FIG. 19, since the user's answer with respect to sweetness level 2 is an incorrect answer, minus 2 points is added as evaluation points for sweetness. In the same manner, since the user's answer with respect to saltiness level 3 is a correct answer, 2 points is added as evaluation points for saltiness. Likewise, 4 points, 0 point, and minus 2 points are also added with respect to sourness, bitterness, and umami, respectively. These evaluation points are exemplary and may have values different from the evaluation values in this example.

As described above, in the measurement test of the taste sensitivity in the fourth modification of the first embodiment, the user is made to give answers as to the presence/absence of the five types of taste component at a time with respect to one test meal containing a predetermined amount or more (level 1 or higher) of at least one type of taste component. This allows the five types of taste sensitivity to be quantitatively measured at the same time. Accordingly, performing a predetermined number of taste tests (taste mixture tests) by using a predetermined amount of test meal makes it possible to accurately measure the user's taste sensitivity.

Also, since the number of test meals used in the taste test is reduced, and the number of taste tests is reduced, there are advantages that not only the cost is reduced but also the user's burden is reduced. In the first embodiment, the identification information (the ID and/or the two-dimensional code) given to the test meal kit is the same as in FIG. 2, and pieces of identification information (the pill IDs) given to the individual test meals may be numerals, such as 1, 2, and 3, according to the order of tests. In the fourth modification of the first embodiment as well as in the first embodiment described above, types of taste component contained in one test meal and the amount of each taste component can be identified by a practitioner of the measurement test by using identification information (the common identifier) given to the test meal kit and identification information (the individual identifiers) given to the test meals therein.

The measurement test regarding the sense of taste in the fourth modification of the first embodiment of the present disclosure may be performed, for example, as step S2 in FIG. 4.

At least one of the measurement test of the taste resolution in the first embodiment, the measurement test of the taste sensing threshold in the first modification of the first embodiment, the measurement test of the taste recognition threshold in the second modification of the first embodiment, the measurement test of the taste density in the third modification of the first embodiment, and the measurement test of the taste mixture in the fourth modification of the first embodiment may be performed as step S2.

Also, although, in the first embodiment, the information management system includes the communication terminal 1 and the management server 2, the present disclosure is not particularly limited thereto. The information management system may include only the communication terminal 1, and the communication terminal 1 may have the functions of the management server 2. In this case, the communication terminal 1 executes the processes in steps S2 to S5 in FIG. 4.

Second Embodiment

An information management system in a second embodiment provides a dish search screen. One search filter for filtering dishes or restaurants by using rating results of dishes or restaurants rated by sense-of-taste top scorers is provided on the dish search screen as one of a plurality of search filters.

The configuration of the information management system in the second embodiment is substantially the same as the configuration of the information management system in the first embodiment illustrated in FIG. 1. Thus, the configuration of the information management system in the second embodiment will be described with reference to FIG. 1.

The display 14 of the communication terminal 1 displays a dish search screen. One search filter for filtering dishes or restaurants by using rating results of dishes or restaurants rated by sense-of-taste top scorers is provided on the dish search screen as one of the search filters.

The operation unit 15 receives a user's rating of a dish or a restaurant. The operation unit 15 also receives the user's selection of one search filter via the dish search screen.

The communication unit 11 transmits, to the management server 2, rating information indicating the user's rating of a dish or a restaurant. Also, the communication unit 11 transmits a command indicating that one search filter is selected to the management server 2.

The communication unit 21 in the management server 2 obtains, from the communication terminal 1 through the network 3, first data indicating input values in a measurement test regarding the sense of taste of the user of the communication terminal 1. The measurement test regarding the sense of taste is used in order to measure the user's taste sensitivity to at least one type of taste.

The measurement test regarding the sense of taste in the second embodiment may be performed in the same manner as the measurement test regarding the sense of taste described above in the first embodiment.

Also, the communication unit 21 obtains rating information indicating the user's rating of a dish or a restaurant from the communication terminal 1. In addition, the communication unit 21 obtains, from the communication terminal 1 through the network 3, a command indicating that one search filter is selected.

Based on the first data, the control unit 23 may also generate evaluation values of the user's sense of taste in association with the user.

When the evaluation values of the user's sense of taste satisfy a certain condition for the sense-of-taste top scorers, the rating information indicating the user's rating of the dish or the restaurant is included in rating results of dishes or restaurants rated by the sense-of-taste top scorers. The sense-of-taste top scorers include people included in a top predetermined percentage of people based on evaluation values of the sense of taste, people included in a top predetermined number of people based on evaluation values of the sense of taste, or people whose evaluation values of the sense of taste are larger than or equal to a certain value.

Also, based on a command obtained by the communication unit 21, the control unit 23 selects at least one dish filtered by one search filter or at least one restaurant filtered by one search filter. Based on a command obtained by the communication unit 21, the control unit 23 selects a dish filtered by one search filter and a first restaurant that serves the dish or a second restaurant filtered by one search filter.

The communication unit 21 outputs information indicating the selected at least one dish or restaurant to the communication terminal 1 through the network 3 in order to display the information on the display 14 of the communication terminal 1. The communication unit 21 outputs information indicating the selected dish and first restaurant or the selected second restaurant to the communication terminal 1 through the network 3 in order to display the information on the display 14 of the communication terminal 1.

Subsequently, a description will be given of sense-of-taste evaluation processing for evaluating the user's sense of taste in the second embodiment of the present disclosure.

Figure 21:
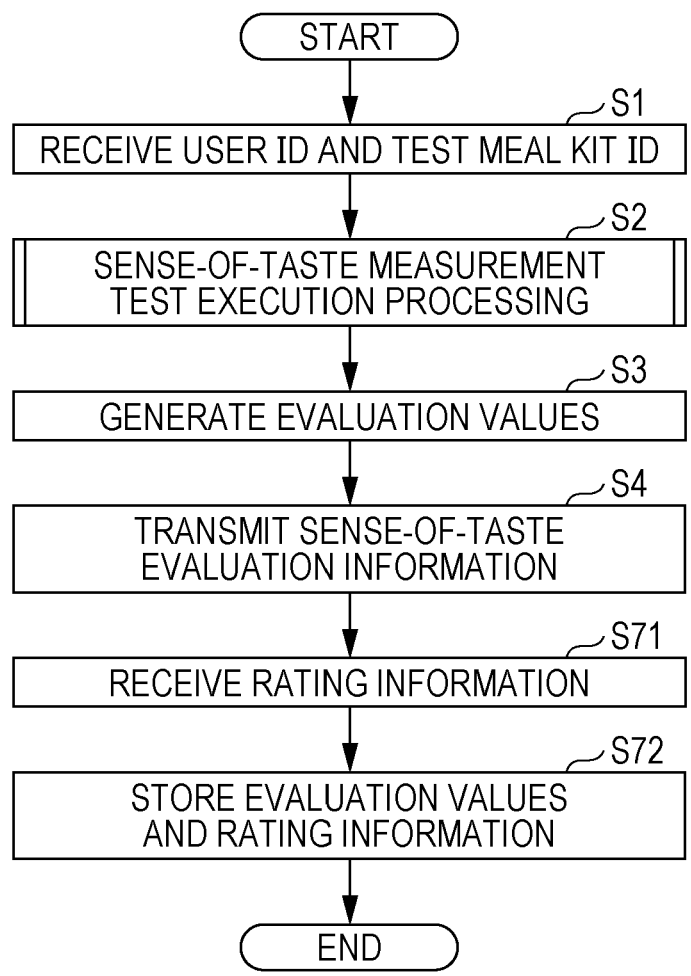
FIG. 21 is a flowchart illustrating sense-of-taste evaluation processing in a management server in a second embodiment of the present disclosure.

FIG. 21 is a flowchart illustrating sense-of-taste evaluation processing in the management server in the second embodiment of the present disclosure.

In FIG. 21, processes that are substantially the same as those in the sense-of-taste evaluation processing illustrated in FIG. 4 are denoted by the same reference numerals, and descriptions thereof will not be given hereinafter.

In step S71, the communication unit 21 receives, from the communication terminal 1, rating information indicating the user's rating of a dish or a restaurant. Each dish or restaurant is rated, for example, in five levels. The operation unit 15 of the communication terminal 1 receives the user's rating of a dish or a restaurant. The user gives points, for example, 5 points to 1 point, to each dish or restaurant. In this case, 5 points is the best, and 1 point is the worst. The communication unit 11 in the communication terminal 1 transmits the rating information to the management server 2.

Next, in step S72, the control unit 23 stores the evaluation values, generated in step S3, and the rating information, received in step S71, in the memory 22 in association with the user ID.

In the second embodiment, in step S2 in FIG. 21, at least one of the measurement tests regarding the sense of taste described above in the first embodiment may be performed. Since the taste-resolution measurement test execution processing in the second embodiment is substantially the same as that in the first embodiment, a description thereof will not be given hereinafter.

In the second embodiment, the measurement test of the taste sensing threshold may be performed in addition to the measurement test of the taste resolution, as in the first modification of the first embodiment. In this case, the taste-resolution measurement test execution processing in step S2 in FIG. 21 is followed by the taste-sensing-threshold measurement test execution processing in step S6 in FIG. 9. Since the taste-sensing-threshold measurement test execution processing in the second embodiment is substantially the same as that in the first modification of the first embodiment, a description thereof will not be given hereinafter.

In the second embodiment, the measurement test of the taste recognition threshold may also be performed in addition to the measurement test of the taste resolution, as in the second modification of the first embodiment. In this case, the taste-resolution measurement test execution processing in step S2 in FIG. 21 is followed by the taste-recognition-threshold measurement test execution processing in step S8 in FIG. 12. Since the taste-recognition-threshold measurement test execution processing in the second embodiment is substantially the same as that in the second modification of the first embodiment, a description thereof will not be given hereinafter.

In the second embodiment, the measurement test of the taste density may also be performed in addition to the measurement test of the taste resolution, as in the third modification of the first embodiment. In this case, the taste-resolution measurement test execution processing in step S2 in FIG. 21 is followed by the taste-density measurement test execution processing in step S10 in FIG. 15. Since the taste-density measurement test execution processing in the second embodiment is substantially the same as that in the third modification of the first embodiment, a description thereof will not be given hereinafter.

In addition, in the second embodiment, at least one of the measurement test of the taste resolution in the first embodiment, the measurement test of the taste sensing threshold in the first modification of the first embodiment, the measurement test of the taste recognition threshold in the second modification of the first embodiment, the measurement test of the taste density in the third modification of the first embodiment, and the measurement test of the taste mixture in the fourth modification of the first embodiment may also be performed.

In addition, even with a method different from the measurement tests regarding the sense of taste described in the present disclosure, the second embodiment of the present disclosure can similarly be applied as long as step S2 in FIG. 21 is a measurement test regarding a taste that can be identified by sense-of-taste top scorers.

Subsequently, a description will be given of a method in which the user registers the rating information. The management server 2 may obtain the rating information during the sense-of-taste evaluation processing or may obtain and register only the rating information when the sense-of-taste evaluation processing is already performed.

Figure 22:
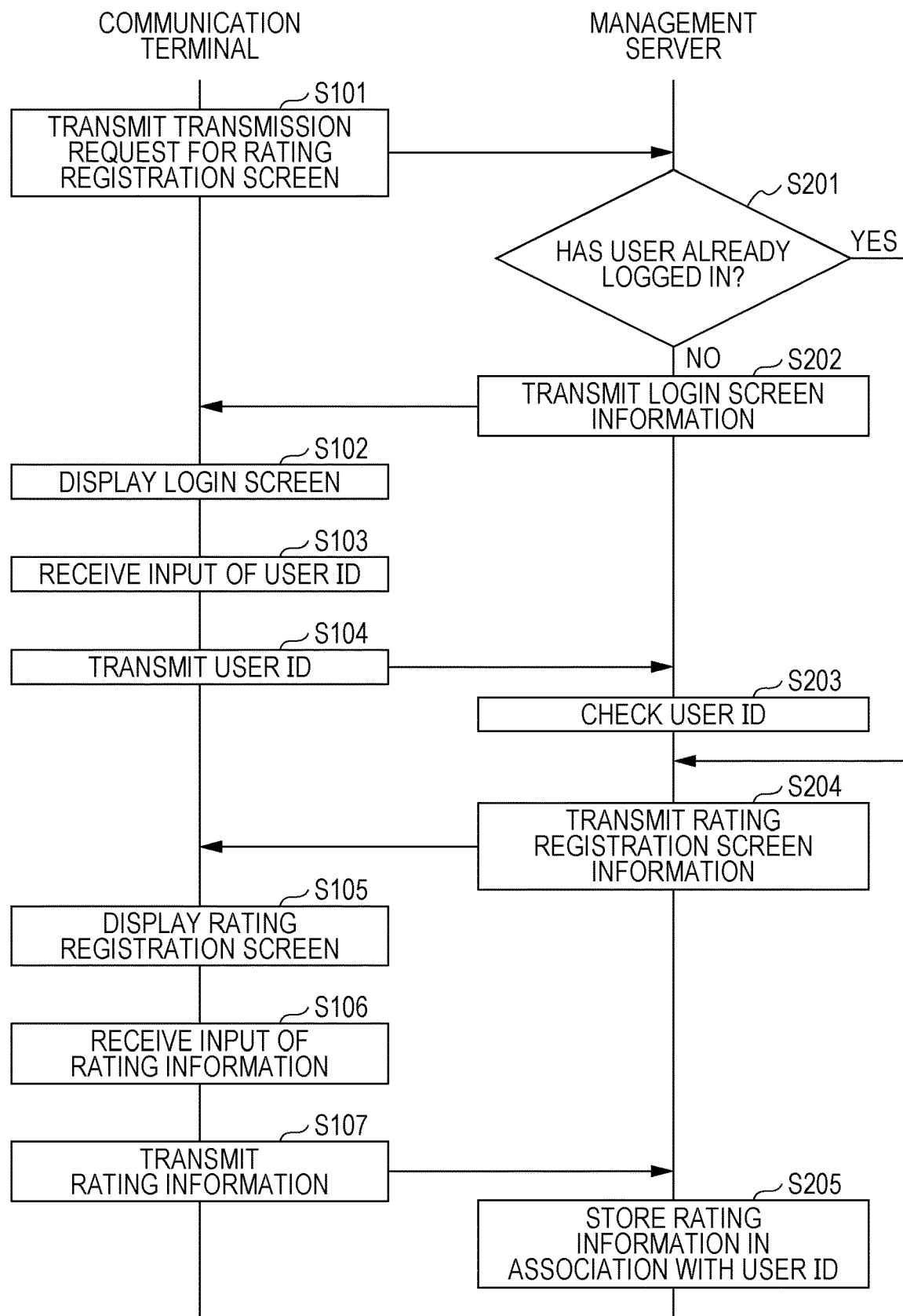
FIG. 22 is a sequence diagram illustrating one example of a rating information registration method in the second embodiment of the present disclosure.

FIG. 22 is a sequence diagram illustrating one example of a rating-information registration method in the second embodiment of the present disclosure.

First, in step S101, the communication unit 11 in the communication terminal 1 transmits, to the management server 2, a transmission request for a rating registration screen for registering the rating information. The communication unit 21 in the management server 2 receives the transmission request from the communication terminal 1.

Next, in step S201, the control unit 23 decides whether or not the user of the communication terminal 1 has already logged in. When it is decided that the user has already logged in (YES in step S201), the process proceeds to step S204.

On the other hand, when it is decided that the user has not logged in (NO in step S201), in step S202, the communication unit 21 transmits, to the communication terminal 1, login screen information for login. The communication unit 11 in the communication terminal 1 receives the login screen information.

Next, in step S102, the display 14 of the communication terminal 1 displays a login screen.

Next, in step S103, the operation unit 15 receives an input of a user ID via the login screen. The user inputs his or her user ID onto the login screen. The operation unit 15 may receive not only the user ID but also an input of a password for authentication.

Next, in step S104, the communication unit 11 transmits the user ID, input using the operation unit 15 to the management server 2. The communication unit 21 in the management server 2 receives the user ID transmitted by the communication terminal 1.

Next, in step S203, the control unit 23 checks whether or not the user ID received by the communication unit 21 matches a pre-registered user ID.

When the received user ID matches the pre-registered user ID, in step S204, the communication unit 21 transmits rating registration screen information indicating a rating registration screen to the communication terminal 1. The communication unit 11 in the communication terminal 1 receives the rating registration screen information transmitted by the management server 2.

When the received user ID does not match the pre-registered user ID, the communication unit 21 transmits, to the communication terminal 1, error screen information for giving a notification indicating that the user ID is erroneous.

Next, in step S105, the display 14 displays the rating registration screen.

Next, in step S106, the operation unit 15 receives an input of rating information indicating the user's rating of a dish or a restaurant via the rating registration screen. The user inputs the rating information onto the rating registration screen. The user gives rating points to a restaurant or gives rating points to a specific dish served at a restaurant.

Next, in step S107, the communication unit 11 transmits the input rating information to the management server 2. The communication unit 21 in the management server 2 receives the rating information transmitted by the communication terminal 1.

Next, in step S205, the control unit 23 stores the rating information, received by the communication unit 21, in a rating database in the memory 22 in association with the user ID. The memory 22 stores therein the rating database and the user information.

FIG. 23 is a table illustrating one example of the rating database.

The name of a restaurant, or the name of a restaurant and the name of a dish served thereat, a user ID, and a rating of the restaurant or the dish are stored in the rating database in association with each other.

FIG. 24 is a table illustrating one example of the user information.

A user ID, a sense-of-taste score, a sense-of-taste characteristic, the country or region where the user resides, and the prefecture where the user resides are included in the user information in association with each other. The sense-of-taste score is an evaluation value of the user's taste sensitivity. The sense-of-taste characteristic is represented by vectors constituted by evaluation values of taste sensitivities to respective taste components of sweetness, sourness, saltiness, bitterness, and umami.

In order to perform filtering with rating information of sense-of-taste top scorers during search for restaurants or dishes, rating information of restaurants or dishes and attribute information (sense-of-taste scores) of evaluators must be associated with each other and be managed. Alternatively, the associations between the rating information and the attribute information of the evaluators need to be obtainable during the search.

Thus, during reception of the rating information on a restaurant or a dish, the management server 2 receives the user ID of an evaluator and the rating information in association with each other.

Additionally, the management server 2 uses the user ID to refer to the attribute information (the sense-of-taste score) in the user information. With two databases, that is, the rating database and the user information, use/non-use of a search filter or a setting condition can be easily and flexibly changed during search for restaurants or dishes. During search for restaurants or dishes, the management server 2 may utilize those two databases.

Subsequently, a description will be given of search processing for searching for dishes or restaurants in the second embodiment.

Figure 25:
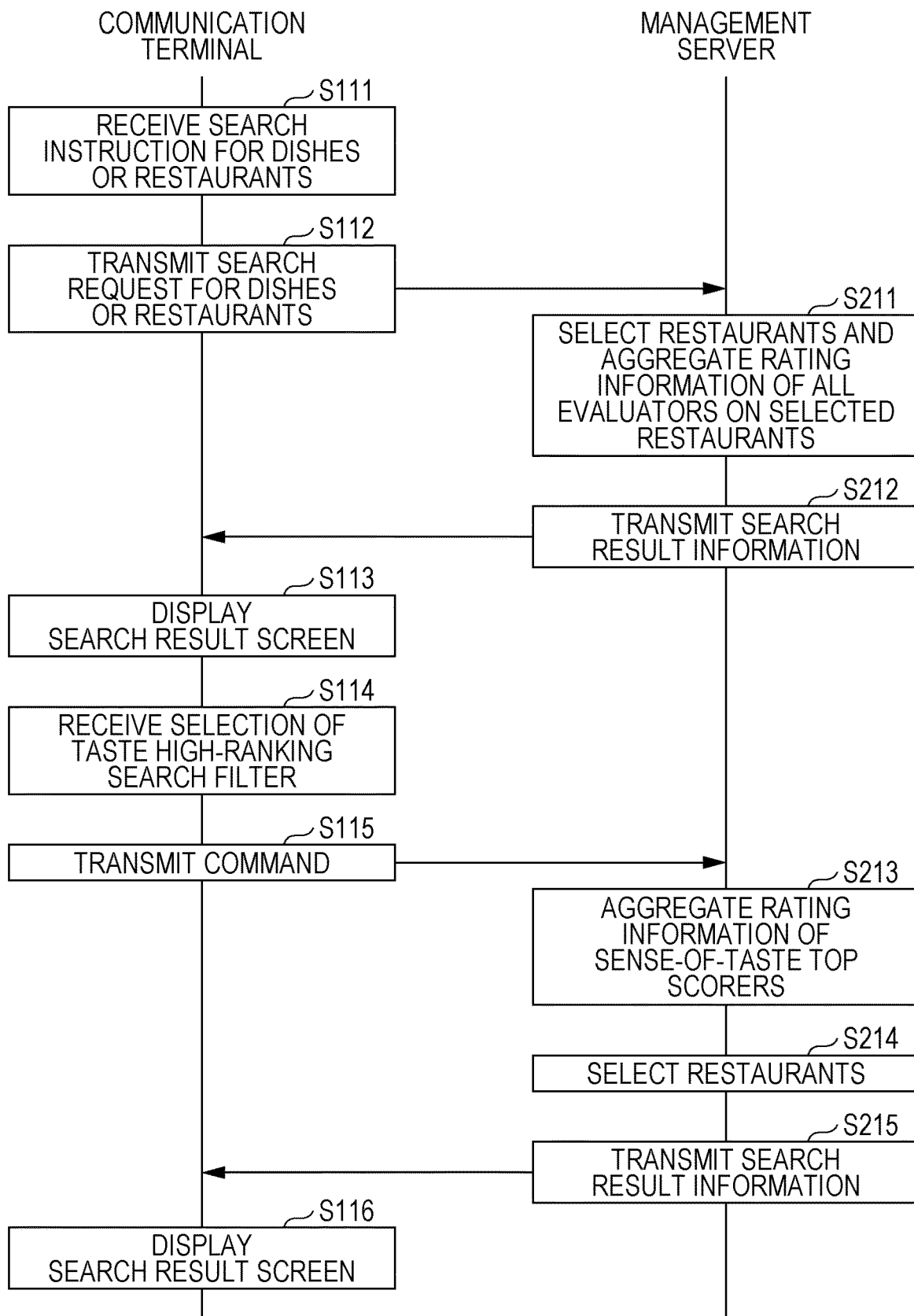
FIG. 25 is a sequence diagram illustrating one example of search processing in the second embodiment of the present disclosure.

FIG. 25 is a sequence diagram illustrating one example of the search processing in the second embodiment of the present disclosure.

First, in step S111, the operation unit 15 of the communication terminal 1 receives a user's search instruction for dishes or restaurants. For example, by performing voice input or text input, the user instructs the operation unit 15 so as to search for restaurants that serve meat dishes or instructs the operation unit 15 so as to search for restaurants located near the current location of the user.

Next, in step S112, the communication unit 11 transmits the search request for dishes or restaurants to the management server 2. The communication unit 21 in the management server 2 receives the search request from the communication terminal 1. The search request may include a search condition. Examples of the search condition include a condition for specifying a type of dish to be searched for, such as a meat dish, a fish dish, or a Japanese dish, and a condition for specifying the locations of restaurants to be searched for, such as near the current location or in a predetermined region.

Next, in step S211, the control unit 23 selects restaurants that satisfy the search condition and also aggregates rating information of all evaluators on the selected restaurants. In accordance with the search condition specified by the user, the control unit 23 selects, for example, restaurants located within a radius of 1 km from the current location. Also, the control unit 23 calculates an average of rating points of all the evaluators who have rated each selected restaurant.

Next, in step S212, the communication unit 21 transmits search result information to the communication terminal 1. The search result information includes information regarding the selected restaurants and the aggregated rating information. The communication unit 11 in the communication terminal 1 receives the search result information transmitted by the management server 2.

Next, in step S113, the display 14 displays a search result screen showing a search result. The search result screen displays the restaurants that satisfy the search condition specified by the user.

The processing in steps S111 to S113 may be known search processing for displaying restaurants that satisfy a search condition specified by a user.

Next, in step S114, the operation unit 15 receives the user's selection of, from among a plurality of search filters, a search filter (a taste high-ranking search filter) for narrowing down the search result to only dishes or restaurants that are highly rated by high-ranking people in sense-of-taste scores. The taste high-ranking search filter filters dishes or restaurants by using rating results of dishes or restaurants rated by the sense-of-taste top scorers. For example, the user selects the taste high-ranking search filter by performing sound input, text input, or operation of a graphical user interface (GUI), described below, displayed on the display 14. The plurality of search filters may include, in addition to the taste high-ranking search filter, for example, a search filter for filtering with a type of dish, a search filter for filtering with an average price spent at restaurants, and a search filter for filtering with open hours.

In step S115, the communication unit 11 transmits, to the management server 2, a command indicating that the taste high-ranking search filter is selected. The communication unit 21 in the management server 2 receives the command transmitted by the communication terminal 1.

Next, in step S213, the control unit 23 aggregates the rating information of the sense-of-taste top scorers. The control unit 23 calculates averages of the rating points of the sense-of-taste top scorers with respect to restaurants located in the surroundings of the current location of the communication terminal 1.

Next, in step S214, the control unit 23 selects, from among the restaurants located in the surroundings of the current location of the communication terminal 1, dishes and/or restaurants for which the averages of the rating points of the sense-of-taste top scorers are larger than or equal to a predetermined value.

Next, in step S215, the communication unit 21 transmits search result information including information regarding the selected dishes and/or restaurants to the communication terminal 1. The communication unit 11 in the communication terminal 1 receives the search result information transmitted by the management server 2.

Next, in step S116, the display 14 displays a search result screen (a search screen) showing the filtering result obtained with the taste high-ranking search filter. Only the dishes and/or restaurants filtered by the taste high-ranking search filter are displayed on the search result screen. That is, of the dishes and/or restaurants in the surroundings of the current location of the user, only dishes and/or restaurants for which the averages of the rating points of the sense-of-taste top scorers are larger than or equal to the predetermined value are displayed on the search result screen.

Figure 26:
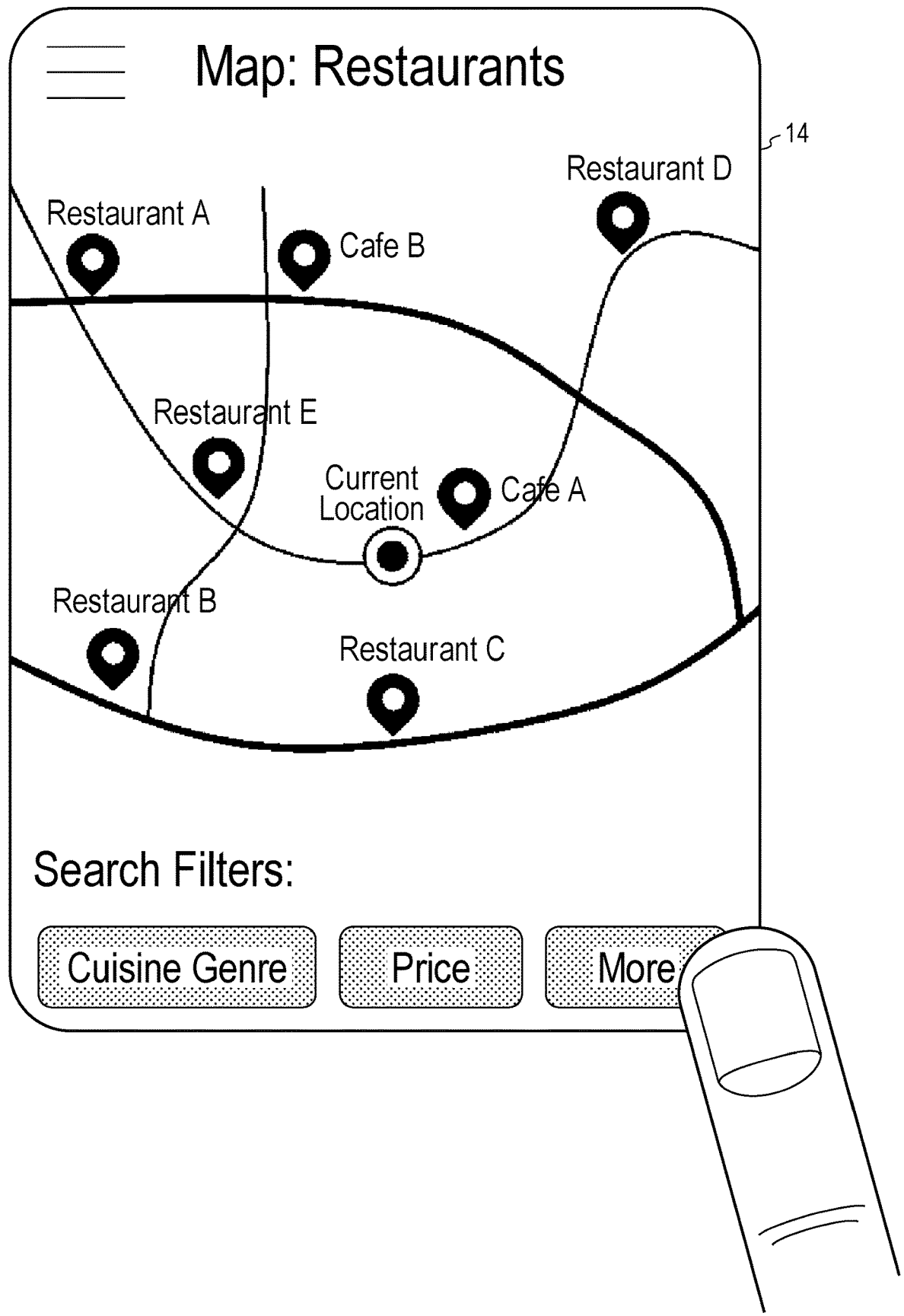
FIG. 26 is a view illustrating one example of a search result screen displayed on a display of a communication terminal in the second embodiment.
Figure 27:
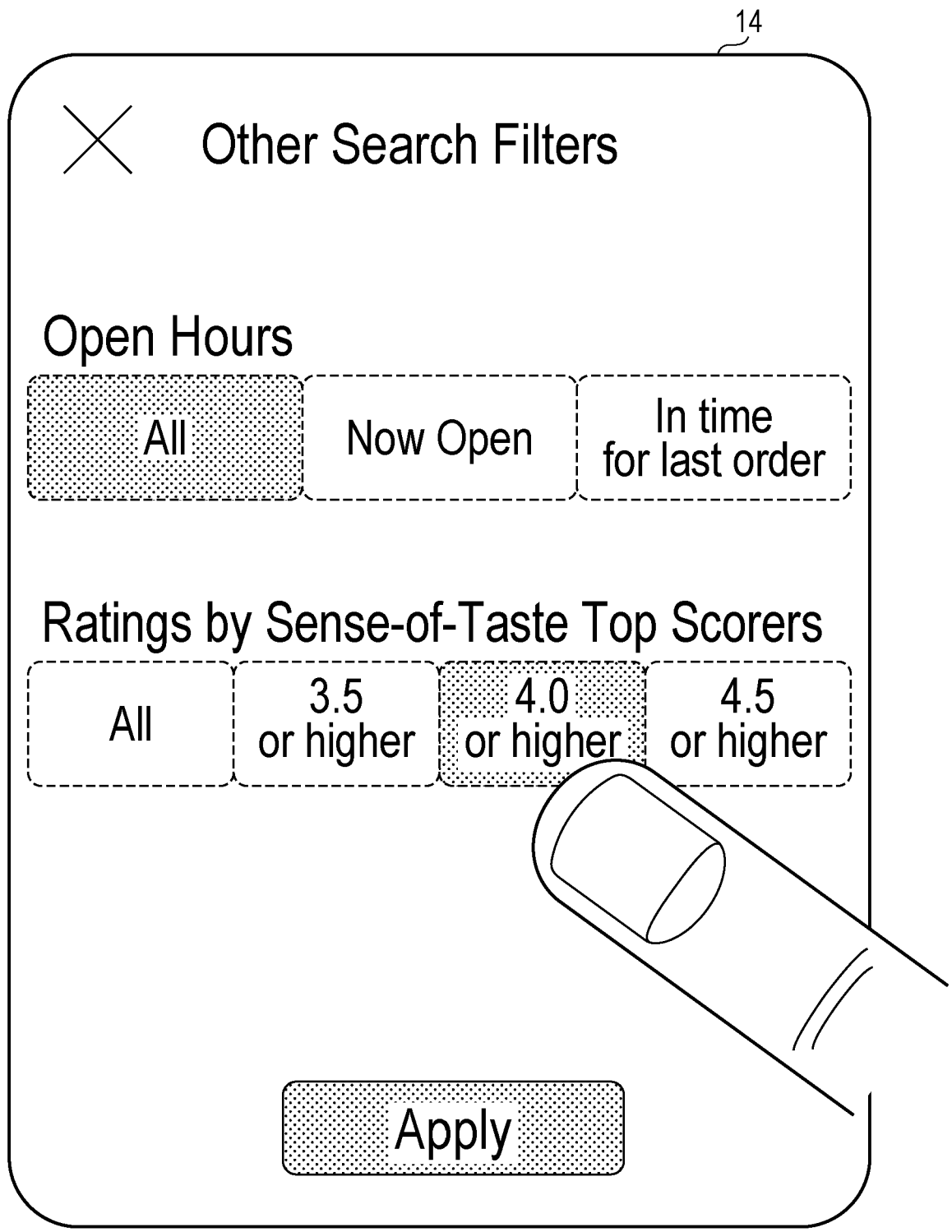
FIG. 27 is a view illustrating one example of a taste high-ranking search filter displayed on the display of the communication terminal in the second embodiment.

FIG. 26 is a view illustrating one example of the search result screen displayed on the display of the communication terminal in the second embodiment, and FIG. 27 is a view illustrating one example of the taste high-ranking search filter displayed on the display of the communication terminal in the second embodiment.

As illustrated in FIG. 26, the display 14 of the communication terminal 1 displays the search result screen. Restaurants located within a radius of 1 km from the current location of the communication terminal 1 are displayed on the map on the search result screen. Buttons for selecting at least one search filter of the plurality of search filters are displayed at a lower portion of the search result screen. When a button showing "More" is touched among the buttons, the search filter screen illustrated in FIG. 27 is displayed.

Other search filters that can be selected by the user are displayed on the search filter screen illustrated in FIG. 27. One search filter for specifying open hours and the taste high-ranking search filter for filtering dishes or restaurants by using rating results of dishes or restaurants rated by sense-of-taste top scorers are displayed on the search filter screen illustrated in FIG. 27.

For example, when the taste high-ranking search filter is specified during search for restaurants located near the user on a map, the management server 2 retrieves only dishes and/or restaurants highly rated by the sense-of-taste top scorers.

The sense-of-taste top scorers include, among all taste test examinees, people having sense-of-taste scores included in a top predetermined percentage of people, people having sense-of-taste scores included in a top predetermined number of people, or people having sense-of-taste scores that are higher than or equal to a certain value. The predetermined percentage of people is, for example, 10%, the predetermined number of people is, for example, 100, and the certain value is, for example, 800 points. The management server 2 may also make the user select restaurants that satisfy one rating result from among four rating results "all", "low rating", "average", and "high rating" of the sense-of-taste top scorers.

Also, the management server 2 may make the user select restaurants, based on five-level rating points (such as average points of the sense-of-taste top scorers), as illustrated in FIG. 27. In this case, when "all" is selected, all restaurants rated by the sense-of-taste top scorers are treated as search targets. When "3.5 or higher" is selected, all restaurants for which the average points of rating points (five-level ratings) of the sense-of-taste top scorers are 3.5 points or higher are treated as search targets. Also, when "4.0 or higher" is selected, all restaurants for which the average points of the rating points (five-level ratings) of the sense-of-taste top scorers are 4.0 points or higher are treated as search targets. Also, when "4.5 or higher" is selected, all restaurants for which the average points of the rating points (five-level ratings) of the sense-of-taste top scorer are 4.5 points or higher are treated as search targets. Lastly, when an "Apply" button is pressed, the taste high-ranking search filter becomes active, so that a search result screen on which the taste high-ranking search filter is reflected is displayed.

Figure 28:
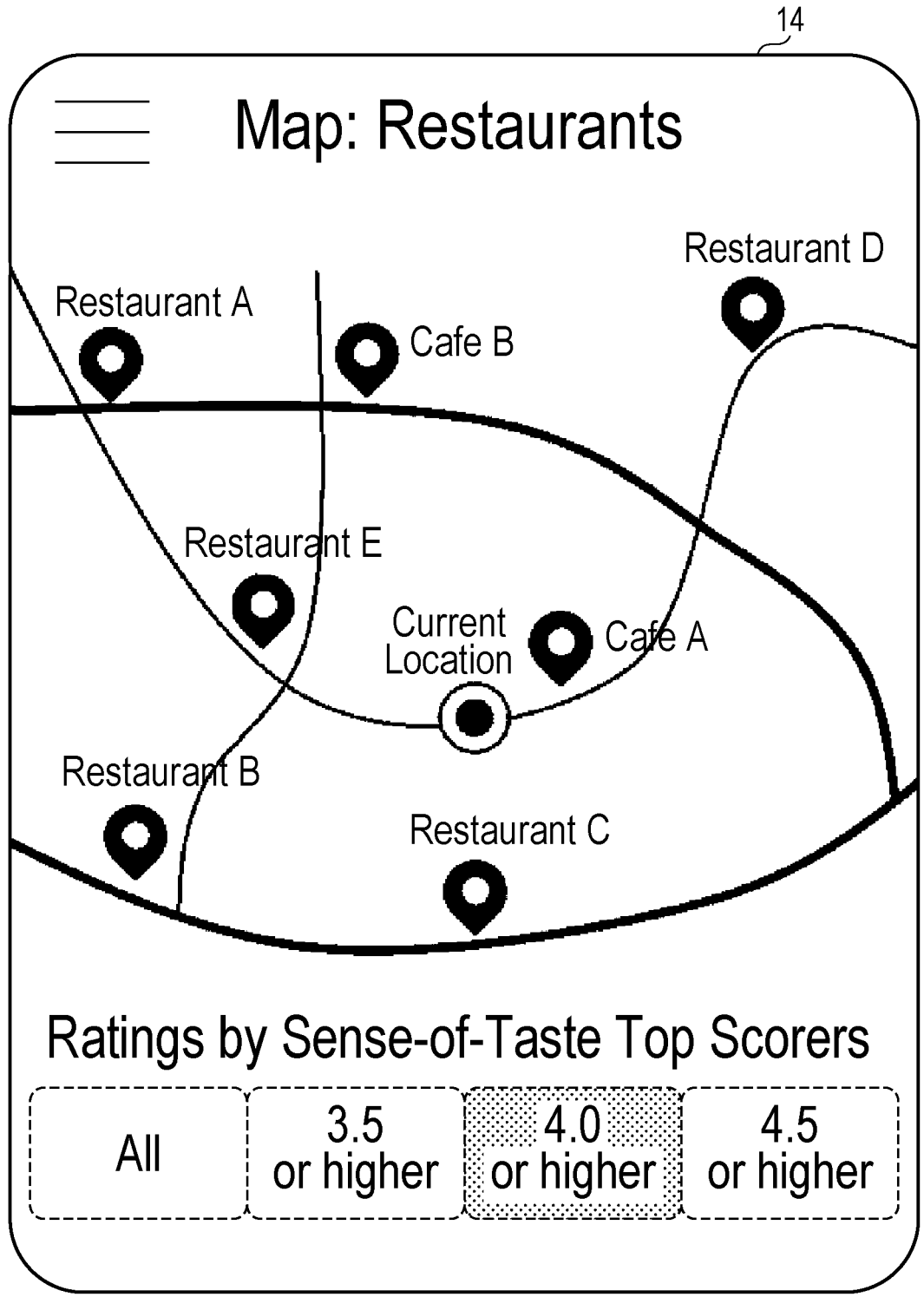
FIG. 28 is a view illustrating a first modification of the search result screen displayed on the display of the communication terminal in the second embodiment.

FIG. 28 is a view illustrating a first modification of the search result screen displayed on the display of the communication terminal.

Although, in FIG. 27, the taste high-ranking search filter is displayed on the screen different from the search result screen, the taste high-ranking search filter illustrated in FIG. 28 is displayed superimposed on the search result screen.

For example, performing filtering based on the rating points of the sense-of-taste top scorers to narrow down restaurants to be displayed is conceivable when the number of restaurants in search result candidates to be displayed on the map is larger than a predetermined number. When the number of restaurants in the search result candidates on the map is larger than the predetermined number, a search condition for the taste high-ranking search filter may also be displayed at a lower portion of the search result screen as a search filter that is effective for further reducing the number of search result candidates, as illustrated in FIG. 28. Also, the search condition for the taste high-ranking search filter may always be displayed on the search result screen.

Figure 29:
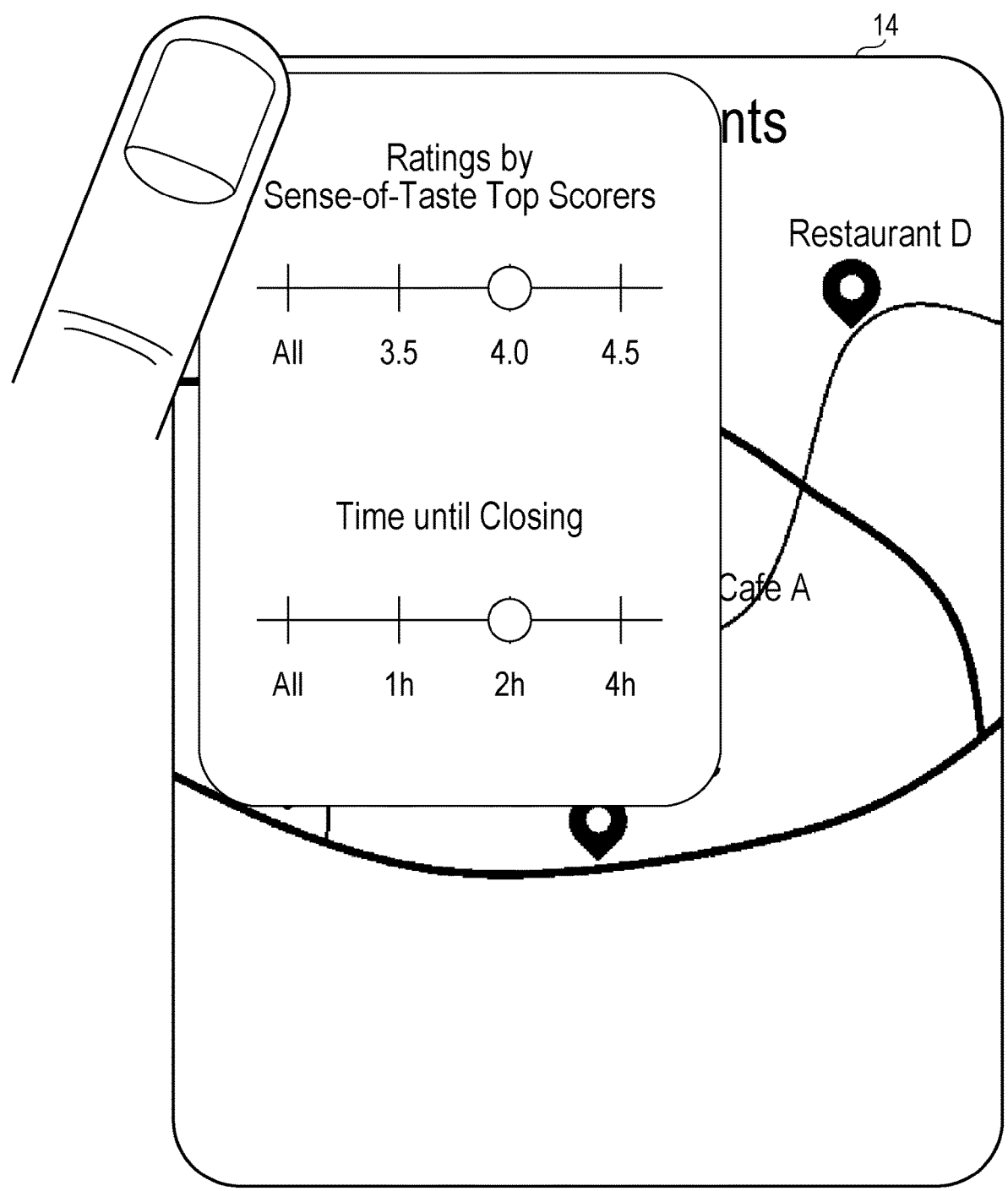
FIG. 29 is a view illustrating a second modification of the search result screen displayed on the display of the communication terminal in the second embodiment.

FIG. 29 is a view illustrating a second modification of the search result screen displayed on the display of the communication terminal.

For example, the display 14 may display a menu button (e.g., a hamburger button, not shown) on an upper left portion on the search result screen, and when the menu button is selected, the display 14 may display an image for receiving an input of a search condition for the taste high-ranking search filter.

When the menu button is pressed, a menu image is displayed superimposed on the search result screen, and a search condition for the taste high-ranking search filter is displayed in the menu image, as illustrated in FIG. 29.

In this case, a condition that the average points of the rating points of the sense-of-taste top scorers are 4.0 or higher and a condition that the time from the current time until the closing time of restaurants is two hours or more are selected as search conditions for restaurants to be displayed on the map.

Although, in this case, the taste high-ranking search filter that allows for setting of the condition regarding ratings on dishes or restaurants, the ratings being given by the sense-of-taste top scorers, is provided, the present disclosure not particularly limited thereto. For example, an ON/OFF button for "Restaurants popular among sense-of-taste top scorers" may be provided as a taste high-ranking search filter.

According to the second embodiment, when the evaluation values in the measurement test regarding the user's sense of taste satisfy the certain condition for the sense-of-taste top scorers, the rating information indicating the user's rating of a dish or a restaurant is included in rating results of dishes or restaurants rated by the sense-of-taste top scorers. One search filter for filtering a search result of dishes or restaurants by using the rating results of the dishes or restaurants rated by the sense-of-taste top scorers is provided on the dish search screen. Accordingly, dishes or restaurants highly rated by the sense-of-taste top scorers can be presented to the user as a search result in a comprehensive manner.

Also, according to the second embodiment, dishes or restaurants are filtered by one search filter by using rating results of dishes or restaurants rated by the sense-of-taste top scorers, and a first restaurant that serves a dish filtered by one search filter or a second restaurant filtered by one search filter is displayed on the display 14 of the communication terminal 1. Accordingly, dishes or restaurants that are more highly rated by the sense-of-taste top scorers can be presented to the user as a search result.

In addition, without inputting the evaluation values of the user's sense of taste during rating of a dish or a restaurant, the user is made to perform login to thereby associate the evaluation values (the sense-of-taste score in FIG. 24) of the user's sense of taste and the rating database (FIG. 23) via the user ID used for the login. Thus, without causing a new burden on the evaluators, rating information on dishes or restaurants can be registered and utilized in connection with the information regarding the taste sensitivity of the evaluator.

In addition, when the evaluation values of the user's sense of taste satisfy the certain condition for the sense-of-taste top scorers, the rating information indicating the user's rating of a dish or a restaurant is included in the rating results of dishes or restaurants rated by the sense-of-taste top scorers. Accordingly, the rating results of users whose evaluation values of the sense of taste satisfy the certain condition for the sense-of-taste top scorers can be used to filter dishes or restaurants.

Third Embodiment

An information management system in a third embodiment provides a dish search screen. One search filter for filtering dishes or restaurants by using rating results of dishes or restaurants rated by residents in a specific region is provided on the dish search screen as one of a plurality of search filters.

The configuration of the information management system in the third embodiment is substantially the same as the configuration of the information management system in the first embodiment illustrated in FIG. 1. Thus, the configuration of the information management system in the third embodiment will be described with reference to FIG. 1.

The display 14 of the communication terminal 1 displays a dish search screen. One search filter for filtering dishes or restaurants by using rating results of dishes or restaurants rated by residents in a specific region is provided on the dish search screen as one of the plurality of search filters.

In this case, the residents in the specific region are residents in the surroundings of the current location of the communication terminal 1. That is, one search filter filters dishes or restaurants by using rating results of dishes or restaurants rated by the residents in the surroundings of the current location of the communication terminal 1. For example, when the user of the communication terminal 1 travels, one search filter filters dishes or restaurants by using rating results of dishes or restaurants rated by local residents at the destination of the travel.

Also, one search filter filters dishes or restaurants by using rating results of dishes or restaurants rated by specific evaluators.

The operation unit 15 receives the user's rating of a dish or a restaurant. The operation unit 15 also receives the user's selection of one search filter via the dish search screen.

The communication unit 11 transmits address information indicating the address of the user of the communication terminal 1 to the management server 2. The address information may be pre-stored in the memory 12 or may be input by the user via the operation unit 15. Also, the communication unit 11 transmits rating information indicating the user's rating of a dish or a restaurant to the management server 2. Also, the communication unit 11 transmits a command indicating that one search filter is selected to the management server 2.

The communication unit 21 in the management server 2 obtains the address information indicating the address of the user of the communication terminal 1 from the communication terminal 1 through the network 3. The communication unit 21 also obtains, from the communication terminal 1 through the network 3, first data indicating input values in a measurement test regarding the sense of taste of the user of the communication terminal 1. The measurement test regarding the sense of taste is used to measure the user's taste sensitivity to at least one type of taste.

The measurement test regarding the sense of taste in the third embodiment may be performed in the same manner as the measurement test regarding the sense of taste described above in the first embodiment.

The communication unit 21 also obtains, from the communication terminal 1, rating information indicating the user's rating of a dish or a restaurant. In addition, the communication unit 21 obtains, from the communication terminal 1 through the network 3, a command indicating that one search filter is selected.

Based on the first data, the control unit 23 may generate evaluation values of the user's sense of taste in association with the user. In addition, based on the address information, the control unit 23 may identify the user's address in association with the user.

When the address indicated by the address information is included in a specific region, rating information indicating the user's rating of a dish or a restaurant is included in rating results of dishes or restaurants rated by residents in the specific region. When the address indicated by the address information is included in a country or region where there is a dish or a restaurant, the rating information indicating the user's rating of the dish or the restaurant is included in rating results of dishes or restaurants rated by specific evaluators.

Also, based on a command obtained by the communication unit 11, the control unit 23 selects at least one dish filtered by one search filter or at least one restaurant filtered by one search filter. Based on a command obtained by the communication unit 11, the control unit 23 selects a dish filtered by one search filter and a first restaurant that serves the dish or a second restaurant filtered by one search filter.

The communication unit 21 outputs information indicating a selected at least one dish or restaurant to the communication terminal 1 through the network 3 in order to display the information on the display 14 of the communication terminal 1. The communication unit 21 outputs information indicating the selected dish and first restaurant or the selected second restaurant to the communication terminal 1 through the network 3 in order to display the information on the display 14 of the communication terminal 1.

Subsequently, a description will be given of sense-of-taste evaluation processing for evaluating the user's sense of taste in the third embodiment of the present disclosure.

Figure 30:
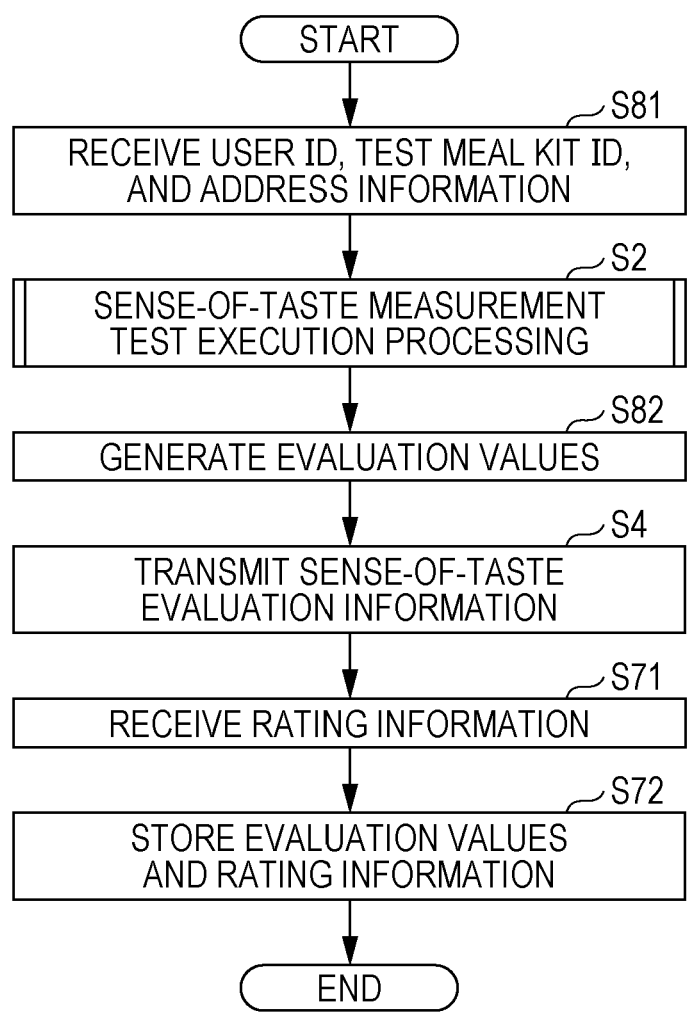
FIG. 30 is a flowchart illustrating sense-of-taste evaluation processing in the management server in a third embodiment of the present disclosure.

FIG. 30 is a flowchart illustrating sense-of-taste evaluation processing in the management server in the third embodiment of the present disclosure.

In FIG. 30, processes that are substantially the same as those in the sense-of-taste evaluation processing illustrated in FIGS. 4 and 21 are denoted by the same reference numerals, and descriptions thereof will not be given hereinafter.

First, in step S81, the communication unit 21 receives a user ID, a test meal kit ID, and address information transmitted by the communication terminal 1. In this case, the communication terminal 1 receives the user's inputs of a test meal kit ID printed on a test meal kit, a user ID, and address information indicating the user's address. The communication terminal 1 displays an input screen, provided by the management server 2, on a web browser and receives inputs of the user ID, the test meal kit ID, and the address information via the input screen. The input screen is specified by a predetermined URL. The communication terminal 1 transmits the input user ID, test meal kit ID, and address information to the management server 2.

Through reading a two-dimensional code printed on the test meal kit, the communication terminal 1 may display the input screen, provided by the management server 2, on a web browser and may receive inputs of the user ID, the test meal kit ID, and the address information via the input screen.

Also, user information in which the user ID and the address information are associated with each other may be stored in the memory 12 in the communication terminal 1. The operation unit 15 of the communication terminal 1 may receive inputs of the user ID and the test meal kit ID without receiving an input of the address information. The control unit 13 may read, from the memory 12, the address information corresponding to the input user ID.

In step S82, based on the first data, the control unit 23 generates evaluation values of the user's sense of taste in association with the user.

In the third embodiment, in step S2 in FIG. 30, at least one of the measurement tests regarding the sense of taste described above in the first embodiment may be performed. Since the taste-resolution measurement test execution processing in the third embodiment is substantially the same as that in the first embodiment, a description thereof will not be given hereinafter.

In the third embodiment, the measurement test of the taste sensing threshold may also be performed in addition to the measurement test of the taste resolution, as in the first modification of the first embodiment. In this case, the taste-resolution measurement test execution processing in step S2 in FIG. 30 is followed by the taste-sensing-threshold measurement test execution processing in step S6 in FIG. 9. Since the taste-sensing-threshold measurement test execution processing in the third embodiment is substantially the same as that in the first modification of the first embodiment, a description thereof will not be given hereinafter.

In the third embodiment, the measurement test of the taste recognition threshold may also be performed in addition to the measurement test of the taste resolution, as in the second modification of the first embodiment. In this case, the taste-resolution measurement test execution processing in step S2 in FIG. 30 is followed by the taste-recognition-threshold measurement test execution processing in step S8 in FIG. 12. Since the taste-recognition-threshold measurement test execution processing in the third embodiment is substantially the same as that in the second modification of the first embodiment, a description thereof will not be given hereinafter.

In the third embodiment, the measurement test of the taste density may also be performed in addition to the measurement test of the taste resolution, as in the third modification of the first embodiment. In this case, the taste-resolution measurement test execution processing in step S2 in FIG. 30 is followed by the taste-density measurement test execution processing in step S10 in FIG. 15. Since the taste-density measurement test execution processing in the third embodiment is substantially the same as that in the third modification of the first embodiment, a description thereof will not be given hereinafter.

In addition, at least one of the measurement test of the taste resolution in the first embodiment, the measurement test of the taste sensing threshold in the first modification of the first embodiment, the measurement test of the taste recognition threshold in the second modification of the first embodiment, the measurement test of the taste density in the third modification of the first embodiment, and the measurement test of the taste mixture in the fourth modification of the first embodiment may also be performed in the third embodiment.

In addition, even with a method different from the measurement test regarding the sense of taste described in the present disclosure, the third embodiment of the present disclosure can similarly be applied, as long as step S2 in FIG. 30 is a measurement test regarding a taste that can be identified by residents in the surroundings of the current location of the communication terminal 1.

Subsequently, a description will be given of search processing for searching for dishes or restaurants in the third embodiment.

Figure 31:
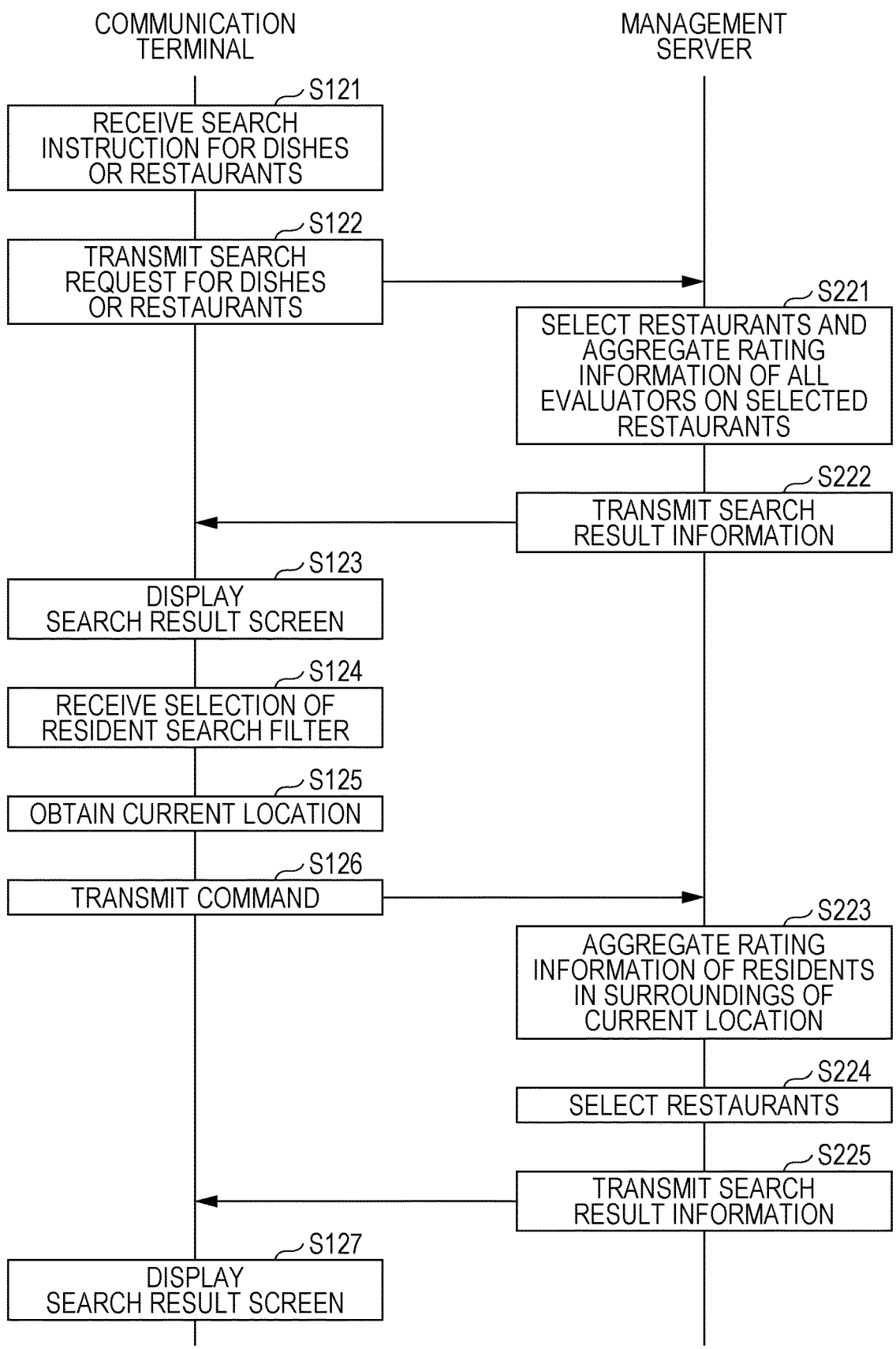
FIG. 31 is a sequence diagram illustrating one example of search processing in the third embodiment of the present disclosure.

FIG. 31 is a sequence diagram illustrating one example of the search processing in the third embodiment of the present disclosure.

Since processes in steps S121 to S123 and steps S221 and S222 illustrated in FIG. 31 are substantially the same as the processes in steps S111 to S113 and steps S211 and S212 illustrated in FIG. 25, descriptions thereof will not be given hereinafter.

In step S124, the operation unit 15 receives the user's selection of a resident search filter from among a plurality of search filters. The resident search filter filters dishes or restaurants by using rating results of dishes or restaurants rated by residents in the surroundings of the current location of the communication terminal 1. For example, the user selects the resident search filter by performing sound input, text input, or operation of a GUI, described below, displayed on the display 14. The plurality of search filters may include, in addition to the resident search filter, for example, a search filter for filtering with a type of dish, a search filter for filtering with an average price spent at restaurants, and a search filter for filtering with open hours.

Next, in step S125, a location measurement unit obtains the current location of the communication terminal 1. The communication terminal 1 includes the location measurement unit for measuring the current location of the communication terminal 1. The location measurement unit is, for example, a global positioning system (GPS) device.

Next, in step S126, the communication unit 11 transmits a command indicating that the resident search filter is selected to the management server 2. The command includes current location information indicating the current location of the communication terminal 1. The communication unit 21 in the management server 2 receives the command transmitted by the communication terminal 1.

Next, in step S223, the control unit 23 aggregates rating information of the residents in the surroundings of the current location of the communication terminal 1. The residents in the surroundings of the current location are, for example, people who live within a radius of 10 km from the current location or people who live in a region including the current location (this region may be, for example, a unit, such as a country, a prefecture, or a municipality). The control unit 23 calculates averages of the rating points of the residents in the surroundings of the current location who have rated restaurants located in the surroundings of the current location of the communication terminal 1.

Next, in step S224, the control unit 23 selects, from among the restaurants located in the surroundings of the current location of the communication terminal 1, dishes and/or restaurants for which the averages of the rating points of the residents in the surroundings of the current location are larger than or equal to a predetermined value.

Next, in step S225, the communication unit 21 transmits search result information including information regarding the selected dishes and/or restaurants to the communication terminal 1. The communication unit 11 in the communication terminal 1 receives the search result information transmitted by the management server 2.

Next, in step S127, the display 14 displays a search result screen showing a filtering result obtained with the resident search filter. The search result screen displays only the dishes and/or restaurants filtered by the resident search filter.

That is, of the dishes and/or restaurants in the surroundings of the current location of the user, only dishes and/or restaurants for which the averages of the rating points of the residents in the surroundings of the current location are larger than or equal to a predetermined value are displayed on the search result screen.

In the third embodiment, only people having a region of residence or sphere of life in which the current location of the user is located are regarded as a rating population to search for highly rated restaurants or dishes. For example, the region of residence or the sphere of life of the user is pre-registered in the management server 2 as user information at a granularity of country, prefecture, or municipality. The management server 2 manages the address information of the user in conjunction with the user ID and the rating information on restaurants or dishes. For example, the resident search filter may search for restaurants that serve dishes highly rated by the residents in the surroundings of the current location or restaurants highly rated by the residents in the surroundings of the current location.

Figure 32:
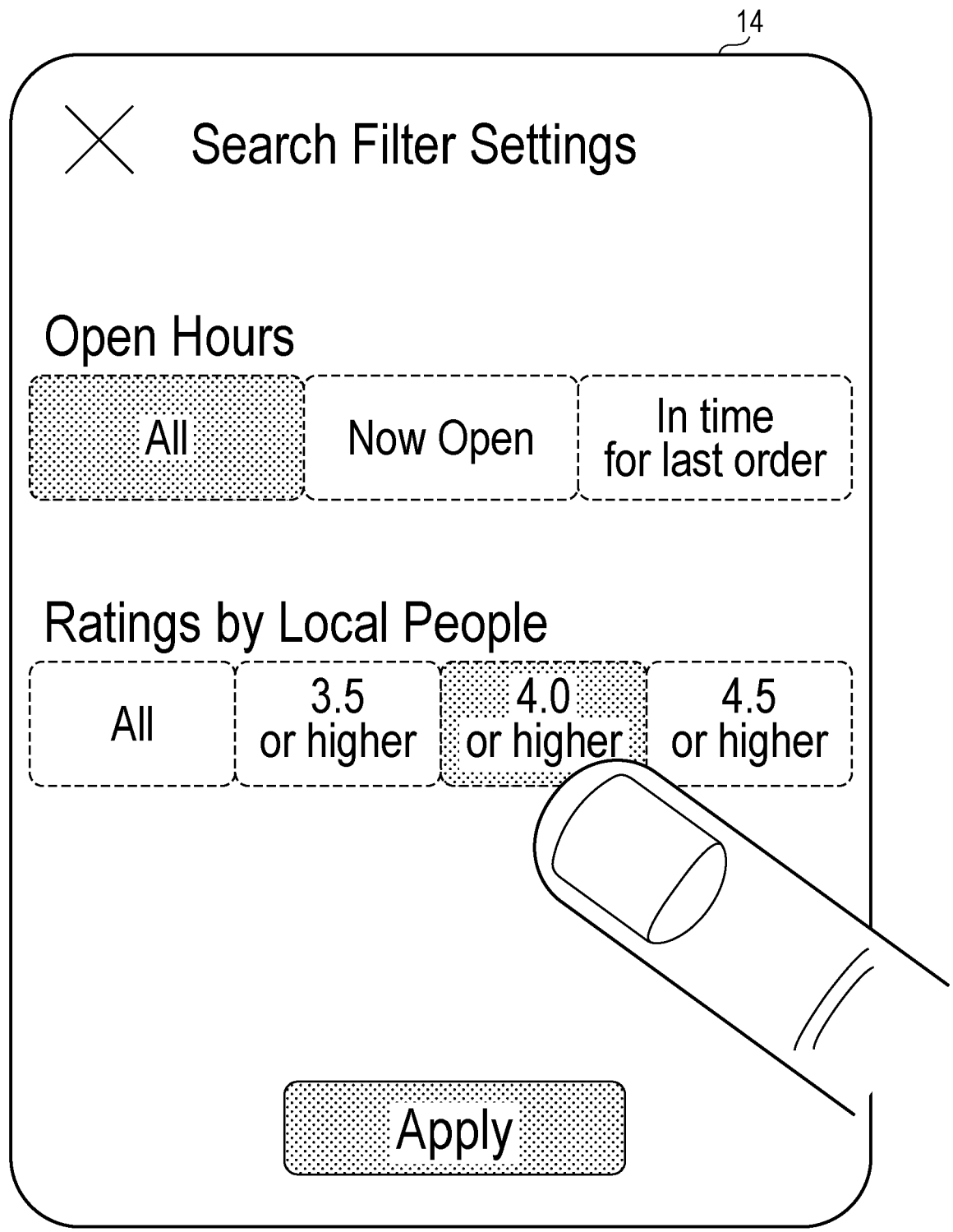
FIG. 32 is a view illustrating one example of a resident search filter displayed on the display of the communication terminal in the third embodiment.

FIG. 32 is a view illustrating one example of the resident search filter displayed on the display 14 of the communication terminal 1 in the third embodiment.

The search filter screen illustrated in FIG. 32 displays other search filters that can be selected by the user. One search filter for specifying open hours and the resident search filter for filtering dishes or restaurants by using rating results of dishes or restaurants rated by residents (local people) in the surroundings of the current location are displayed on the search filter screen illustrated in FIG. 32.

For example, when the resident search filter is specified during search for restaurants located near the user on the map, the management server 2 retrieves only dishes and/or restaurants highly rated by the residents in the surroundings of the current location. The management server 2 may also make the user select restaurants that satisfy one rating result from among four rating results "all", "low rating", "average", and "high rating" of the residents in the surroundings of the current location.

Also, as illustrated in FIG. 32, the management server 2 may make the user select restaurants, based on five-level rating points (such as average points of the residents in the surroundings of the current location). In this case, when "All" is selected, all restaurants rated by the residents in the surroundings of the current location are treated as search targets. When "3.5 or higher" is selected, all restaurants for which the average points of rating points (five-level ratings) of the residents in the surroundings of the current location are 3.5 or higher or higher are treated as search targets. Also, when "4.0 or higher" is selected, all restaurants for which the average points of the rating points (five-level ratings) of the residents in the surroundings of the current location are 4.0 points or higher are treated as search targets. Also, when "4.5 or higher" is selected, all restaurants for which the average points of the rating points (five-level ratings) of the residents in the surroundings of the current location are 4.5 points or higher are treated as search targets. Lastly, when an "Apply" button is pressed, the resident search filter becomes active, so that a search result screen on which the resident search filter is reflected is displayed.

The resident search filter is useful, for example, when the user goes to an unfamiliar region in the country where he or she lives or goes to a foreign country and wishes to have a dish that is rated to be delicious by people living locally.

Although the resident search filter that allows for setting of a condition regarding ratings on dishes or restaurants, the ratings being given by the residents in the surroundings of the current location, is provided in this case, the present disclosure is not particularly limited thereto. For example, an ON/OFF button for "Restaurants popular among local people" may be provided as the resident search filter.

Also, although the resident search filter in the third embodiment filters dishes or restaurants by using rating results of dishes or restaurants rated by residents in the surroundings of the current location of the communication terminal 1, the present disclosure is not particularly limited thereto. The resident search filter may filter dishes or restaurants by using rating results of dishes or restaurants rated by sense-of-taste top scorers who reside in the surroundings of the current location of the communication terminal 1. That is, when the address indicated by the address information is included in a specific region, and the evaluation values of the user's sense of taste satisfy a certain condition for the sense-of-taste top scorers who reside in the specific region, the rating information indicating the user's rating of a dish or a restaurant is included in the rating results of dishes or restaurants rated by the sense-of-taste top scorers.

In this case, the dishes or restaurants rated by the sense-of-taste top scorers who reside in the surroundings of the current location of the communication terminal 1 are selected rather than merely selecting the dishes or restaurants rated by the residents in the surroundings of the current location of the communication terminal 1. This allows the management server 2 to search for restaurants highly rated by people who have high taste sensitivities among the residents in the surroundings of the current location.

Also, when the address indicated by the address information is included in a specific region, and the sense-of-taste characteristic indicated by the evaluation values of the user's sense of taste are similar to the sense-of-taste characteristics of residents in the specific region, the rating information indicating the user's rating of a dish or a restaurant may be included in the rating results of dishes or restaurants rated by the residents in the specific region.

Also, the resident search filter may filter dishes or restaurants by using rating results of dishes or restaurants rated by other users who reside in the surroundings of the current location of the communication terminal 1 and who have sense-of-taste characteristics similar to that of the user. That is, rather than merely selecting the dishes or restaurants rated by the residents in the surroundings of the current location of the communication terminal 1, the dishes or restaurants rated by the other users who reside in the surroundings of the current location of the communication terminal 1 and who have sense-of-taste characteristics similar to that of the user are selected. This allows the management server 2 to search for restaurants highly rated by people who are included in the residents in the surroundings of the current location and who have sense-of-taste characteristics similar to that of the user.

Subsequently, search processing for searching for dishes or restaurants will be described in a first modification of the third embodiment.

In the third embodiment described above, the resident search filter filters dishes or restaurants by using the rating results of dishes or restaurants rated by the residents in the surroundings of the current location of the communication terminal 1. In contrast, in the first modification of the third embodiment, the resident search filter filters dishes or restaurants by using rating results of dishes or restaurants rated by residents in the same region or country as the user of the communication terminal 1. That is, in the first modification of the third embodiment, the specific region is the region of residence, the country of residence, or the sphere of life of the user of the communication terminal 1.

Figure 33:
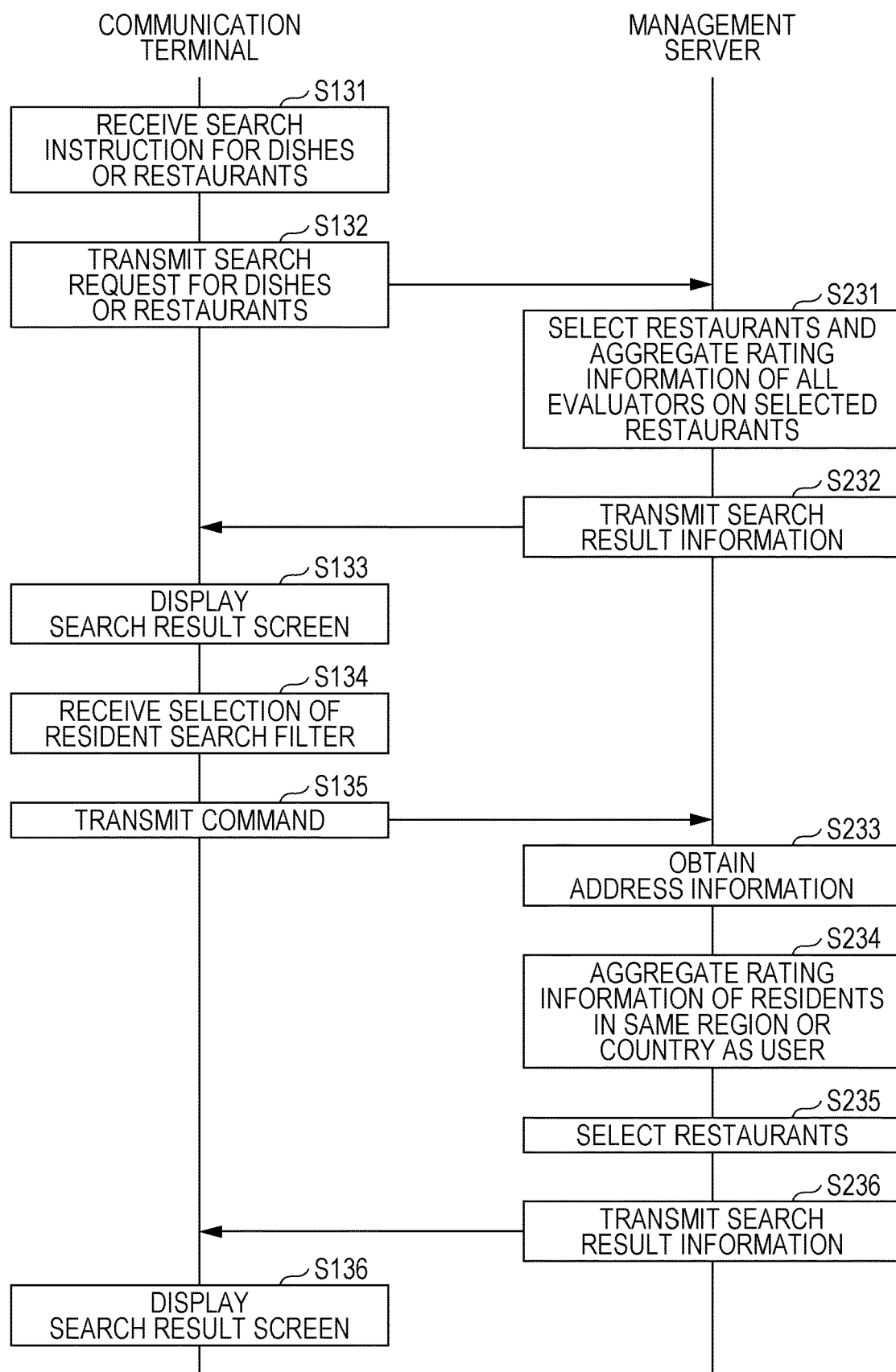
FIG. 33 is a sequence diagram illustrating one example of search processing in a first modification of the third embodiment of the present disclosure.

FIG. 33 is a sequence diagram illustrating one example of search processing in the first modification of the third embodiment of the present disclosure.

Since processes in steps S131 to S133 and steps S231 and S232 illustrated in FIG. 33 are substantially the same as the processes in steps S111 to S113 and steps S211 and S212 illustrated in FIG. 25, descriptions thereof will not be given hereinafter.

In step S134, the operation unit 15 receives the user's selection of a resident search filter from among a plurality of search filters. The resident search filter filters dishes or restaurants by using rating results of dishes or restaurants rated by residents in the same region or country as the user of the communication terminal 1. For example, the user selects the resident search filter by performing sound input, text input, or operation of a GUI, described below, displayed on the display 14. The plurality of search filters may include, in addition to the resident search filter, for example, a search filter for filtering with a type of dish, a search filter for filtering with an average price spent at restaurants, and a search filter for filtering with open hours.

Next, in step S135, the communication unit 11 transmits a command indicating that the resident search filter is selected to the management server 2. The command includes the user ID of the user of the communication terminal 1. The communication unit 21 in the management server 2 receives the command transmitted by the communication terminal 1.

Next, in step S233, the control unit 23 obtains the address information of the communication terminal 1. The memory 22 stores therein user information in which the user ID and the address information of the user are associated with each other. The control unit 23 reads, from the memory 22, the address information corresponding to the user ID included in the command.

Next, in step S234, the control unit 23 aggregates rating information of the residents in the same region or country as the user of the communication terminal 1. The residents in the same region as the user are, for example, people who live within a radius 10 km from the user's address or people who live in a region including the user's address (this region may be, for example, a unit, such as a country, a prefecture, or a municipality). The control unit 23 calculates averages of rating points of residents who live in the same region or country as the user and who have rated restaurants located in the surroundings of the current location of the communication terminal 1.

Next, in step S235, the control unit 23 selects, from among dishes and/or restaurants to be searched, dishes and/or restaurants for which the averages of the rating points of the residents in the same region or country as the user are larger than or equal to a predetermined value. The dishes and/or restaurants to be searched may be, for example, dishes served by restaurants included in a map displayed on the display 14 of the communication terminal 1 and/or restaurants included in the map. Alternatively, the dishes and/or restaurants to be searched may be dishes of a dish type (e.g., Japanese dish) specified by the user and/or restaurants that serve the dishes.

Next, in step S236, the communication unit 21 transmits, to the communication terminal 1, search result information including information regarding the selected dishes and/or restaurants. The communication unit 11 in the communication terminal 1 receives the search result information transmitted by the management server 2.

Next, in step S136, the display 14 displays a search result screen showing a filtering result obtained with the resident search filter. The search result screen displays only the dishes and/or restaurants filtered by the resident search filter. That is, of the dishes and/or restaurants to be searched, only dishes and/or restaurants for which the averages of the rating points of the residents in the same region or country as the user are larger than or equal to the predetermined value are displayed on the search result screen.

In some cases, owing to a difference in food culture, a cuisine in a certain country or region does not suit people in another country or region. In the first modification of the third embodiment, even when the user is in another country or region where the food culture is different, people who reside in the same country or region as the user are regarded as a rating population to search for restaurants or dishes highly rated by the people. This search filter is utilized, for example, when a user who is a Japanese goes to a foreign country and searches the vicinity of the current location of the user for restaurants or dishes highly rated by Japanese people.

Figure 34:
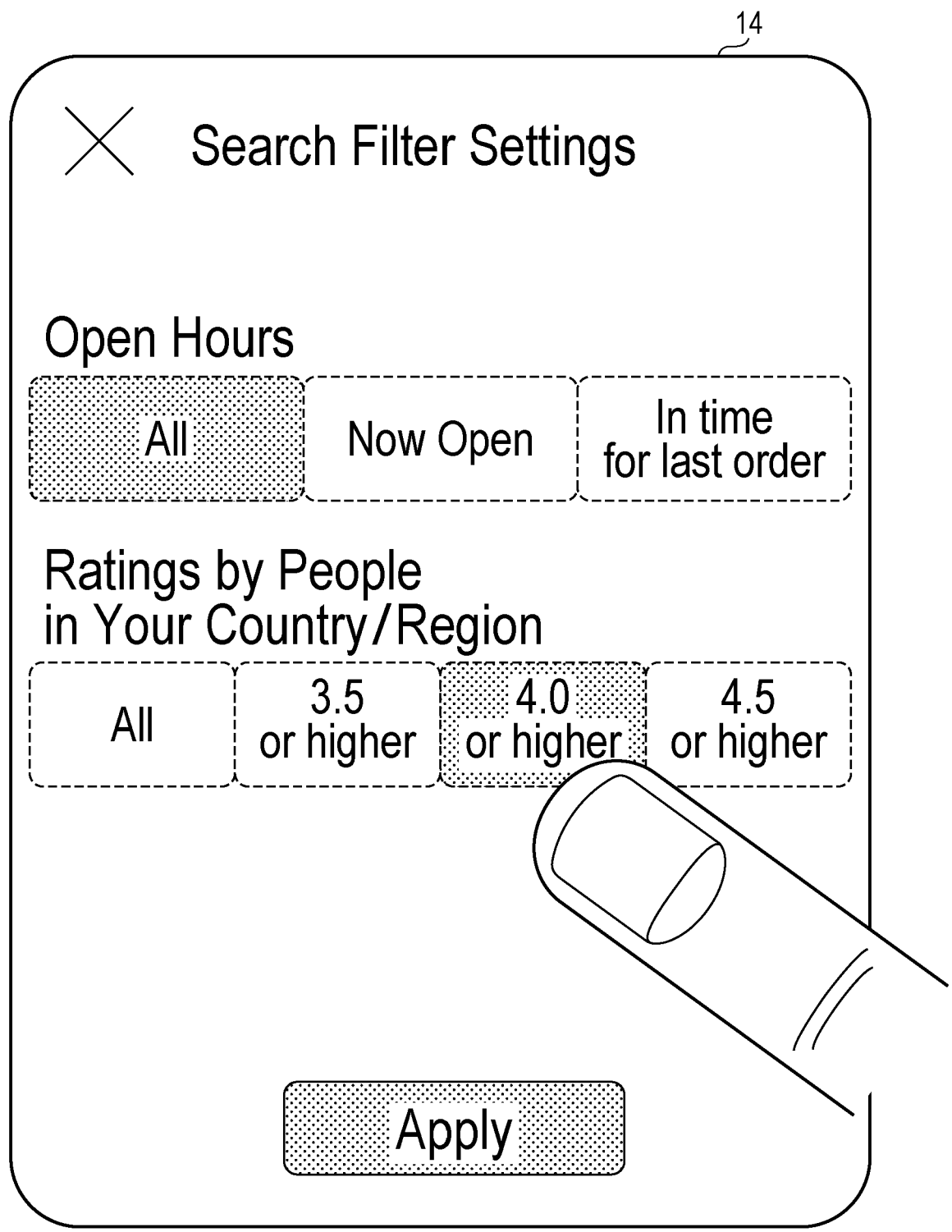
FIG. 34 is a view illustrating one example of a resident search filter displayed on the display of the communication terminal in the first modification of the third embodiment.

FIG. 34 is a view illustrating one example of the resident search filter displayed on the display 14 of the communication terminal 1 in the first modification of the third embodiment.

The search filter screen illustrated in FIG. 34 displays search filters that can be selected by the user. The search filter screen illustrated in FIG. 34 displays a search filter for specifying open hours and the resident search filter for filtering dishes or restaurants by using rating results of dishes or restaurants rated by residents in the same region or country as the user.

For example, when the resident search filter is specified during search for restaurants located near the user on the map, the management server 2 retrieves only restaurants highly rated by the residents in the same region or country as the user. The management server 2 may also make the user select dishes and/or restaurants that satisfy one rating result from among four rating results "all", "low rating", "average", and "high rating" of the residents in the same region or country as the user.

The management server 2 may also make the user select dishes and/or restaurants, based on five-level rating points (such as average points of the residents in the same region or country as the user), as illustrated in FIG. 34. In this case, when "All" is selected, all dishes and/or restaurants rated by the residents in the same region or country as the user are treated as search targets. When "3.5 or higher" is selected, all dishes and/or restaurants for which the average points of rating points (five-level ratings) of the residents in the same region or country as the user are 3.5 points or higher are treated as search targets. Also, when "4.0 or higher" is selected, all dishes and/or restaurants for which the average points of the rating points (five-level ratings) of the residents in the same region or country as the user are 4.0 points or higher are treated as search targets. Also, "4.5 or higher" is selected, all dishes and/or restaurants for which the average points of the rating points (five-level ratings) of the residents in the same region or country as the user are 4.5 points or higher are treated as search targets. Lastly, when an "Apply" button is pressed, the resident search filter becomes active, so that a search result screen on which the resident search filter is reflected is displayed.

The resident search filter is useful when the user goes to an unfamiliar region in the country where he or she lives or goes to a foreign country and wishes to have a dish rated to be delicious by people who live in the same region or country as the user.

Although the resident search filter that allows for setting of a condition regarding ratings on dishes or restaurants, the ratings being given by residents in the same country or region as the user, is provided in this case, the present disclosure is not particularly limited thereto. For example, an ON/OFF button for "Restaurants popular among Japanese" may be provided as the resident search filter.

Figure 35:
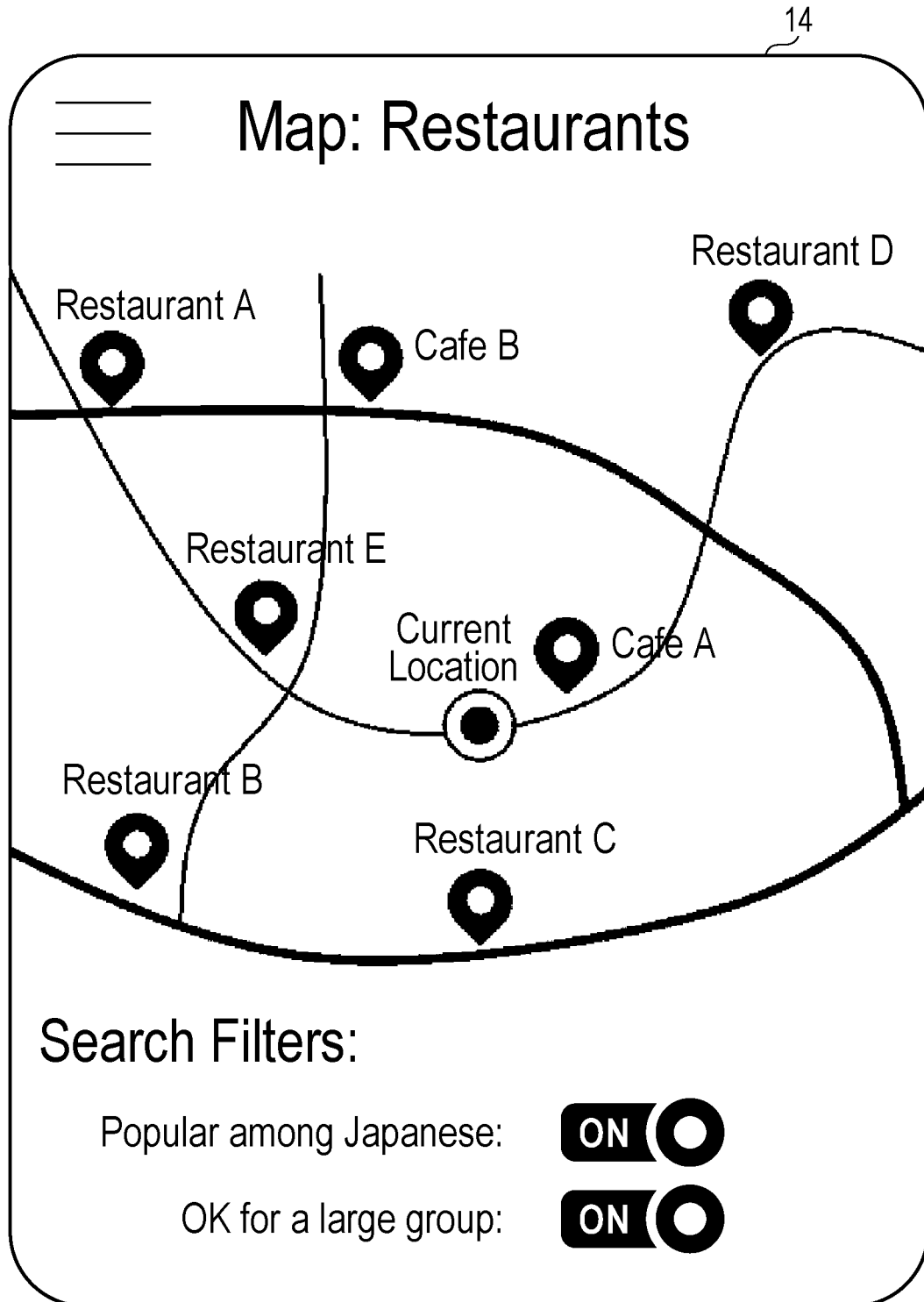
FIG. 35 is a view illustrating another example of a search result screen displayed on the display of the communication terminal in the first modification of the third embodiment.

FIG. 35 is a view illustrating another example of the search result screen displayed on the display 14 of the communication terminal 1 in the first modification of the third embodiment.

Although, in FIG. 34, the resident search filter is displayed on the screen different from the search result screen, the resident search filter illustrated in FIG. 35 is displayed superimposed on the search result screen.

As illustrated in FIG. 35, the display 14 may display, at a lower portion of the search result screen, a radio button for switching ON/OFF states of the resident search filter. When a radio button for "Popular among Japanese" is selected, only dishes and/or restaurants highly rated by Japanese people in the current location of the communication terminal 1 are displayed.

Also, although the resident search filter in the first modification of the third embodiment filters dishes or restaurants by using rating results of dishes or restaurants rated by residents in the same region or country as the user of the communication terminal 1, the present disclosure is not particularly limited thereto. The resident search filter may filter dishes or restaurants by using rating results of dishes or restaurants rated by sense-of-taste top scorers who reside in the same region or country as the user. That is, when the address indicated by the address information is included in a specific region, and the evaluation values of the user's sense of taste satisfy a certain condition for sense-of-taste top scorers who reside in the specific region, the rating information indicating the user's rating of a dish or a restaurant is included in rating results of dishes or restaurants rated by the sense-of-taste top scorers.

In this case, rather than merely selecting dishes or restaurants highly rated by residents in the same region or country as the user of the communication terminal 1, dishes or restaurants highly rated by sense-of-taste top scorers who reside in the same region or country as the user of the communication terminal 1 are selected. This allows the management server 2 to search for restaurants highly rated by people who have high taste sensitivities among the residents in the same region or country as the user.

Also, the resident search filter may filter dishes or restaurants by using rating results of dishes or restaurants rated by other users who reside in the same region or country as the user of the communication terminal 1 and who have sense-of-taste characteristics similar to that of the user. That is, rather than merely selecting dishes or restaurants rated by residents in the same region or country as the user of the communication terminal 1, dishes or restaurants highly rated by other users who reside in the same region or country as the user of the communication terminal 1 and who have sense-of-taste characteristics similar to that of the user are selected. This allows the management server 2 to search for restaurants highly rated by people who are included in the residents in the same region or country as the user and who have sense-of-taste characteristics similar to that of the user.

Subsequently, a description will be given of search processing for searching for dishes or restaurants in a second modification of the third embodiment.

In the third embodiment, the resident search filter is not automatically displayed when the user is in the region or country (e.g., Japan) where he or she resides. In contrast, in the second modification of the third embodiment, when the user moves to a region or country different from the region or country where he or she resides, the resident search filter is automatically displayed or becomes selectable.

Figure 36:
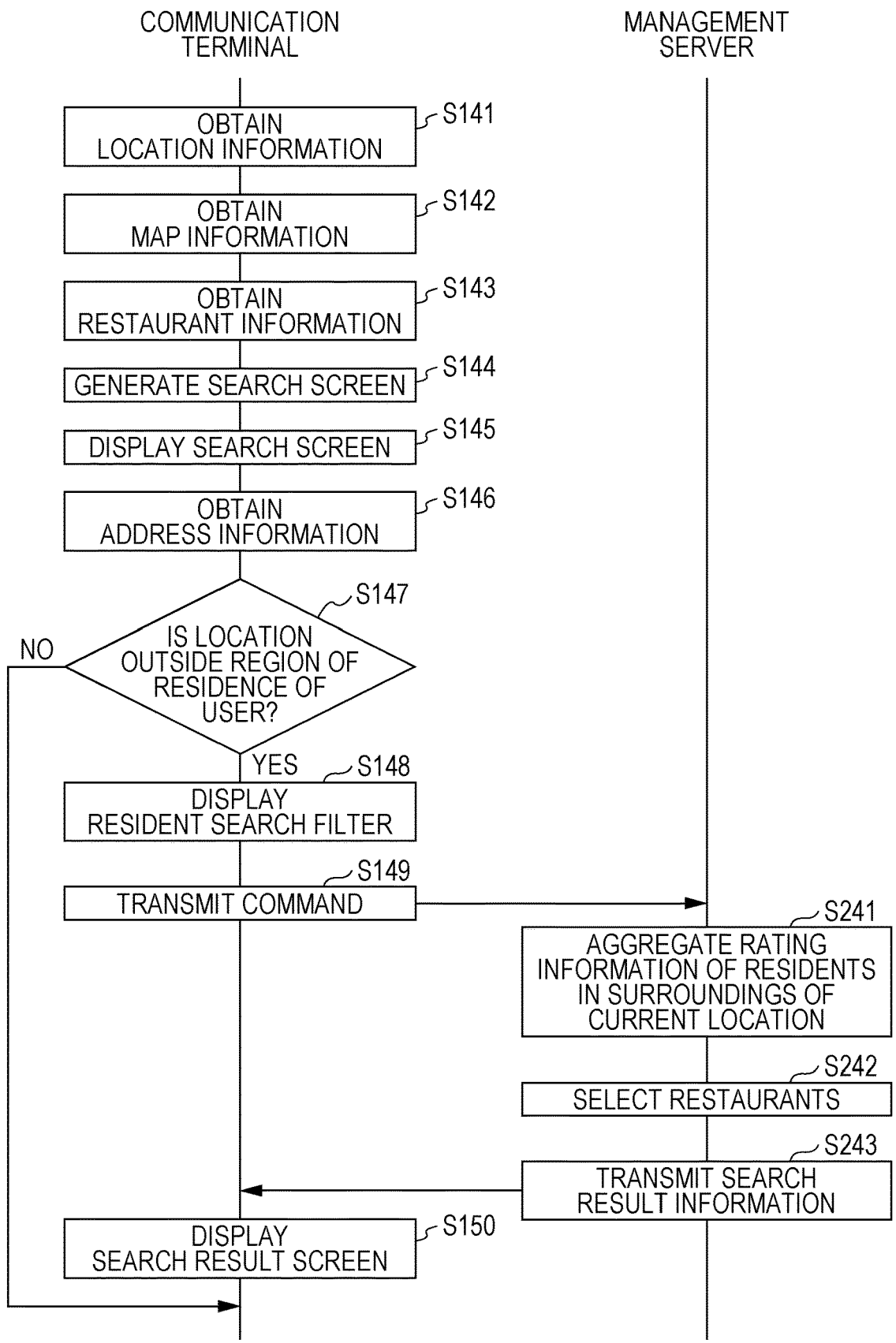
FIG. 36 is a sequence diagram illustrating one example of search processing in a second modification of the third embodiment of the present disclosure.

FIG. 36 is a sequence diagram illustrating one example of search processing in the second modification of the third embodiment of the present disclosure.

First, in step S141, the control unit 13 in the communication terminal 1 obtains location information indicating the location of the communication terminal 1. The control unit 13 obtains the location information from a location measurement unit (not illustrated) for measuring the current location of the communication terminal 1.

Next, in step S142, the communication unit 11 obtains map information including the location of the communication terminal 1 from the management server 2, from a map server (not illustrated) through the network 3, or from the memory 12 in the communication terminal 1. For obtaining the map information from the management server 2, the communication unit 11 issues a request for the map information including the location of the communication terminal 1 to the management server 2. In response to the request from the communication terminal 1, the management server 2 transmits the map information including the location of the communication terminal 1 to the communication terminal 1. Similarly, for obtaining the map information from the map server, the communication unit 11 issues a request for the map information including the location of the communication terminal 1 to the map server. In response to the request from the communication terminal 1, the map server transmits the map information including the location of the communication terminal 1 to the communication terminal 1. Similarly, for obtaining the map information from the memory 12, the control unit 13 uses the location information including the location of the communication terminal 1 to read the map information including the location of the communication terminal 1 from the memory 12.

Next, in step S143, the communication unit 11 obtains restaurant information indicating restaurants to be displayed in the map information. In this case, the communication unit 11 issues, to the management server 2, a request for the restaurant information indicating the restaurants to be displayed in the map information. In response to the request from the communication terminal 1, the management server 2 transmits, to the communication terminal 1, the restaurant information indicating the restaurants to be displayed in the map information.

Next, in step S144, based on the map information and the restaurant information, the control unit 13 generates a search screen on which the restaurants indicated by the restaurant information are shown on a map indicated by the map information. One search filter for filtering dishes or restaurants by using rating results of dishes or restaurants rated by residents in a region including a location indicated by the map information is displayed on the search screen as one of a plurality of search filters.

Next, in step S145, the control unit 13 causes the generated search screen to be displayed on the display 14.

Next, in step S146, the control unit 13 obtains address information indicating the region of residence of the user of the communication terminal 1. The address information is pre-stored in the memory 12. The user may input the address information by using the operation unit 15.

The order of steps S141 to S146 is not limited to the above-described order.

Next, in step S147, the control unit 13 decides whether or not the location indicated by the location information is outside the region of residence of the user.

When it is decided that the location is outside the region of residence of the user (YES in step S147), in step S148, the control unit 13 causes a resident search filter (a search filter) to be displayed on the display 14. When the location indicated by the location information is outside the country of residence of the user of the communication terminal 1, the control unit 13 decides that the location indicated by the location information is outside the region of residence.

Since processes in steps S149 and S150 and steps S241 to S243 are substantially the same as the processes in steps S126 and S127 and steps S223 to S225 in FIG. 31, descriptions thereof will not be given hereinafter.

On the other hand, when it is decided that the location is not outside the region of residence of the user, that is, the location is in the region of residence of the user (NO in step S147), the control unit 13 does not cause the resident search filter (the search filter) to be displayed on the display 14.

Although, in the second modification of the third embodiment, the processes in steps S141 to S148 are performed by the communication terminal 1, the present disclosure is not particularly limited thereto, and the processes may be performed by the management server 2. In this case, the control unit 23 in the management server 2 obtains the location information from the communication terminal 1, obtains the map information from the memory 22, and obtains the restaurant information from the memory 22 to generate a search screen. The control unit 23 transmits the generated search screen to the communication terminal 1 and causes the search screen to be displayed on the display 14 of the communication terminal 1. Also, the control unit 23 obtains the address information from the communication terminal 1 to decide whether or not the location indicated by the location information is outside the region of residence of the user. When it is decided that the location is outside the region of residence of the user, the control unit 23 transmits the resident search filter (the search filter) to the communication terminal 1 to cause the resident search filter to be displayed on the display 14 of the communication terminal 1. On the other hand, when it is decided that the location is not outside the region of residence of the user, that is, the location is in the region of residence of the user, the control unit 23 does not cause the resident search filter (the search filter) to be displayed on the display 14 of the communication terminal 1.

In the first modification of the third embodiment, the control unit 13 may automatically cause the resident search filter (the search filter) to be displayed when the location of the communication terminal 1 is outside the region of residence of the user, as in the second modification of the third embodiment.

According to the third embodiment, when the address indicated by the address information is included in a specific region, rating information indicating the user's rating of a dish or a restaurant is included in rating results of dishes or restaurants rated by residents in the specific region. One search filter for filtering the dishes or restaurants by using the rating results of the dishes or restaurants rated by the residents in the specific region is provided on the dish search screen as one of the plurality of search filters. Accordingly, the dishes or restaurants highly rated by the residents in the specific region can be presented to the user as a search result.

Also, dishes or restaurants are filtered by one search filter by using the rating results of the dishes or restaurants rated by the residents in the specific region, and a first restaurant that serves a dish filtered by one search filter or a second restaurant filtered by one search filter is displayed on the display 14 of the communication terminal 1. Accordingly, dishes or restaurants highly rated by the residents in the specific region can be presented to a first user as a search result.

Also, when the user's address is included in the specific region, the rating information indicating the user's rating of a dish or a restaurant is included in the rating results of the dishes or restaurants rated by the residents in the specific region. Accordingly, it is possible to filter dishes or restaurants by using the rating results of users who have addresses corresponding to the specific region.

In addition, when the location of the communication terminal 1 is outside the region of residence of the user, one search filter for filtering dishes or restaurants by using rating results of dishes or restaurants rated by residents in the region including the location indicated by the map information is automatically displayed on the display 14. Accordingly, it is possible to display one search filter on the search screen, without requesting the user to perform a special operation.

Although, in the description in FIG. 36, the map information and the restaurant information are obtained in advance in order to display the search screen, the present disclosure is not limited thereto. For example, a search screen that does not include the map information and the restaurant information may be adapted to be displayed. In this case, the communication terminal 1 may perform processing including: obtaining the location information (step S141); obtaining the address information (step S146); deciding whether or not the location is outside the region of residence of the user (step S147); determining that the resident search filter is to be displayed on the search screen, when the result indicates YES (step S148); determining that the resident search filter is not to be displayed on the search screen, when the result indicates NO; and displaying, on the display 14, a search screen for specifying a condition for searching for dishes or restaurants (step S145).

The description In FIG. 36 has been given of the resident search filter to which the third embodiment is applied. That is, although the resident search filter has been described as a search filter using rating results of dishes or restaurants rated by residents in the surroundings of the current location of the communication terminal 1, the present disclosure is not limited thereto. For example, the first modification of the third embodiment may also be applied. In this case, the resident search filter is a search filter using rating results of dishes or restaurants rated by users in the region or country of residence of the user of the communication terminal 1. Also, in this case, the processes in and after step S149 in FIG. 36 are replaced with the processes in and after step S135 in FIG. 33.

Fourth Embodiment

An information management system in a fourth embodiment provides a dish search screen. One search filter for filtering dishes or restaurants by using rating results of dishes or restaurants rated by a second user who has a sense-of-taste characteristic that is similar to that of a first user is provided on the dish search screen as one of a plurality of search filters.

Figure 37:
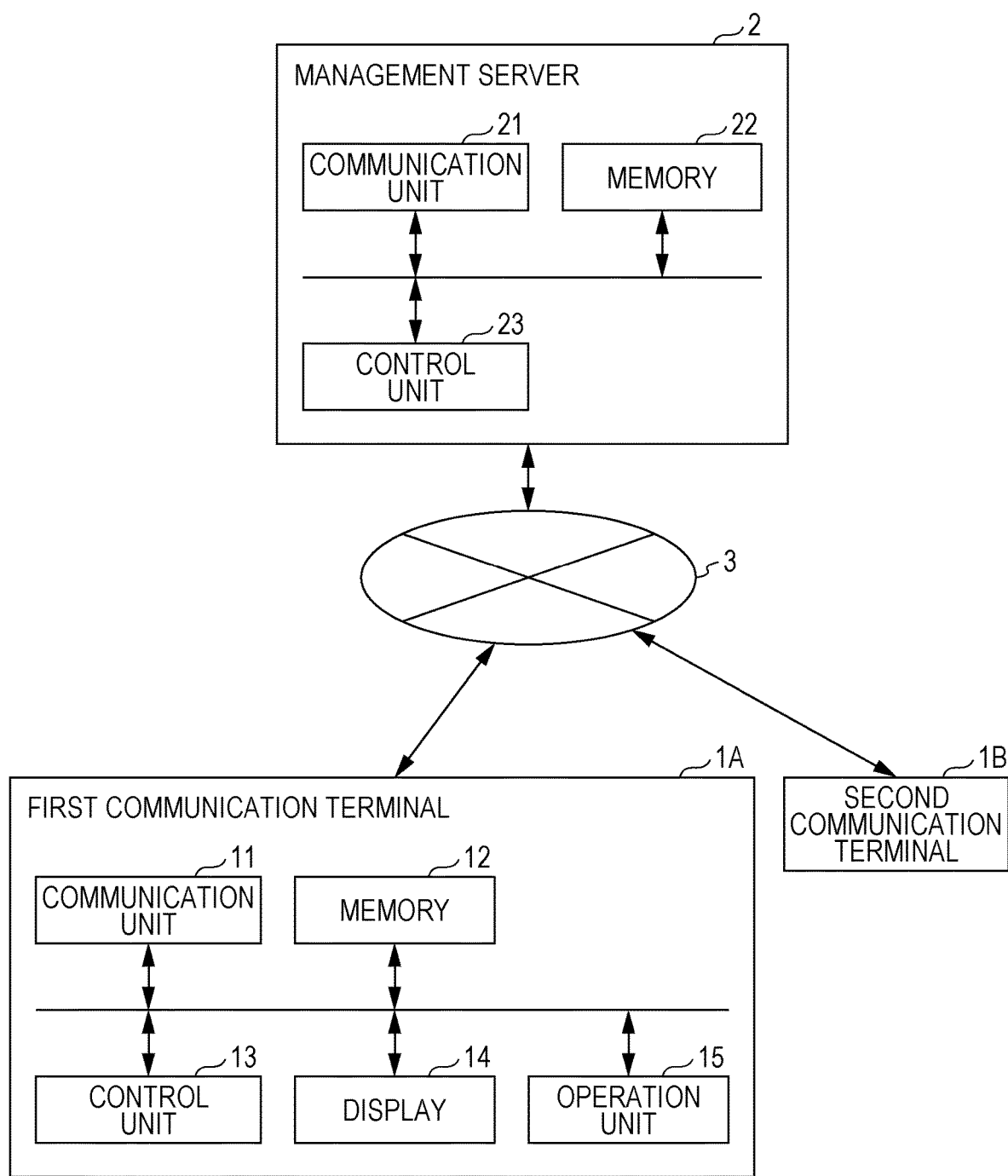
FIG. 37 is a diagram illustrating a configuration of an information management system in a fourth embodiment of the present disclosure.

FIG. 37 is a diagram illustrating a configuration of an information management system in the fourth embodiment of the present disclosure.

The information management system illustrated in FIG. 37 includes a first communication terminal 1A, a second communication terminal 1, and the management server 2.

The configurations of the first communication terminal 1A and the second communication terminal 1B are substantially the same as the configuration of the communication terminal 1 illustrated in FIG. 1. The first communication terminal 1A is used by a first user, and the second communication terminal 1B is used by a second user different from the first user.

The display 14 of the first communication terminal 1A displays the dish search screen. One search filter that filters dishes or restaurants by using rating results of dishes or restaurants rated by the second user who has a sense-of-taste characteristic that is similar to that of the first user is provided on the dish search screen as one of a plurality of search filters.

The operation unit 15 of the first communication terminal 1A receives the first user's rating of a dish or a restaurant. Also, the operation unit 15 of the first communication terminal 1A receives the first user's selection of one search filter via the dish search screen.

The communication unit 11 in the first communication terminal 1A transmits a command indicating that one search filter is selected to the management server 2.

The communication unit 11 in the second communication terminal 1B transmits rating information indicating the second user's rating of a dish or a restaurant to the management server 2.

The communication unit 21 in the management server 2 receives, from the first communication terminal 1A through the network 3, first data indicating input values in the measurement test regarding sense of taste of the first user of the first communication terminal 1A. The measurement test regarding the sense of taste is used in order to measure the first user's taste sensitivity to at least one type of taste.

Also, the communication unit 21 in the management server 2 obtains, from the second communication terminal 1B through the network 3, second data indicating input values in the measurement test regarding sense of taste of the second user of the second communication terminal 1B. The measurement test regarding the sense of taste is used in order to measure the second user's taste sensitivity to at least one type of taste.

The measurement tests regarding the sense of taste in the fourth embodiment may be performed as in the first embodiment.

That is, the input values in the measurement tests of taste resolutions of the first user and the second user are input at the first communication terminal 1A and the second communication terminal 1B, respectively, by using at least one of a first test meal group including a plurality of test meals corresponding to a plurality of levels ranging from a light sweet taste to a strong sweet taste or a second test meal group including a plurality of test meals corresponding to a plurality of levels ranging from a light salty taste to a strong salty taste. The communication unit 21 outputs a first instruction for making the first user and the second user input which of a first sweetness test meal and a second sweetness test meal is sweeter to the first communication terminal 1A and the second communication terminal 1B, the first sweetness test meal and the second sweetness test meal being included in the plurality of test meals included in the first test meal group and having therebetween a first level gap of two or more levels of a plurality of levels ranging from a light sweet taste to a strong sweet taste. The communication unit 21 obtains the first data and the second data as responses to the first instruction.

Also, the communication unit 21 outputs a second instruction for making the first user and the second user input which of a third sweetness test meal and a fourth sweetness test meal of the plurality of test meals included in the first test meal group is sweeter, separately from the first sweetness test meal and the second sweetness test meal, to the first communication terminal 1A and the second communication terminal 1, the third sweetness test meal and the fourth sweetness test meal having therebetween a second level gap that is narrower than the first level gap among the plurality of levels ranging from the light sweet taste to the strong sweet taste. When it is decided that the response to the first instruction indicates a correct answer, the communication unit 21 outputs the second instruction. The communication unit 21 obtains the first data and the second data as responses to the second instruction.

In addition, the communication unit 21 outputs a third instruction for making the first user and the second user input which of a fifth sweetness test meal and a sixth sweetness test meal of the plurality of the test meals included in the first test meal group is sweeter, separately from the first sweetness test meal and the second sweetness test meal, to the first communication terminal 1A and the second communication terminal 1B, the fifth sweetness test meal and the sixth sweetness test meal having therebetween a third level gap that is wider than the first level gap among the plurality of levels ranging from the light sweet taste to the strong sweet taste. When it is decided that the response to the first instruction indicates an incorrect answer, the communication unit 21 outputs the third instruction. The communication unit 21 obtains first data and second data as responses to the third instruction.

In the measurement tests regarding the sense of taste in the fourth embodiment, the measurement test of the taste resolution may also be performed as in the first embodiment. That is, the communication unit 21 may obtain the first data indicating input values in the measurement test of the taste resolution of the first user from the first communication terminal 1A through the network 3. The communication unit 21 may also obtain the second data indicating input values in the measurement test of the taste resolution of the second user from the second communication terminal 1B through the network 3. The control unit 23 may generate a first evaluation value of the first user's sense of taste, based on the first data. Also, the control unit 23 may generate a second evaluation value of the second user's sense of taste, based on the second data.

In the measurement tests regarding the sense of taste in the fourth embodiment, the measurement test of the taste resolution and/or the measurement test of the taste sensing threshold may be performed as in the first modification of the first embodiment. That is, the communication unit 21 may obtain third data indicating input values in the measurement test of the taste sensing threshold of the first user from the first communication terminal 1A through the network 3. Also, the communication unit 21 may obtain fourth data indicating input values in the measurement test of the taste sensing threshold of the second user from the second communication terminal 1B through the network 3. The control unit 23 may generate a first evaluation value of the first user's sense of taste, based on the first data and/or the third data. The control unit 23 may also generate a second evaluation value of the second user's sense of taste, based on the second data and/or the fourth data.

Also, the input value in the measurement test of the taste sensing threshold of the first user and the input value in the measurement test of the taste sensing threshold of the second user are input at the first communication terminal 1A and the second communication terminal 1B, respectively, by using at least a first test meal group including a plurality of test meals corresponding to a plurality of levels ranging from a light sweet taste to a strong sweet taste, a second test meal group including a plurality of test meals corresponding to a plurality of levels ranging from a light salty taste to a strong salty taste, and a third test meal group including a plurality of tasteless test meals. The communication unit 21 may output, to the first communication terminal 1A and the second communication terminal 1B, a fourth instruction for making the first user and the second user use the first test meal group, the second test meal group, and the third test meal group to input whether the test meals included in the first test meal group or the second test meal are tasteless or not tasteless in order with a level of a lightest taste first. The communication unit 21 may obtain the third data and the fourth data as responses to the fourth instruction.

Also, in the measurement tests regarding the sense of taste in the fourth embodiment, the measurement test of the taste resolution and/or the measurement test of the taste recognition threshold may be performed as in the second modification of the first embodiment. That is, the communication unit 21 may obtain, from the first communication terminal 1A through the network 3, fifth data indicating input values in the measurement test of the taste recognition threshold of the first user. The communication unit 21 may also obtain, from the second communication terminal 1B through the network 3, sixth data indicating input values in the measurement test of the taste recognition threshold of the second user. The control unit 23 may generate a first evaluation value of the first user's sense of taste, based on the first data and/or the fifth data. The control unit 23 may generate a second evaluation value of the second user's sense of taste, based on the second data and/or the sixth data.

Also, the input values in the measurement tests of the taste recognition thresholds of the first user and the second user are input at the first communication terminal 1A and the second communication terminal 1B, respectively, by using at least a first test meal group including a plurality of test meals corresponding to a plurality of levels ranging from a light sweet taste to a strong sweet taste and a second test meal group including a plurality of tasteless test meals. The communication unit 21 may output, to the first communication terminal 1A and the second communication terminal 1B, a fifth instruction for making the first user and the second user use the first test meal group and the second test meal group to input whether the test meals included in the first test meal group have no taste or have sweet taste in order with the level of a lightest sweet taste first. The communication unit 21 may obtain the fifth data and the sixth data as responses to the fifth instruction.

Also, in the measurement tests regarding the sense of taste in the fourth embodiment, the measurement test of the taste resolution and/or measurement test of the taste density may also be performed as in the third modification of the first embodiment. That is, the communication unit 21 may obtain, from the first communication terminal 1A through the network 3, seventh data indicating input values in the measurement test of the taste density of the first user. The communication unit 21 may also obtain, from the second communication terminal 1B through the network 3, eighth data indicating input values in the measurement test of the taste density of the second user. The control unit 23 may generate a first evaluation value of the first user's sense of taste, based on the first data and/or the seventh data. The control unit 23 may generate a second evaluation value of the second user's sense of taste, based on the second data and/or the eighth data.

Also, the input values in the measurement tests of the taste density of the first user and the second user are input at the first communication terminal 1A and the second communication terminal 1B, respectively, by using at least a first test meal group including a plurality of test meals corresponding to a plurality of levels ranging from a light sweet taste to a strong sweet taste. The communication unit 21 may output, to the first communication terminal 1A and the second communication terminal 1B, a sixth instruction for making the first user and the second user use the first test meal group to input at least three test meals in order of density of taste, the at least three test meals being included in the plurality of test meals included in the first test meal group. The communication unit 21 may obtain the seventh data and the eighth data as responses to the sixth instruction.

Also, the communication unit 21 obtains, from the second communication terminal 1B, rating information indicating the second user's rating of a dish or a restaurant. The rating information indicating the second user's rating of the dish or restaurant is included in the second user's rating results of dishes or restaurants.

Also, the communication unit 21 obtains, from the first communication terminal 1A through the network 3, a command indicating that one search filter is selected.

Based on the first data, the control unit 23 generates a first evaluation value of the first user's sense of taste in association with the first user. Based on the second data, the control unit 23 generates a second evaluation value of the second user's sense of taste in association with the second user.

When the first user uses one search filter to filter dishes or restaurants, and a first difference between the first evaluation value and the second evaluation value is in a first predetermined range, the control unit 23 filters the dishes or the restaurants by using the second user's rating result.

The first evaluation value is an evaluation value for the first user's taste sensitivity to at least one type of taste, and the second evaluation value is an evaluation value for the second user's taste sensitivity to at least one type of taste. The at least one type of taste is at least one of sweetness, sourness, saltiness, bitterness, and umami.

Also, the first evaluation value may be represented by a first value indicating sensitivity to a first type of taste and a second value indicating sensitivity to a second type of taste, the first type of taste and the second type of taste being included in at least two types of taste of five types of taste, that is, sweetness, sourness, saltiness, bitterness, and umami. The second evaluation value may also be represented by a third value indicating sensitivity to the first type of taste and a fourth value indicating sensitivity to the second type of taste. When a second difference between the first value and the third value and a third difference between the second value and the fourth value are both in a second predetermined range, the control unit 23 may decide that the first difference between the first evaluation value and the second evaluation value is in the first predetermined range.

The first evaluation value may also be represented as a first evaluation vector having a number of dimensions greater than or equal to two dimensions constituted by a first value indicating sensitivity to a first type of taste and a second value indicating sensitivity to a second type of taste, the first type of taste and the second type of taste being included in at least two types of taste of five types of taste, that is, sweetness, sourness, saltiness, bitterness, and umami. Similarly, the second evaluation value may be represented as a second evaluation vector having a number of dimensions greater than two dimensions constituted by a third value indicating sensitivity to the first type of taste and a fourth value indicating sensitivity to the second type of taste, the first type of taste and the second type of taste being included in at least two types of taste of the five types of taste, that is, sweetness, sourness, saltiness, bitterness, and umami. The degree of similarity between the first evaluation vector and the second evaluation vector is calculated using the inner product of the vectors, the cosine similarity thereof, or the like, and when a first degree of similarity resulting from the calculation is in a first predetermined range of the degree of similarity, the control unit 23 may decide that the first difference between the first evaluation value and the second evaluation value is in the first predetermined range.

Also, based on a command obtained by the communication unit 21, the control unit 23 selects at least one dish filtered by one search filter or at least one restaurant filtered by one search filter. Based on a command obtained by the communication unit 21, the control unit 23 selects a first restaurant that serves a dish filtered by one search filter or a second restaurant filtered by one search filter.

The communication unit 21 outputs information indicating the selected at least one dish or restaurant to the first communication terminal 1A through the network 3 in order to display the information on the display 14 of the first communication terminal 1A. The communication unit 21 outputs information indicating the selected first restaurant that serves the dish or the second restaurant to the first communication terminal 1A through the network 3 in order to display the information on the display 14 of the first communication terminal 1A.

The filtering in this case means only dishes or restaurants highly rated by the second user for whom the first difference between the first evaluation value and the second evaluation value is in the first predetermined range and who is determined to have a sense-of-taste characteristic similar to that of the first user are treated as search targets of the first user.

Subsequently, a description will be given of sense-of-taste evaluation processing for evaluating the first user's sense of taste and the second user's sense of taste in the fourth embodiment of the present disclosure.

Figure 38:
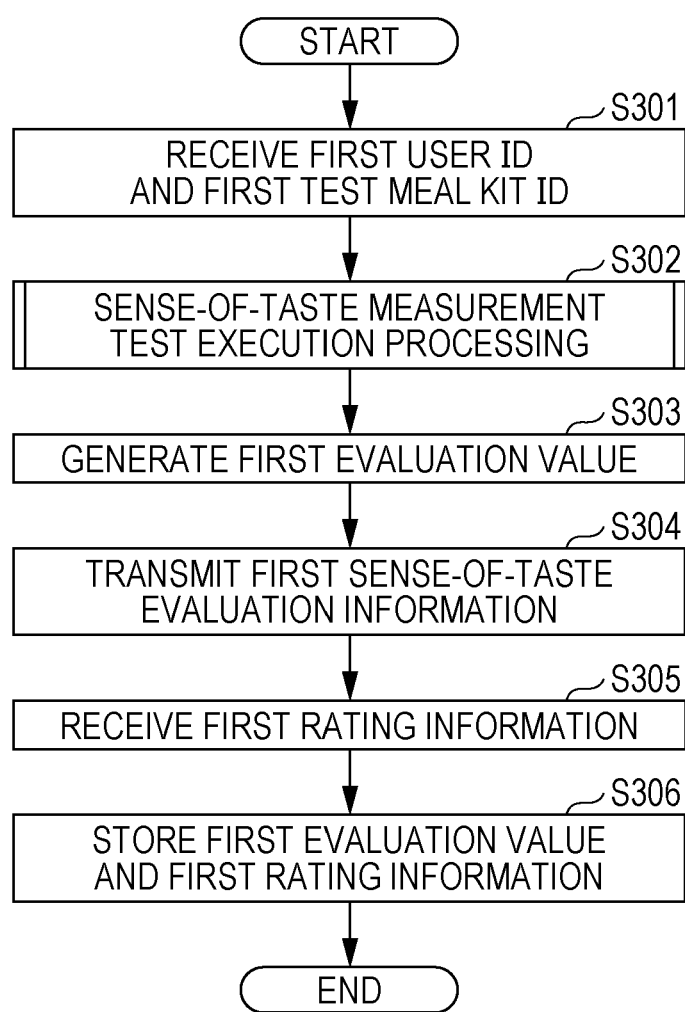
FIG. 38 is a flowchart illustrating sense-of-taste evaluation processing on a first user, the processing being performed by the management server in the fourth embodiment of the present disclosure.

FIG. 38 is a flowchart illustrating sense-of-taste evaluation processing on the first user, the processing being performed by the management server in the fourth embodiment of the present disclosure.

First, in step S301, the communication unit 21 receives a first user ID and a first test meal kit ID transmitted by the first communication terminal 1A. In this case, the first communication terminal 1A receives the first user's inputs of the first test meal kit ID printed on a test meal kit and the first user ID. The first communication terminal 1A displays an input screen, provided by the management server 2, on a web browser and receives inputs of the first user ID and the first test meal kit ID via the input screen. The first communication terminal 1A transmits the input first user ID and first test meal kit ID to the management server 2.

Next, in step S302, the control unit 23 executes the sense-of-taste measurement test execution processing. In the sense-of-taste measurement test execution processing, a sense-of-taste measurement test for measuring the first user's sense of taste is generated, and also first data indicating input values in the sense-of-taste measurement test is generated. In this case, in the sense-of-taste measurement test, with respect to at least one taste component, a determination may be made using one or more taste sensitivity measurement tests of the taste resolution, the taste sensing threshold, the taste recognition threshold, the taste density, and the taste mixture, which are described above in the first embodiment. In addition, even with a method different from the measurement tests regarding the sense of taste described in the present disclosure, the present disclosure can be similarly applied as long as it is a measurement test regarding taste which can determine a sense-of-taste characteristic.

Next, in step S303, based on the first data, the control unit 23 generates a first evaluation value of the first user's sense of taste in association with the first user.

Next, in step S304, the control unit 23 transmits first sense-of-taste evaluation information indicating the generated first evaluation value to the first communication terminal 1A. The communication unit 11 in the first communication terminal 1A receives the first sense-of-taste evaluation information transmitted by the management server 2. The display 14 of the first communication terminal 1A then displays the first sense-of-taste evaluation information received by the communication unit 11.

Next, in step S305, the communication unit 21 receives, from the first communication terminal 1A, first rating information indicating the first user's rating of a dish or a restaurant. In this case, each dish or restaurant is rated, for example, in five levels. The operation unit 15 of the first communication terminal 1A receives the first user's rating of the dish or the restaurant. The first user gives points, for example, 5 points to 1 point, to each dish or restaurant. Five points is the best, and 1 point is the worst. The communication unit 11 in the first communication terminal 1A transmits the first rating information to the management server 2.

Next, in step S306, the control unit 23 stores the generated first evaluation value and the received first rating information in the memory 22 in association with the first user ID.

Figure 39:
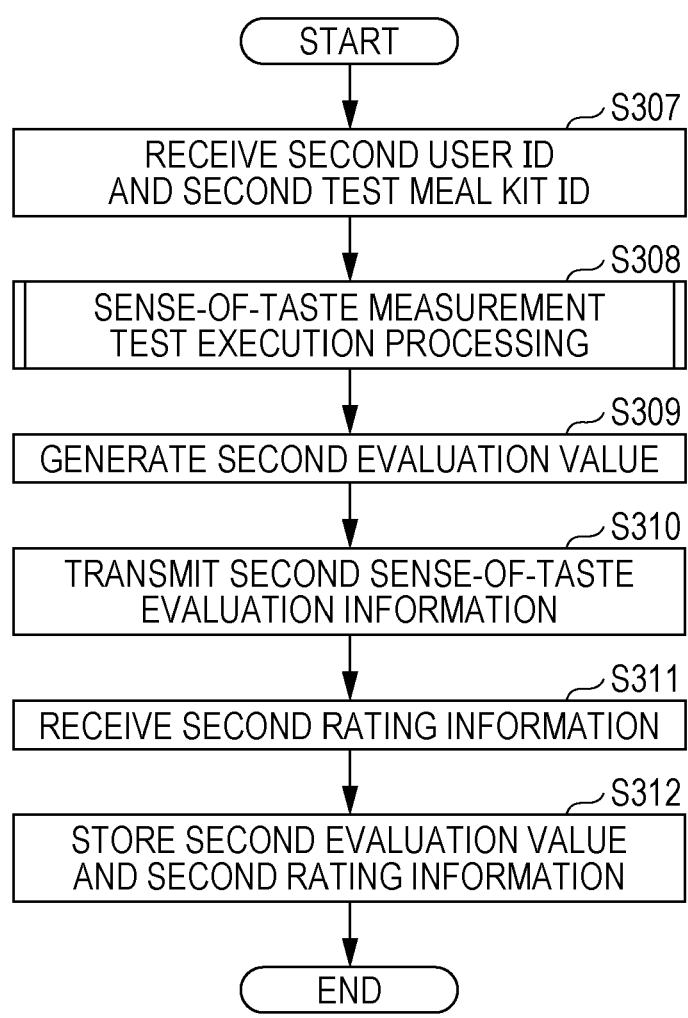
FIG. 39 is a flowchart illustrating sense-of-taste evaluation processing on a second user, the processing being performed by the management server in the fourth embodiment of the present disclosure.

FIG. 39 is a flowchart illustrating sense-of-taste evaluation processing on the second user, the processing being performed by the management server in the fourth embodiment of the present disclosure.

First, in step S307, the communication unit 21 receives a second user ID and a second test meal kit ID transmitted by the second communication terminal 1B. In this case, the second communication terminal 1B receives the second user's inputs of the second test meal kit ID printed on a test meal kit and the second user ID. The second communication terminal 1B displays an input screen, provided by the management server 2, on a web browser and receives inputs of the second user ID and the second test meal kit ID via the input screen. The second communication terminal 1B transmits the input second user ID and second test meal kit ID to the management server 2.

Next, in step S308, the control unit 23 executes the sense-of-taste measurement test execution processing. In the sense-of-taste measurement test execution processing, a sense-of-taste measurement test for measuring the second user's sense of taste is generated, and also second data indicating input values in the sense-of-taste measurement test is generated. In this case, in the sense-of-taste measurement test, with respect to at least one taste component, a determination may be made using one or more taste sensitivity measurement tests of the taste resolution, the taste sensing threshold, the taste recognition threshold, the taste density, and the taste mixture, which are described above in the first embodiment. In addition, even with a method different from the measurement tests regarding the sense of taste described in the present disclosure, the present disclosure can be similarly applied as long as it is a measurement test regarding taste which can determine a sense-of-taste characteristic.

Next, in step S309, based on the second data, the control unit 23 generates a second evaluation value of the second user's sense of taste in association with the second user.

Next, in step S310, the control unit 23 transmits second sense-of-taste evaluation information indicating the generated second evaluation value to the second communication terminal 1B. The communication unit 11 in the second communication terminal 1B receives the second sense-of-taste evaluation information transmitted by the management server 2. The display 14 in the second communication terminal 1B then displays the second sense-of-taste evaluation information received by the communication unit 11.

Next, in step S311, the communication unit 21 receives, from the second communication terminal 1B, second rating information indicating the second user's rating of a dish or a restaurant. In this case, each dish or restaurant is rated, for example, in five levels. The operation unit 15 of the second communication terminal 1B receives the second user's rating of the dish or restaurant. The second user gives points, for example, 5 points to 1 point, to each dish or restaurant. Five points is the best, and 1 point is the worst. The communication unit 11 in the second communication terminal 1B transmits the second rating information to the management server 2.

Next, in step S312, the control unit 23 stores the generated second evaluation value and the received second rating information in the memory 22 in association with the second user ID.

In the sense-of-taste measurement tests in the fourth embodiment, the taste-resolution measurement test in step S2 in FIG. 4 may also be performed as step S302 in FIG. 38 and S308 in FIG. 39, as in the first embodiment. Since the taste-resolution measurement test execution processing in the fourth embodiment is substantially the same as that in the first embodiment, a description thereof will not be given hereinafter.

In the sense-of-taste measurement tests in the fourth embodiment, the measurement test of the taste resolution and/or the measurement test of the taste sensing threshold may also be performed as in the first modification of the first embodiment. In this case, the taste-resolution measurement test execution processing in step S2 in FIG. 4 and/or the taste-sensing-threshold measurement test execution processing in step S6 in FIG. 9 are/is performed in step S302 in FIG. 38 and step S308 in FIG. 39. Since the taste-sensing-threshold measurement test execution processing in the fourth embodiment is substantially the same as that in the first modification of the first embodiment, a description thereof will not be given hereinafter.

In the sense-of-taste measurement tests in the fourth embodiment, the measurement test of the taste resolution and/or the measurement test of the taste recognition threshold may also be performed as in the second modification of the first embodiment. In this case, the taste-resolution measurement test execution processing in step S2 in FIG. 4 and/or the taste-recognition-threshold measurement test execution processing in step S8 in FIG. 12 are/is performed in step S302 in FIG. 38 and step S308 in FIG. 39. Since the taste-recognition-threshold measurement test execution processing in the fourth embodiment is substantially the same as that in the second modification of the first embodiment, a description thereof will not be given hereinafter.

In the sense-of-taste measurement test in the fourth embodiment, the measurement test of the taste resolution and/or the measurement test of the taste density may also be performed as in the third modification of the first embodiment. In this case, the taste-resolution measurement test execution processing in step S2 in FIG. 4 and/or the taste-density measurement test execution processing in step S10 in FIG. 15 are/is performed in step S302 in FIG. 38 and step S308 in FIG. 39. Since the taste-density measurement test execution processing in the fourth embodiment is substantially the same as that in the third modification of the first embodiment, a description thereof will not be given hereinafter.

In the sense-of-taste measurement test in the fourth embodiment, the measurement test of the taste mixture may also be performed as in the fourth modification of the first embodiment. In this case, the taste mixture measurement test execution processing in step S2 in FIG. 4 is performed in step S302 in FIG. 38 and step S308 in FIG. 39. Since the taste mixture measurement test execution processing in the fourth embodiment is substantially the same as that in the fourth modification of the first embodiment, a description thereof will not be given hereinafter.

In addition, at least one of the measurement test of the taste resolution in the first embodiment, the measurement test of the taste sensing threshold in the first modification of the first embodiment, the measurement test of the taste recognition threshold in the second modification of the first embodiment, the measurement test of the taste density in the third modification of the first embodiment, and the measurement test of the taste mixture in the fourth modification of the first embodiment may be performed in the sense-of-taste measurement test in the fourth embodiment.

Also, in the sense-of-taste evaluation processing on the first user in FIG. 38, the process in steps S305 in which the first rating information is received and the process in steps S306 in which the received first rating information is stored in the memory 22 may be performed at different timings. In the sense-of-taste evaluation processing on the second user in FIG. 39, the process in steps S311 in which the second rating information is received and the process in steps S312 in which the received second rating information is stored in the memory 22 may be performed at different timings.

Subsequently, a description will be given of search processing for searching for dishes or restaurants in the fourth embodiment.

Figure 40:
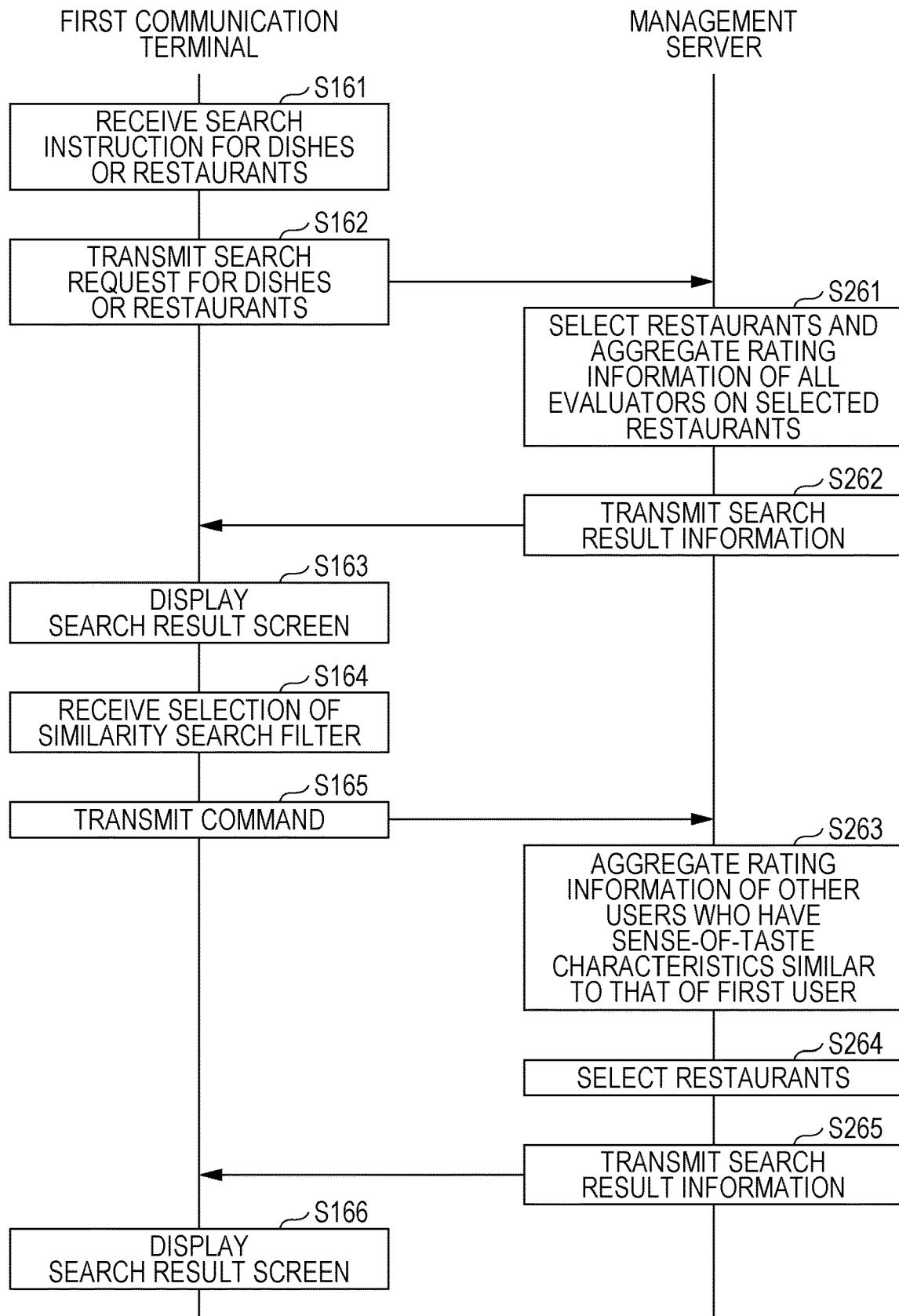
FIG. 40 is a sequence diagram illustrating one example of search processing in the fourth embodiment of the present disclosure.

FIG. 40 is a sequence diagram illustrating one example of the search processing in the fourth embodiment of the present disclosure. The search processing performed between the first communication terminal 1A and the management server 2 will be described with reference to FIG. 40.

Since processes in steps S161 to S163, S261, and S262 illustrated in FIG. 40 are substantially the same as the processes in steps S111 to S113, S211, and S212 illustrated in FIG. 25, descriptions thereof will not be given hereinafter.

In step S164, the operation unit 15 receives the user's selection of a similarity search filter from among a plurality of search filters. The similarity search filter filters dishes or restaurants by using rating results of dishes or restaurants rated by other users who have sense-of-taste characteristics that are similar to that of the first user. The other users include the second user. For example, the first user selects the similarity search filter by performing sound input, text input, or operation of a GUI displayed on the display 14 of the first communication terminal 1A. The plurality of search filters may include, in addition to the similarity search filter, for example, a search filter for filtering with a type of dish, a search filter for filtering with an average price spent at restaurants, and a search filter for filtering with open hours.

Next, in step S165, the communication unit 11 transmits a command indicating that the similarity search filter is selected to the management server 2. The communication unit 21 in the management server 2 receives the command transmitted by the first communication terminal 1A.

Next, in step S263, the control unit 23 aggregates rating information of the other users who have sense-of-taste characteristics similar to that of the first user. The control unit 23 calculates averages of rating points of the other users who have rated dishes and/or restaurants in the surroundings of the current location of the first communication terminal 1A and who have sense-of-taste characteristics similar to that of the first user.

Next, in step S264, the control unit 23 selects, from among the dishes and/or restaurants in the surroundings of the current location of the first communication terminal 1A, dishes and/or restaurants for which the averages of the rating points of the other users who have sense-of-taste characteristics similar to that of the first user are larger than or equal to a predetermined value.

Next, in step S265, the communication unit 21 transmits search result information including information regarding the selected dishes and/or restaurants to the first communication terminal 1A. The communication unit 11 in the first communication terminal 1A receives the search result information transmitted by the management server 2.

Next, in step S166, the display 14 displays a search result screen showing a filtering result obtained with the similarity search filter. Only the dishes and/or restaurants filtered by the similarity search filter are displayed on the search result screen. That is, of the dishes and/or restaurants in the surroundings of the current location of the user, only the dishes and/or restaurants for which the averages of the rating points of the other users who have sense-of-taste characteristics similar to that of the first user are larger than or equal to the predetermined value are displayed on the search result screen.

Although the above description has been given of a case in which dishes and/or restaurants in the surroundings of the current location of the user are searched, the present disclosure is not limited thereto. For example, dishes served by restaurants included in a map displayed on the display 14 of the first communication terminal 1A and/or restaurants included in the map may be treated as search targets. Alternatively, dishes of a dish type (e.g., Japanese dish) specified by the user and/or restaurants that serve the dishes may be treated as search targets.

Figure 41:
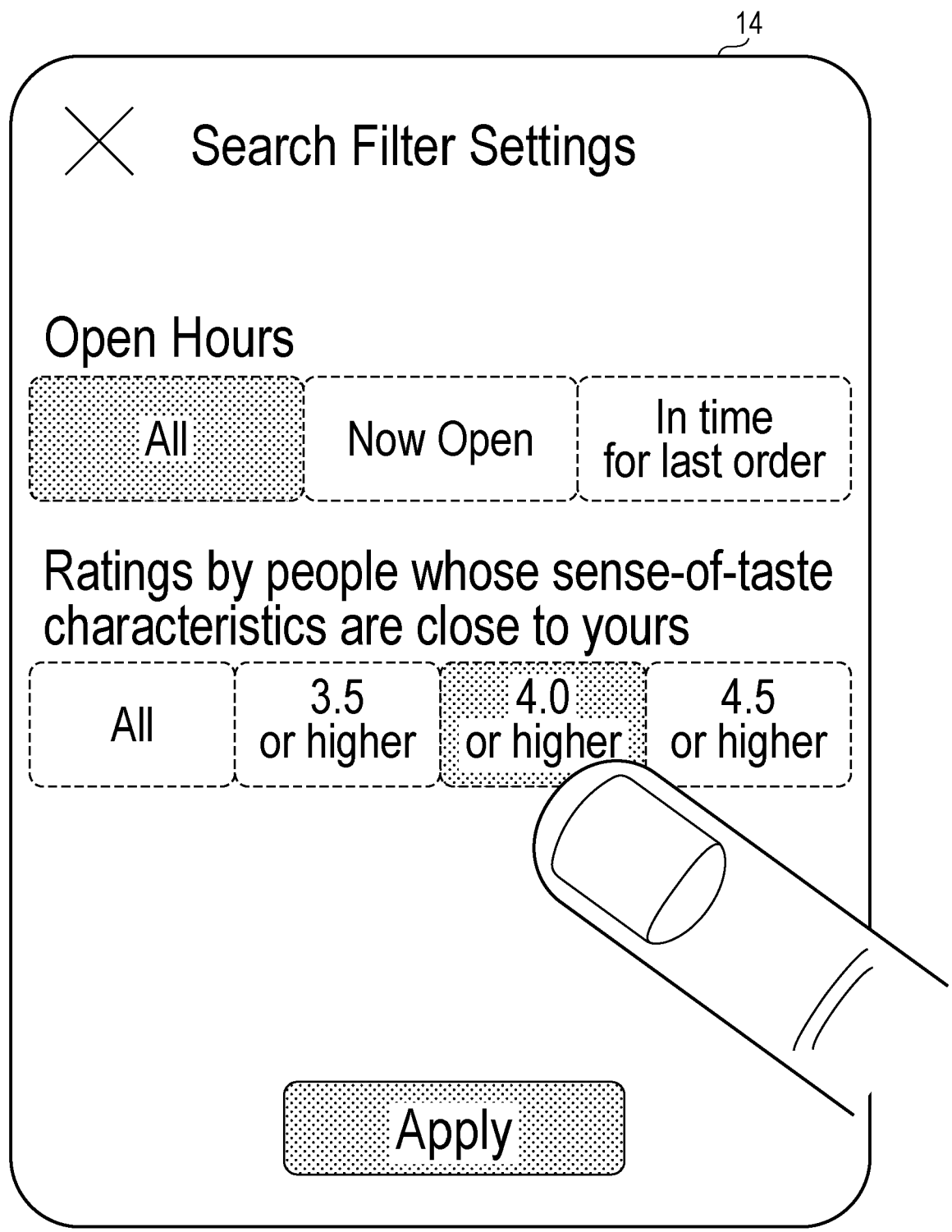
FIG. 41 is a view illustrating one example of a similarity search filter displayed on a display of a first communication terminal in the fourth embodiment.

FIG. 41 is a view illustrating one example of the similarity search filter displayed on the display of the first communication terminal in the fourth embodiment.

The search filter screen illustrated in FIG. 41 displays other search filters that can be selected by the user. One search filter for specifying open hours and the similarity search filter for searching for dishes or restaurants by using the rating results of dishes or restaurants rated by the other users who have sense-of-taste characteristics similar to that of the first user are displayed on the search filter screen illustrated in FIG. 41.

For example, when the similarity search filter is specified during search for restaurants located near the user on the map, the management server 2 retrieves only restaurants highly rated by the other users who have sense-of-taste characteristics similar to that of the first user.

The management server 2 may make the user select restaurants that satisfy one rating result from among four rating results "all", "low rating", "average", and "high rating" of the other users who have sense-of-taste characteristics to that of the first user.

The management server 2 may also make the user select dishes and/or restaurants, based on five-level rating points (such as average points of the other users who have sense-of-taste characteristics similar to that of the first user), as illustrated in FIG. 41. In this case, when "All" is selected, all dishes and/or restaurants rated by the other users who have sense-of-taste characteristics similar to that of the first user are treated as search targets. When "3.5 or higher" is selected, all dishes and/or restaurants for which the average points of rating points (five-level ratings) of the other users who have sense-of-taste characteristics similar to that of the first user are 3.5 points or higher are treated as search targets. Also, when "4.0 or higher" is selected, all dishes and/or restaurants for which the average points of the rating points (five-level ratings) of the other users who have sense-of-taste characteristics similar to that of the first user are 4.0 points or higher are treated as search targets. Also, when "4.5 or higher" is selected, all dishes and/or restaurants for which the average points of the rating points (five-level ratings) of the other users who have sense-of-taste characteristics similar to that of the first user are 4.5 points or higher are treated as search targets. Lastly, when an "Apply" button is pressed, the similarity search filter becomes active, so that a search result screen on which the similarity search filter is reflected is displayed.

The similarity search filter searches for restaurants highly rated by the other users who have sense-of-taste characteristics similar to that of the first user. The management server 2 selects the restaurants highly rated by the other users who have sense-of-taste characteristics similar to that of the first user and presents the selected restaurants to the first communication terminal 1A. The first communication terminal 1A can make a response to the user's search request by displaying only the retrieved dishes and/or restaurants.

The other users who have sense-of-taste characteristics similar to that of the first user may be other users whose amounts of difference from the evaluation points of the first user in the taste sensitivity (e.g., the taste recognition threshold) to at least one taste in the taste test are smaller than or equal to a predetermined amount. Also, the other users who have sense-of-taste characteristics similar to that of the first user may be other users whose amounts of difference in the sense-of-taste scores from the first user are smaller than or equal to a predetermined amount. Also, each sense-of-taste characteristic may be represented by a five-dimensional vector representing the sense-of-taste scores for five taste components, that is, sweetness, saltiness, sourness, bitterness, and umami. When the sense-of-taste characteristics are represented by vectors in such a manner, the degree of similarity between the sense-of-taste characteristics can be easily determined utilizing the inner product of the vectors or the cosine similarity thereof.

According to the fourth embodiment, when the first user uses one search filter to filter dishes or restaurants, and the first difference between the first evaluation value of the first user's sense of taste and the second evaluation value of the second user's sense of taste is in the first predetermined range, the second user's rating result is used to filter the dishes or the restaurants. Accordingly, dishes or restaurants highly rated by the second user who has a sense-of-taste characteristic similar to that of the first user can be presented to the first user as a search result.

Also, dishes or restaurants are filtered by one search filter by using rating results of dishes or restaurants rated by the second user who has a sense-of-taste characteristic similar to that of the first user, and a first restaurant that serves a dish filtered by one search filter or a second restaurant filtered by one search filter are displayed on the display 14 of the first communication terminal 1A. Accordingly, dishes or restaurants highly rated by the second user who has a sense-of-taste characteristic similar to that of the first user can be presented to the first user as a search result.

In addition, when the first difference between the first evaluation value and the second evaluation value is in the first predetermined range, dishes or restaurants are filtered using the second user's rating result. Accordingly, dishes or restaurants can be filtered using rating results of the second user who has a sense-of-taste characteristic similar to that of the first user.

Also, although, in the first to fourth embodiments, the management server 2 manages the user information, the map information, and the restaurant information, the present disclosure is not particularly limited thereto. The information management system may further include a server for managing the user information, a server for managing the map information, and a server for managing the restaurant information.

In each embodiment described above, each constituent element may be implemented by dedicated hardware or may be realized by executing a software program that suits each constituent element. A program executing unit, such as a CPU or a processor, may read and execute a software program recorded in a recording medium, such as a hard disk or a semiconductor memory, to thereby realize each constituent element. Also, the program may be recorded to a recording medium and be transported or may be transmitted through a network, and the program may be executed by another independent computer system.

Some or all of the functions of the devices according to the embodiments of the present disclosure are typically realized as a large-scale integration (LSI), which is an integrated circuit. Those functions may be individually realized by single chips or may be realized by a single chip so as to include some or all of the functions. Also, the circuit integration is not limited to LSI and may be realized by a dedicated circuit or a general-purpose processor. A field-programmable gate array (FPGA) that can be programmed after manufacture of an LSI or a reconfigurable processor that allows reconfiguration of connections and settings of circuit cells inside an LSI may be utilized.

Also, some or all of the functions of the devices according to the embodiments of the present disclosure may be realized by a processor, such as a CPU, executing a program.

Also, the numerals used in the above description are all exemplary for specifically describing the present disclosure and are not limited to the exemplified numbers.

Also, the order in which the individual steps illustrated in each flowchart described above are executed is exemplary for specifically describing the present disclosure and may be an order other than the above-described order, as long as the same or similar advantages are obtained. Also, one or more of the above-described steps may be executed concurrently (in parallel) with another step.

Since the technique disclosed herein makes it possible to accurately and easily measure a user's sense of taste and makes it possible to collect information regarding the user's sense of taste, it is useful for technique for evaluating the user's sense of taste.

What is claimed is:

1. A method for providing information in an information management system that is used to provide a dish search screen, the method comprising:
    providing, on the dish search screen as one of a plurality of search filters, one search filter for filtering dishes or restaurants based on rating results of the dishes or restaurants rated by a second user who has a sense-of-taste characteristic similar to a sense-of-taste characteristic of a first user;
    obtaining first data indicating an input value in a measurement test regarding sense of taste of the first user from a first communication terminal through a network, wherein the measurement test regarding the sense of taste is used for measuring taste sensitivity of the first user;
    obtaining second data indicating an input value in a measurement test regarding sense of taste of the second user from a second communication terminal through the network;
    obtaining rating information indicating the second user's rating of a dish or a restaurant from the second communication terminal, wherein the rating information indicating the second user's rating of the dish or the restaurant is managed as the second user's rating result of the dish or the restaurant;
    generating a first evaluation value of the first user's sense of taste in association with the first user, based on the first data;
    generating a second evaluation value of the second user's sense of taste in association with the second user, based on the second data; and
    filtering the dishes or the restaurants based on the second user's rating result when a first difference between the first evaluation value and the second evaluation value is in a first predetermined range in a case in which the first user uses the search filter to filter the dishes or the restaurants.

2. The method according to claim 1,
    wherein each measurement test regarding the sense of taste includes a measurement test with respect to at least one type of taste, and the at least one type of taste includes at least one of sweetness, sourness, saltiness, bitterness, or umami;
    the first evaluation value includes an evaluation value for entire sense of taste including the at least one type of taste; and
    the second evaluation value includes an evaluation value for entire sense of taste including the at least one type of taste.

3. The method according to claim 1,
    wherein each measurement test regarding the sense of taste includes a measurement test with respect to at least one type of taste, and the at least one type of taste includes at least one of sweetness, sourness, saltiness, bitterness, or umami;
    the first evaluation value is represented by a first value indicating sensitivity to a first type of taste and a second value indicating sensitivity to a second type of taste, the first type of taste and the second type of taste being included in two types of taste including the at least one type of taste;
    the second evaluation value is represented by a third value indicating sensitivity to the first type of taste and a fourth value indicating sensitivity to the second type of taste; and
    when a second difference between the first value and the third value and a third difference between the second value and the fourth value are both in a second predetermined range, it is decided that the first difference is in the first predetermined range.

4. The method according to claim 1,
    wherein the measurement tests regarding the first user's sense of taste and the second user's sense of taste include measurement tests of taste resolutions of the first user and the second user;
    the measurement tests of the taste resolutions are used to measure what is a smallest difference each of the first user and the second user is capable of recognizing between a plurality of levels with respect to at least one type of taste;
    the first data indicates an input value in the measurement test of the taste resolution of the first user;
    the first evaluation value of the first user's sense of taste is generated based on at least the first data;
    the second data indicates an input value in the measurement test of the taste resolution of the second user; and
    the second evaluation value of the second user's sense of taste is generated based on at least the second data.

5. The method according to claim 1,
    wherein the measurement tests regarding the first user's sense of taste and the second user's sense of taste include measurement tests of taste sensing of the first user and the second user;
    the measurement tests of the taste sensing are used to measure, among no taste and a plurality of levels ranging from a light taste to a strong taste of some kind of taste, at which level from no taste each of the first user and the second user is capable of sensing a distinction as to whether there is no taste or any taste;
    the first data indicates an input value in the measurement test of the taste sensing of the first user;
    the first evaluation value of the first user's sense of taste is generated based on at least the first data;
    the second data indicates an input value in the measurement test of the taste sensing of the second user; and
    the second evaluation value of the second user's sense of taste is generated based on at least the second data.

6. The method according to claim 1,
    wherein the measurement tests regarding the first user's sense of taste and the second user's sense of taste include measurement tests of taste recognition of the first user and the second user;
    the measurement test of the taste recognition is used to measure, among no taste and a plurality of levels ranging from a light taste to a strong taste of at least one type of taste, at which level from no taste each of the first user and the second user is capable of recognizing whether there is no taste or the least the one type of taste;
    the first data indicates an input value in the measurement test of the taste recognition of the first user;
    the first evaluation value of the first user's sense of taste is generated based on at least the first data;
    the second data indicates an input value in the measurement test of taste recognition of the second user; and
    the second evaluation value of the second user's sense of taste is generated based on at least the second data.

7. The method according to claim 1,
wherein the measurement tests regarding the first user's sense of taste and the second user's sense of taste include measurement tests of taste densities of the first user and the second user;
the measurement tests of the taste densities are used to measure whether or not each of the first user and the second user is capable of relatively correctly recognizing at least three levels ranging from a light taste to a strong taste with respect to at least one type of taste;
the first data indicates an input value in the measurement test of the taste density of the first user;
the first evaluation value of the first user's sense of taste is generated based on at least the first data;
the second data indicates an input value in the measurement test of the taste density of the second user; and
the second evaluation value of the second user's sense of taste is generated based on at least the second data.

8. The method according to claim 4,
wherein the input value in the measurement test of the taste resolution of the first user and the input value in the measurement test of the taste resolution of the second user are input at the first communication terminal and the second communication terminal, respectively, by using at least i) a first test meal group including a plurality of test meals corresponding to a plurality of levels ranging from a light sweet taste to a strong sweet taste or ii) a second test meal group including a plurality of test meals corresponding to a plurality of levels ranging from a light salty taste to a strong salty taste.

9. The method according to claim 8,
wherein a first instruction for making each of the first user and the second user input which of a first sweetness test meal and a second sweetness test meal of the plurality of test meals included in the first test meal group is sweeter is output onto a display of each of the first communication terminal and the second communication terminal, the first sweetness test meal and the second sweetness test meal having therebetween a first level gap of two or more levels of the plurality of levels ranging from the light sweet taste to the strong sweet taste; and
the first data and the second data are obtained as responses to the first instruction.

10. The method according to claim 9,
wherein a second instruction for making each of the first user and the second user input which of a third sweetness test meal and a fourth sweetness test meal of the plurality of test meals included in the first test meal group is sweeter, separately from the first sweetness test meal and the second sweetness test meal, is output onto the display of each of the first communication terminal and the second communication terminal, the third sweetness test meal and the fourth sweetness test meal having therebetween a second level gap that is narrower than the first level gap among the plurality of levels ranging from the light sweet taste to the strong sweet taste; and
the first data and the second data are obtained as responses to the second instruction.

11. The method according to claim 10,
wherein a third instruction for making each of the first user and the second user input which of a fifth sweetness test meal and a sixth sweetness test meal of the plurality of test meals included in the first test meal group is sweeter, separately from the first sweetness test meal and the second sweetness test meal, is output onto the display of each of the first communication terminal and the second communication terminal, the fifth sweetness test meal and the sixth sweetness test meal having therebetween a third level gap that is wider than the first level gap among the plurality of levels ranging from the light sweet taste to the strong sweet taste; and
the first data and the second data are obtained as responses to the third instruction.

12. The method according to claim 10,
wherein the second instruction is output when it is decided that the response to the first instruction indicates a correct answer.

13. The method according to claim 11,
wherein the third instruction is output when it is decided that the response to the first instruction indicates an incorrect answer.

14. The method according to claim 5,
wherein the input value in the measurement test of the taste sensing of the first user and the input value in the measurement test of the taste sensing of the second user are input at the first communication terminal and the second communication terminal, respectively, by using at least i) a first test meal group including a plurality of test meals corresponding to a plurality of levels ranging from a light sweet taste to a strong sweet taste, ii) a second test meal group including a plurality of test meals corresponding to a plurality of levels ranging from a light salty taste to a strong salty taste, and iii) a third test meal group including a plurality of tasteless test meals.

15. The method according to claim 14,
wherein a fourth instruction for making each of the first user and the second user use the first test meal group, the second test meal group, and the third test meal group to input whether the test meals included in the first test meal group or the second test meal group are tasteless or not tasteless in order with a level of a lightest taste first is output onto a display of each of the first communication terminal and the second communication terminal; and
the first data and the second data are obtained as responses to the fourth instruction.

16. The method according to claim 6,
wherein the input value in the measurement test of the taste recognition of the first user and the input value in the measurement test of the taste recognition of the second user are input at the first communication terminal and the second communication terminal, respectively, by using at least a first test meal group including a plurality of test meals corresponding to a plurality of levels ranging from a light sweet taste to a strong sweet taste and a second test meal group including a plurality of tasteless test meals.

17. The method according to claim 15,
wherein a fifth instruction for making each of the first user and the second user use the first test meal group and the second test meal group to input whether the test meals included in the first test meal group have no taste or have sweet taste in order with the level of a lightest sweet taste first is output onto a display of each of the first communication terminal and the second communication terminal; and
the first data and the second data are obtained as responses to the fifth instruction.

18. The method according to claim 7,
wherein the input value in the measurement test of the taste density of the first user and the input value in the measurement test of the taste density of the second user are input at the first communication terminal and the second communication terminal, respectively, by using at least a first test meal group including a plurality of test meals corresponding to a plurality of levels ranging from a light sweet taste to a strong sweet taste.

19. The method according to claim 18,
wherein a sixth instruction for making each of the first user and the second user use the first test meal group to input at least three test meals in order of density of taste, the at least three test meals being included in the plurality of test meals included in the first test meal group, is output onto a display of each of the first communication terminal and the second communication terminal, and
the first data and the second data are obtained as responses to the sixth instruction.

20. A method for providing information in an information management system that is used to provide a dish search screen, the method comprising:
providing, on the dish search screen as one of a plurality of search filters, one search filter for filtering dishes or restaurants based on rating results of the dishes or restaurants rated by a second user who has a sense-of-taste characteristic similar to a sense-of-taste characteristic of a first user, wherein a first evaluation value is generated in association with the first user based on a measurement test regarding sense of taste for measuring taste sensitivity, a second evaluation value is generated in association with the second user based on the measurement test, and the dishes or the restaurants are filtered based on the rating results of the dishes or restaurants rated by the second user when a first difference between the first evaluation value and the second evaluation value is in a first predetermined range;
obtaining, from a first communication terminal of the first user through a network, a command indicating that the search filter is selected;
selecting at least one dish filtered by the one search filter or at least one restaurant filtered by the one search filter, based on the command; and
outputting information indicating the selected at least one dish or restaurant to the first communication terminal through the network to display the information on a display of the first communication terminal.

21. The method according to claim 20,
wherein first data indicating an input value in the measurement test regarding sense of taste of the first user is obtained from the first communication terminal through the network, the measurement test regarding the sense of taste being used for measuring taste sensitivity of the first user;
second data indicating an input value in the measurement test regarding sense of taste of the second user is obtained from the second communication terminal of the second user through the network;
rating information indicating the second user's rating of a dish or a restaurant is obtained from the second communication terminal, the rating information indicating the second user's rating of the dish or the restaurant being included in the second user's rating results of the dishes or the restaurants;
the first evaluation value of the first user's sense of taste is generated in association with the first user, based on the first data;
the second evaluation value of the second user's sense of taste is generated in association with the second user, based on the second data; and
the dishes or the restaurants are filtered based on the rating results of the dishes or restaurants rated by the second user when the first difference between the first evaluation value and the second evaluation value is in the first predetermined range in a case in which the first user uses the one search filter to filter the dishes or the restaurants.

* * * * *